(12) United States Patent
Fitzgerald et al.

(10) Patent No.: US 8,124,748 B2
(45) Date of Patent: Feb. 28, 2012

(54) CELL SURFACE GLYCOPROTEIN

(75) Inventors: Stephen Fitzgerald, London (GB); Richard Fagan, London (GB); Jadwiga Bienkowska, Cambridge, MA (US); Christine Power, Thoiry (FR); Melanie Yorke-Smith, Guangzhou (CN)

(73) Assignee: Ares Trading S.A., Aubonne (CH)

( * ) Notice: Subject to any disclaimer, the term of this patent is extended or adjusted under 35 U.S.C. 154(b) by 527 days.

(21) Appl. No.: 11/660,014

(22) PCT Filed: Aug. 11, 2005

(86) PCT No.: PCT/GB2005/003165
§ 371 (c)(1), (2), (4) Date: Sep. 13, 2007

(87) PCT Pub. No.: WO2006/016172
PCT Pub. Date: Feb. 16, 2006

(65) Prior Publication Data
US 2008/0124309 A1    May 29, 2008

(30) Foreign Application Priority Data
Aug. 11, 2004 (GB) .................. 0417887.7

(51) Int. Cl.
| C07H 21/02 | (2006.01) |
| C07H 21/04 | (2006.01) |
| C12N 15/00 | (2006.01) |
| C12N 5/00 | (2006.01) |
| C12N 5/02 | (2006.01) |
| C12N 1/00 | (2006.01) |
| C12P 21/06 | (2006.01) |

(52) U.S. Cl. ............... 536/23.1; 435/320.1; 435/325; 435/243; 435/69.1
(58) Field of Classification Search ............. 536/23.1; 435/320.1, 325, 243, 69.1
See application file for complete search history.

(56) References Cited

U.S. PATENT DOCUMENTS
6,022,715 A    2/2000  Merenkova et al.
6,783,961 B1 *  8/2004  Edwards et al. ............. 435/91.1

FOREIGN PATENT DOCUMENTS
| EP | 1033401 A2 | 9/2000 |
| EP | 1104808 A1 | 6/2001 |
| WO | WO 96/34981 | 11/1996 |
| WO | WO 99/47540 | 9/1999 |
| WO | PCT/IB99/00712 | * 10/1999 |
| WO | WO 01/07611 | 2/2001 |
| WO | WO 02/068579 | 9/2002 |

OTHER PUBLICATIONS

Parmley et al., How do synonymous mutations affect fitness? Bioessays, 29(6): 515-9, 2007.*
Database EMBL, Accession No. AC010619, Jun. 4, 2002, XP002376566, pp. 1-2.
Adams, M. D. et al. "Rapid cDNA sequencing (expressed sequence tags) from a directionally cloned human infant brain cDNA library" *Nature Genetics*, Aug. 1993, pp. 373-380, vol. 4.
Adams, M. D. et al. "3,400 new expressed sequence tags identify diversity of transcripts in human brain" *Nature Genetics*, Jul. 1993, pp. 256-267, vol. 4.
Carninci, P. et al. "High-Efficiency Full-Length cDNA Cloning by Biotinylated CAP Trapper" *Genomics*, 1996, pp. 327-336, vol. 37, No. 0567.
Kato, S. et al. "Construction of a human full-length cDNA bank" *Gene*, 1994, pp. 243-250, vol. 150.

* cited by examiner

*Primary Examiner* — Wu-Cheng Winston Shen
(74) *Attorney, Agent, or Firm* — Saliwanchik, Lloyd & Eisenschenk

(57) ABSTRACT

This invention relates to a novel protein, termed INSP201, herein identified as a cell surface glycoprotein, and to the use of this protein and nucleic acid sequences from the encoding gene in the diagnosis, prevention and treatment of disease.

12 Claims, 11 Drawing Sheets

FIG. 1

Glycosylation site prediction for INSP201 using NetNGlyc 1.0

Predictions for N-Glycosylation sites in 1 sequence

Name: hg16_dna._1   Length: 518

```
MKSFSRILFLVFLLAGLRSKAAPSAPLPLGCGFPDMAHPSETSPLKGASENSKRDRLNPEFPGTPYPEPSKLPHTVSLET    80
FPLDFTEPLNPDLRETPHPESPETPKADSLTTSISESLDMPKTNLSKMAHPESSETPTPGPTEMPHPGSPETPKPNFSKT   160
SRPEFPETPNTDLMQTTPQESPEILQLNATEVSQAELPETSNTNPTKTPDPKSPEKHDLNSTETPNSEFLQALHPDPSKT   240
PHPESHVTHNPSPTEISQTEFPTTYYQNATDVPRTSDPQISTSLYPETPVPFKDDATALNELSLNPKPGTPAAIQPDSPK   320
LPTSDSPGMVELKAPQNSGPKESNVPPPSARIAGPPALPGRPSQLAPATLRAPQRHSRGEGVNTIIVVERVKETGVTLVG   400
RPRGAAGGALCLFFAGTALLIGIFVLLWCLYRRAARQRPFAHHRLPDDGDEPVLHLDAPKDPYDLYFYAPDTWVPSHIAT   480
KQPPPTPPLPPKLPPPPRGGRPQRLEALSPATLPNNFV

................................................................................    80
..........................................N..............................N....   160
.........................N.................N.................N.................   240
...............N................................................................   320
................................................................................   400
................................................................................   480
.....................................
```

(Threshold=0.5)

---

| SeqName | Position | Potential | Jury agreement | NGlyc result | |
|---|---|---|---|---|---|
| hg16_dna._1 | 124 NLSK | 0.6568 | (9/9) | ++ | |
| hg16_dna._1 | 156 NFSK | 0.7230 | (9/9) | ++ | |
| hg16_dna._1 | 188 NATE | 0.6670 | (9/9) | ++ | |
| hg16_dna._1 | 204 NPTK | 0.8066 | (9/9) | +++ | WARNING: PRO-X1. |
| hg16_dna._1 | 220 NSTE | 0.7010 | (9/9) | ++ | |
| hg16_dna._1 | 250 NPSP | 0.2278 | (9/9) | --- | |
| hg16_dna._1 | 268 NATD | 0.6469 | (9/9) | ++ | |

---

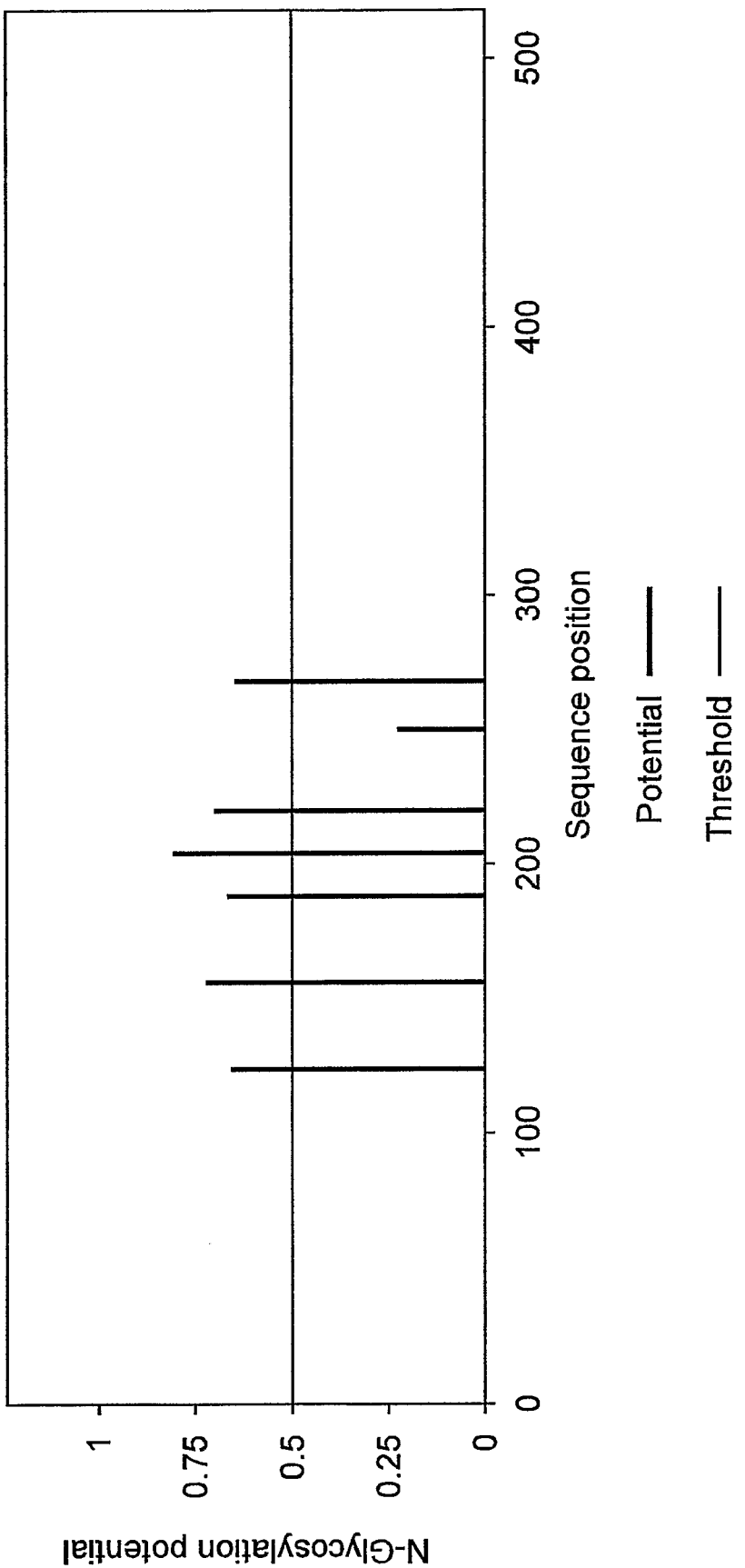
FIG. 1 (contd.)

FIG. 2

```
  1 gtgggcgtgg cctccgggag tgggcggggc tcctgggagc cttcggcctt aaccccttcc
 61 ttcccgctct cccccgcagc tataggtatc tgccagagct atgaaatcat tcagccggat
                                                  m  k  s  f  s  r 121 cctcttcctc gtcttcctcc tcgccggcct gaggtccaag gccgctccct cagcccctct
     i  l  f  l  v  f  l  l  a  g  l  r  s  k  a  a  p  s  a  p
    ─────────────────────▶
         INSP201-CP1

181 gcctttgggc tgtggctttc cggacatggc ccacccctct gagacttccc ctctgaaggg
     l  p  l  g  c  g  f  p  d  m  a  h  p  s  e  t  s  p  l  k 241 tgcttctgaa aattccaaac gagatcgcct aacccagaa tttcctggga ctccttaccc
     g  a  s  e  n  s  k  r  d  r  l  n  p  e  f  p  g  t  p  y 301 tgagccttcc aagctacctc atacggtttc cctggaaacc ttcccacttg acttcactga
     p  e  p  s  k  l  p  h  t  v  s  l  e  t  f  p  l  d  f  t 361 gcccctcaac cctgacctcc gagaaacccc gcacccagag tctcctgaga cccccaaagc
     e  p  l  n  p  d  l  r  e  t  p  h  p  e  s  p  e  t  p  k 421 tgactcactc acaacctcaa tatcagaatc cctggacatg cccaaaacta acctctccaa
     a  d  s  l  t  t  s  i  s  e  s  l  d  m  p  k  t  n  l  s 481 aatggcacac ccagagtctt ctgagacccc cacacctggc ccaactgaaa tgccacaccc
     k  m  a  h  p  e  s  s  e  t  p  t  p  g  p  t  e  m  p  h 541 aggatcccct gagaccccca aacctaactt ctccaaaact tcacgcccag aatttcctga
     p  g  s  p  e  t  p  k  p  n  f  s  k  t  s  r  p  e  f  p
```

FIG. 2(contd.)

```
 601  gaccccaaac actgacctta tgcaaactac accccaagaa tccccagaga ttctgcagct
       e  t  p  n  t  d  l  m  q  t  t  p  q  e  s  p  e  i  l  q 661  taatgccact gaagtctcac aggcagaact ccccgagacc tcaaacacta accctaccaa
       l  n  a  t  e  v  s  q  a  e  l  p  e  t  s  n  t  n  p  t 721  gaccccctgac cccaaatccc cagaaaagca tgacctcaac tccactgaga ccccaaactc
       k  t  p  d  p  k  s  p  e  k  h  d  l  n  s  t  e  t  p  n 781  tgaatttctc caagctctcc atcctgaccc ttctaaaacc ccccacccag aatcccatgt
       s  e  f  l  q  a  l  h  p  d  p  s  k  t  p  h  p  e  s  h 841  gacccacaat cccagcccca ccgaaatttc ccaaacagaa ttccccacaa cctactacca
       v  t  h  n  p  s  p  t  e  i  s  q  t  e  f  p  t  t  y  y 901  aaatgcaaca gatgtaccca ggacctccga ccctcaaatc tccactagtc tctacccaga
       q  n  a  t  d  v  p  r  t  s  d  p  q  i  s  t  s  l  y  p 961  aacacctgtg cccttcaagg atgacgccac tgctctaaat gagctgtccc tgaatcccaa
       e  t  p  v  p  f  k  d  d  a  t  a  l  n  e  l  s  l  n  p 1021  accaggaaca cctgcagcca tccagcccga ctccccaaaa ttgcccactt cagattctcc
       k  p  g  t  p  a  a  i  q  p  d  s  p  k  l  p  t  s  d  s 1081  aggaatggtt gagctgaagg ccccccagaa ctctggccct aaggagtcca acgtccctcc
       p  g  m  v  e  l  k  a  p  q  n  s  g  p  k  e  s  n  v  p
```

```
1141 tccctcagcc cggattgcag gtccccctgc tcttccaggg cgccccagtc agttggcccc
      p   p   s   a   r   i   a   g   p   p   a   l   p   g   r   p   s   q   l   a 1201 tgccactctg cgggcacccc agaggcacag ccgaggtgag ggagtcaaca ccatcatcgt
      p   a   t   l   r   a   p   q   r   h   s   r   g   e   g   v   n   t   i   i 1261 ggtggagcga gtgaaggaga ccggcgtgac tctggtgggg cgaccacgtg gcgcagcagg
      v   v   e   r   v   k   e   t   g   v   t   l   v   g   r   p   r   g   a   a
                                     ◄─────────────────────────────────
                                              INSP201-CP2

1321 cggggccctc tgcctgttct tcgcggggac cgcgctgctg atcggcatct tgtgctgct
      g   g   a   l   c   l   f   f   a   g   t   a   l   l   i   g   i   f   v   l 1381 gtggtgtctt taccgccggg cagctagaca gcggcccttc gcacatcacc ggcttccgga
      l   w   c   l   y   r   r   a   a   r   q   r   p   f   a   h   h   r   l   p 1441 cgacggagat gaaccggttc tgcatttgga cgccccgaaa gaccccctacg acctctactt
      d   d   g   d   e   p   v   l   h   l   d   a   p   k   d   p   y   d   l   y 1501 ttatgctccg gatacctggg tcccttccca catcgccacc aagcagcccc cgcccacacc
      f   y   a   p   d   t   w   v   p   s   h   i   a   t   k   q   p   p   p   t 1561 tcctctgcca ccaaagctgc ccccgccgcc ccgcgggggt cgcccgcagc gtctggaggc
      p   p   l   p   p   k   l   p   p   p   p   r   g   g   r   p   q   r   l   e 1621 cctgtccccc gccacgctcc ccaacaactt cgtgtgagcc ccaccgagtt ctgccggacc
      a   l   s   p   a   t   l   p   n   n   f   v 1681 tgcacatccc cacagtgaag gaaaaccctg cgcttctggt atgcttagct agagtagtgc
1741 cccggataaa gg
```

Position and sense of PCR primers ———►

```
  1  atgaaatcat tcagccggat cctcttcctc gtcttcctcc tcgccggcct gaggtccaag
      m  k  s  f  s  r  i  l  f  l  v  f  l  l  a  g  l  r  s  k
     ────────────────────────────────────────────▶
                        INSP201-CP1

61  gccgctccct cagcccctct gcctttgggc tgtggctttc cggacatggc ccacccctct
      a  a  p  s  a  p  l  p  l  g  c  g  f  p  d  m  a  h  p  s 121  gagacttccc ctctgaaggg tgcttctgaa aattccaaac gagatcgcct taacccagaa
      e  t  s  p  l  k  g  a  s  e  n  s  k  r  d  r  l  n  p  e 181  tttcctggga ctccttaccc tgagccttcc aagctacctc atacggtttc cctggaaacc
      f  p  g  t  p  y  p  e  p  s  k  l  p  h  t  v  s  l  e  t 241  ttcccacttg acttcactga gcccctcaac cctgacctcc gagaaacccc gcacccagag
      f  p  l  d  f  t  e  p  l  n  p  d  l  r  e  t  p  h  p  e 301  tctcctgaga cccccaaagc tgactcactc acaacctcaa tatcagaatc cctggacatg
      s  p  e  t  p  k  a  d  s  l  t  t  s  i  s  e  s  l  d  m 361  cccaaaacta acctctccaa aatggcacac ccagagtctt ctgagacccc cacacctggc
      p  k  t  n  l  s  k  m  a  h  p  e  s  s  e  t  p  t  g 421  ccaactgaaa tgccacaccc aggatcccct gagaccccca aacctaactt ctccaaaact
      p  t  e  m  p  h  p  g  s  p  e  t  p  k  p  n  f  s  k  t 481  tcacgcccag aatttcctga ccccaaaac actgacctta tgcaaactac accccaagaa
      s  r  p  e  f  p  e  t  p  n  t  d  l  m  q  t  t  p  q  e 541  tccccagaga ttctgcagct taatgccact gaagtctcac aggcagaact ccccgagacc
      s  p  e  i  l  q  l  n  a  t  e  v  s  q  a  e  l  p  e  t 601  tcaaacacta accctaccaa gaccccctgac cccaaatccc cagaaaagca tgacctcaac
      s  n  t  n  p  t  k  t  p  d  p  k  s  p  e  k  h  d  l  n 661  tccactgaga ccccaaactc tgaatttctc caagctctcc atcctgaccc ttctaaaacc
      s  t  e  t  p  n  s  e  f  l  q  a  l  h  p  d  p  s  k  t 721  ccccacccag aatcccatgt gacccacaat cccagcccca ccgaaatttc ccaaacagaa
      p  h  p  e  s  h  v  t  h  n  p  s  p  t  e  i  s  q  t  e
```

```
 781 ttccccacaa cctactacca aaatgcaaca gatgtaccca ggacctccga ccctcaaatc
      f  p  t   t  y  y   q  n  a   t  d  v   p  r  t   s  d  p  q  i 841 tccactagtc tctacccaga aacacctgtg cccttcaagg atgacgccac tgctctaaat
      s  t  s   l  y  p   e  t  p  v  p  f  k   d  d  a   t  a  l  n 901 gagctgtccc tgaatcccaa accaggaaca cctgcagcca tccagcccga ctccccaaaa
      e  l  s   l  n  p   k  p  g   t  p  a  a   i  q  p   d  s  p  k 961 ttgcccactt cagattctcc aggaatggtt gagctgaagg ccccccagaa ctctggccct
      l  p  t   s  d  s   p  g  m  v  e  l  k   a  p  q   n  s  g  p 1021 aaggagtcca acgcccctcc tccctcagcc cggattgcag gtcccccctgc tcttccaggg
      k  e  s   n  a  p   p  p  s   a  r  i   a  g  p   p  a  l  p  g 1081 cgccccagtc agttggcccc tgccactctg cgggcacccc agaggcacag ccgaggtgag
      r  p  s   q  l  a   p  a  t   l  r  a   p  q  r   h  s  r  g  e 1141 ggagtcaaca ccatcatcgt ggtggagcga gtgaaggaga ccggcgtgac tctggtgggg
      g  v  n   t  i  i   v  v  e  r  v  k  e   t  g  v   t  l  v  g
                                   ◄─────────────────────────────────
                                              INSP201-CP2

1201 cgaccacgtg gcgca
      r  p  r  g  a
      ─────────────
```

Position and sense of PCR primers ———▶

FIG. 3(contd.)

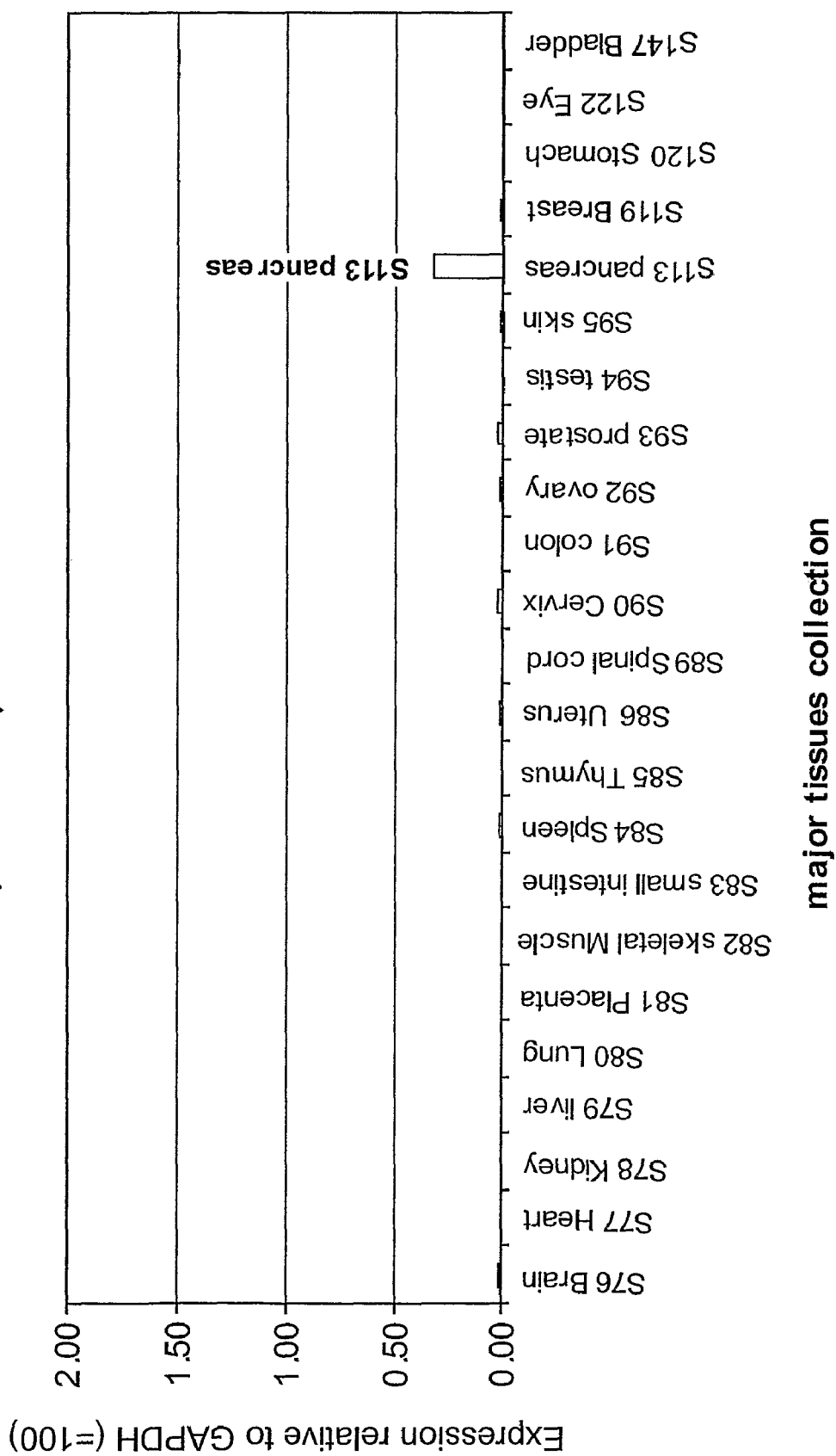

Taqman analysis of INSP201

SEQUENCE LISTING

```
<160> NUMBER OF SEQ ID NOS: 53

<210> SEQ ID NO 1
<211> LENGTH: 1183
<212> TYPE: DNA
<213> ORGANISM: Homo sapiens

<400> SEQUENCE: 1
atgaaatcat tcagccggat cctcttcctc gtcttcctcc tcgccggcct gaggtccaag      60
```

```
gccgctccct cagcccctct gcctttgggc tgtggctttc cggacatggc ccacccctct      120
gagacttccc ctctgaaggg tgcttctgaa aattccaaac gagatcgcct taacccagaa      180
tttcctggga ctccttaccc tgagccttcc aagctacctc atacggtttc cctggaaacc      240
ttcccacttg acttcactga gcccctcaac cctgacctcc gagaaacccc gcacccagag      300
tctcctgaga cccccaaagc tgactcactc acaacctcaa tatcagaatc cctggacatg      360
cccaaaacta acctctccaa aatggcacac ccagagtctt ctgagacccc cacacctggc      420
ccaactgaaa tgccacaccc aggatcccct gagaccccca acctaacttc tccaaaact       480 tcacgcccag aatttcctga ccccccaaac actgaccctta tgcaaactac accccaagaa    540
tccccagaga ttctgcagct taatgccact gaagtctcac aggcagaact ccccgagacc      600
tcaaacacta accctaccaa gaccctgac cccaaatccc cagaaaagca tgacctcaac       660
tccactgaga ccccaaactc tgaatttctc caagctctcc atcctgaccc ttctaaaacc      720
ccccacccag aatcccatgt gacccacaat cccagcccca ccgaaatttc ccaaacagaa      780
ttccccacaa cctactacca aaatgcaaca gatgtaccca ggacctccga ccctcaaatc      840
tccactagtc tctacccaga aacacctgtg cccttcaagg atgacgccac tgctctaaat      900
gagctgtccc tgaatcccaa accaggaaca cctgcagcca tccagcccga ctccccaaaa     960
ttgcccactt cagattctcc aggaatggtt gagctgaagg ccccccagaa ctctggccct     1020
aaggagtcca acgtccctcc tccctcagcc cggattgcag gtccccctgc tcttccaggg     1080
cgccccagtc agttggcccc tgccactctg cgggcacccc agaggcacag ccgaggtgag     1140
ggagtcaaca ccatcatcgt ggtggagcga gtgaaggaga ccg                      1183

<210> SEQ ID NO 2
<211> LENGTH: 395
<212> TYPE: PRT
<213> ORGANISM: Homo sapiens

<400> SEQUENCE: 2

Met Lys Ser Phe Ser Arg Ile Leu Phe Leu Val Phe Leu Leu Ala Gly
1               5                   10                  15

Leu Arg Ser Lys Ala Ala Pro Ser Ala Pro Leu Pro Leu Gly Cys Gly
                20                  25                  30

Phe Pro Asp Met Ala His Pro Ser Glu Thr Ser Pro Leu Lys Gly Ala
            35                  40                  45

Ser Glu Asn Ser Lys Arg Asp Arg Leu Asn Pro Glu Phe Pro Gly Thr
        50                  55                  60

Pro Tyr Pro Glu Pro Ser Lys Leu Pro His Thr Val Ser Leu Glu Thr
65                  70                  75                  80

Phe Pro Leu Asp Phe Thr Glu Pro Leu Asn Pro Asp Leu Arg Glu Thr
                85                  90                  95

Pro His Pro Glu Ser Pro Glu Thr Pro Lys Ala Asp Ser Leu Thr Thr
            100                 105                 110

Ser Ile Ser Glu Ser Leu Asp Met Pro Lys Thr Asn Leu Ser Lys Met
        115                 120                 125

Ala His Pro Glu Ser Ser Glu Thr Pro Thr Pro Gly Pro Thr Glu Met
    130                 135                 140

Pro His Pro Gly Ser Pro Glu Thr Pro Lys Pro Asn Phe Ser Lys Thr
145                 150                 155                 160

Ser Arg Pro Glu Phe Pro Glu Thr Pro Asn Thr Asp Leu Met Gln Thr
                165                 170                 175

Thr Pro Gln Glu Ser Pro Glu Ile Leu Gln Leu Asn Ala Thr Glu Val
```

-continued

```
                    180                 185                 190
Ser Gln Ala Glu Leu Pro Glu Thr Ser Asn Thr Asn Pro Lys Thr
            195                 200                 205

Pro Asp Pro Lys Ser Pro Glu Lys His Asp Leu Asn Ser Thr Glu Thr
    210                 215                 220

Pro Asn Ser Glu Phe Leu Gln Ala Leu His Pro Asp Pro Ser Lys Thr
225                 230                 235                 240

Pro His Pro Glu Ser His Val Thr His Asn Pro Ser Pro Thr Glu Ile
                245                 250                 255

Ser Gln Thr Glu Phe Pro Thr Thr Tyr Tyr Gln Asn Ala Thr Asp Val
            260                 265                 270

Pro Arg Thr Ser Asp Pro Gln Ile Ser Thr Ser Leu Tyr Pro Glu Thr
        275                 280                 285

Pro Val Pro Phe Lys Asp Asp Ala Thr Ala Leu Asn Glu Leu Ser Leu
    290                 295                 300

Asn Pro Lys Pro Gly Thr Pro Ala Ala Ile Gln Pro Asp Ser Pro Lys
305                 310                 315                 320

Leu Pro Thr Ser Asp Ser Pro Gly Met Val Glu Leu Lys Ala Pro Gln
                325                 330                 335

Asn Ser Gly Pro Lys Glu Ser Asn Val Pro Pro Ser Ala Arg Ile
            340                 345                 350

Ala Gly Pro Pro Ala Leu Pro Gly Arg Pro Ser Gln Leu Ala Pro Ala
        355                 360                 365

Thr Leu Arg Ala Pro Gln Arg His Ser Arg Gly Glu Gly Val Asn Thr
    370                 375                 380

Ile Ile Val Val Glu Arg Val Lys Glu Thr Gly
385                 390                 395

<210> SEQ ID NO 3
<211> LENGTH: 174
<212> TYPE: DNA
<213> ORGANISM: Homo sapiens

<400> SEQUENCE: 3
gcgtgactct ggtggggcga ccacgtggcg cagcaggcgg ggccctctgc ctgttcttcg    60
cggggaccgc gctgctgatc ggcatctttg tgctgctgtg gtgtctttac cgccgggcag   120
ctagacagcg gcccttcgca catcaccggc ttccggacga cggagatgaa ccgg         174

<210> SEQ ID NO 4
<211> LENGTH: 58
<212> TYPE: PRT
<213> ORGANISM: Homo sapiens

<400> SEQUENCE: 4

Val Thr Leu Val Gly Arg Pro Arg Gly Ala Ala Gly Gly Ala Leu Cys
1               5                   10                  15

Leu Phe Phe Ala Gly Thr Ala Leu Leu Ile Gly Ile Phe Val Leu Leu
            20                  25                  30

Trp Cys Leu Tyr Arg Arg Ala Ala Arg Gln Arg Pro Phe Ala His His
        35                  40                  45

Arg Leu Pro Asp Asp Gly Asp Glu Pro Val
    50                  55

<210> SEQ ID NO 5
<211> LENGTH: 197
<212> TYPE: DNA
<213> ORGANISM: Homo sapiens
```

<400> SEQUENCE: 5

```
ttctgcattt ggacgccccg aaagacccct acgacctcta cttttatgct ccggatacct    60
gggtcccttc ccacatcgcc accaagcagc cccgcccac acctcctctg ccaccaaagc    120
tgcccccgcc gcccgcggg ggtcgcccgc agcgtctgga ggccctgtcc cccgccacgc    180
tccccaacaa cttcgtg                                                  197
```

<210> SEQ ID NO 6
<211> LENGTH: 65
<212> TYPE: PRT
<213> ORGANISM: Homo sapiens

<400> SEQUENCE: 6

Leu His Leu Asp Ala Pro Lys Asp Pro Tyr Asp Leu Tyr Phe Tyr Ala
1               5                   10                  15

Pro Asp Thr Trp Val Pro Ser His Ile Ala Thr Lys Gln Pro Pro Pro
            20                  25                  30

Thr Pro Pro Leu Pro Pro Lys Leu Pro Pro Pro Pro Arg Gly Gly Arg
        35                  40                  45

Pro Gln Arg Leu Glu Ala Leu Ser Pro Ala Thr Leu Pro Asn Asn Phe
    50                  55                  60

Val
65

<210> SEQ ID NO 7
<211> LENGTH: 1554
<212> TYPE: DNA
<213> ORGANISM: Homo sapiens

<400> SEQUENCE: 7

```
atgaaatcat tcagccggat cctcttcctc gtcttcctcc tcgccggcct gaggtccaag    60
gccgctccct cagcccctct gcctttgggc tgtggctttc cggacatggc ccacccctct    120
gagacttccc ctctgaaggg tgcttctgaa aattccaaac gagatcgcct taacccagaa    180
tttcctggga ctccttaccc tgagccttcc aagctaccte atacggtttc cctggaaacc    240
ttcccacttg acttcactga gcccctcaac cctgacctcc gagaaacccc gcacccagag    300
tctcctgaga cccccaaagc tgactcactc acaacctcaa tatcagaatc cctggacatg    360
cccaaaacta acctctccaa atggcacac ccagagtctt ctgagacccc cacacctggc    420
ccaactgaaa tgccacaccc aggatcccct gagacccca aacctaactt ctccaaaact    480
tcacgcccag aatttcctga ccccaaac actgaccta tgcaaactac accccaagaa    540
tccccagaga ttctgcagct taatgccact gaagtctcac aggcagaact ccccgagacc    600
tcaaacacta accctaccaa gaccctgac ccaaatccc agaaaagca tgacctcaac    660
tccactgaga cccaaactc tgaatttctc caagctctcc atcctgaccc ttctaaaacc    720
ccccacccag aatccatgt gacccacaat ccagccca ccgaaatttc caaacagaa    780
ttccccacaa cctactacca aaatgcaaca gatgtaccca ggacctccga ccctcaaatc    840
tccactagtc tctacccaga aacacctgtg cccttcaagg atgacgccac tgctctaaat    900
gagctgtccc tgaatccaa accaggaaca cctgcagcca tccagcccga ctccccaaa    960
ttgcccactt cagattctcc aggaatggtt gagctgaagg ccccccagaa ctctggccct    1020
aaggagtcca cgtccctcc tccctcagcc ggattgcag gtcccctgc tcttccaggg    1080
cgccccagtc agttggcccc tgccactctg cgggcaccca gaggcacag ccgaggtgag    1140
```

```
ggagtcaaca ccatcatcgt ggtggagcga gtgaaggaga ccggcgtgac tctggtgggg    1200
cgaccacgtg gcgcagcagg cggggccctc tgcctgttct tcgcggggac cgcgctgctg    1260
atcggcatct ttgtgctgct gtggtgtctt taccgccggg cagctagaca gcggcccttc    1320
gcacatcacc ggcttccgga cgacggagat gaaccggttc tgcatttgga cgccccgaaa    1380
gacccctacg acctctactt ttatgctccg gatacctggg tcccttccca catcgccacc    1440
aagcagcccc cgcccacacc tcctctgcca ccaaagctgc cccgccgcc ccgcgggggt     1500 cgcccgcagc gtctggaggc cctgtccccc gccacgctcc ccaacaactt cgtg          1554
```

<210> SEQ ID NO 8
<211> LENGTH: 518
<212> TYPE: PRT
<213> ORGANISM: Homo sapiens

<400> SEQUENCE: 8

```
Met Lys Ser Phe Ser Arg Ile Leu Phe Leu Val Phe Leu Leu Ala Gly
1               5                   10                  15

Leu Arg Ser Lys Ala Ala Pro Ser Ala Pro Leu Pro Leu Gly Cys Gly
                20                  25                  30

Phe Pro Asp Met Ala His Pro Ser Glu Thr Ser Pro Leu Lys Gly Ala
            35                  40                  45

Ser Glu Asn Ser Lys Arg Asp Arg Leu Asn Pro Glu Phe Pro Gly Thr
        50                  55                  60

Pro Tyr Pro Glu Pro Ser Lys Leu Pro His Thr Val Ser Leu Glu Thr
65                  70                  75                  80

Phe Pro Leu Asp Phe Thr Glu Pro Leu Asn Pro Asp Leu Arg Glu Thr
                85                  90                  95

Pro His Pro Glu Ser Pro Glu Thr Pro Lys Ala Asp Ser Leu Thr Thr
            100                 105                 110

Ser Ile Ser Glu Ser Leu Asp Met Pro Lys Thr Asn Leu Ser Lys Met
        115                 120                 125

Ala His Pro Glu Ser Ser Glu Thr Pro Thr Pro Gly Pro Thr Glu Met
    130                 135                 140

Pro His Pro Gly Ser Pro Glu Thr Pro Lys Pro Asn Phe Ser Lys Thr
145                 150                 155                 160

Ser Arg Pro Glu Phe Pro Glu Thr Pro Asn Thr Asp Leu Met Gln Thr
                165                 170                 175

Thr Pro Gln Glu Ser Pro Glu Ile Leu Gln Leu Asn Ala Thr Glu Val
            180                 185                 190

Ser Gln Ala Glu Leu Pro Glu Thr Ser Asn Thr Asn Pro Thr Lys Thr
        195                 200                 205

Pro Asp Pro Lys Ser Pro Glu Lys His Asp Leu Asn Ser Thr Glu Thr
    210                 215                 220

Pro Asn Ser Glu Phe Leu Gln Ala Leu His Pro Asp Pro Ser Lys Thr
225                 230                 235                 240

Pro His Pro Glu Ser His Val Thr His Asn Pro Ser Pro Thr Glu Ile
                245                 250                 255

Ser Gln Thr Glu Phe Pro Thr Thr Tyr Tyr Gln Asn Ala Thr Asp Val
            260                 265                 270

Pro Arg Thr Ser Asp Pro Gln Ile Ser Thr Ser Leu Tyr Pro Glu Thr
        275                 280                 285

Pro Val Pro Phe Lys Asp Asp Ala Thr Ala Leu Asn Glu Leu Ser Leu
    290                 295                 300

Asn Pro Lys Pro Gly Thr Pro Ala Ala Ile Gln Pro Asp Ser Pro Lys
```

```
                    305                 310                 315                 320
Leu Pro Thr Ser Asp Ser Pro Gly Met Val Glu Leu Lys Ala Pro Gln
                325                 330                 335

Asn Ser Gly Pro Lys Glu Ser Asn Val Pro Pro Ser Ala Arg Ile
            340                 345                 350

Ala Gly Pro Pro Ala Leu Pro Gly Arg Pro Ser Gln Leu Ala Pro Ala
                355                 360                 365

Thr Leu Arg Ala Pro Gln Arg His Ser Arg Gly Glu Gly Val Asn Thr
            370                 375                 380

Ile Ile Val Val Glu Arg Val Lys Glu Thr Gly Val Thr Leu Val Gly
385                 390                 395                 400

Arg Pro Arg Gly Ala Ala Gly Gly Ala Leu Cys Leu Phe Phe Ala Gly
                405                 410                 415

Thr Ala Leu Leu Ile Gly Ile Phe Val Leu Leu Trp Cys Leu Tyr Arg
            420                 425                 430

Arg Ala Ala Arg Gln Arg Pro Phe Ala His His Arg Leu Pro Asp Asp
                435                 440                 445

Gly Asp Glu Pro Val Leu His Leu Asp Ala Pro Lys Asp Pro Tyr Asp
            450                 455                 460

Leu Tyr Phe Tyr Ala Pro Asp Thr Trp Val Pro Ser His Ile Ala Thr
465                 470                 475                 480

Lys Gln Pro Pro Pro Thr Pro Pro Leu Pro Lys Leu Pro Pro Pro
                485                 490                 495

Pro Arg Gly Gly Arg Pro Gln Arg Leu Glu Ala Leu Ser Pro Ala Thr
            500                 505                 510

Leu Pro Asn Asn Phe Val
        515

<210> SEQ ID NO 9
<211> LENGTH: 1120
<212> TYPE: DNA
<213> ORGANISM: Homo sapiens

<400> SEQUENCE: 9
gctccctcag cccctctgcc tttgggctgt ggctttccgg acatggccca ccctctgag      60 acttcccctc tgaagggtgc ttctgaaaat tccaaacgag atcgccttaa cccagaattt    120
cctgggactc cttaccctga gccttccaag ctacctcata cggtttccct ggaaaccttc    180
ccacttgact tcactgagcc cctcaaccct gacctccgag aaaccccgca cccagagtct    240
cctgagaccc ccaaagctga ctcactcaca acctcaatat cagaatccct ggacatgccc    300
aaaactaacc tctccaaaat ggcacaccca gagtcttctg agaccccacc acctggccca    360
actgaaatgc cacccccagg atccctgag accccaaac ctaacttctc caaaacttca     420
cgcccagaat tcctgagac cccaaacact gaccttatgc aaactacacc caagaatcc    480 ccagagattc tgcagcttaa tgccactgaa gtctcacagg cagaactccc cgagacctca    540
aacactaacc ctaccaagac ccctgacccc aaatcccag aaaagcatga cctcaactcc    600
actgagaccc caaactctga atttctccaa gctctccatc ctgacccttc taaaccccc    660 cacccagaat cccatgtgac ccacaatccc agccccaccg aaatttccca aacagaattc    720
cccacaacct actaccaaaa tgcaacagat gtacccagga cctccgaccc tcaaatctcc    780
actagtctct acccagaaac acctgtgccc ttcaaggatg acgccactgc tctaaatgag    840
ctgtccctga atcccaaacc aggaacacct gcagccatcc agcccgactc ccaaaaattg    900
cccacttcag attctccagg aatggttgag ctgaaggccc ccagaactc tggccctaag    960
```

```
gagtccaacg tccctcctcc ctcagcccgg attgcaggtc ccctgctct tccagggcgc    1020 cccagtcagt tggcccctgc cactctgcgg gcaccccaga ggcacagccg aggtgaggga    1080
gtcaacacca tcatcgtggt ggagcgagtg aaggagaccg                         1120
```

<210> SEQ ID NO 10
<211> LENGTH: 374
<212> TYPE: PRT
<213> ORGANISM: Homo sapiens

<400> SEQUENCE: 10

```
Ala Pro Ser Ala Pro Leu Pro Leu Gly Cys Gly Phe Pro Asp Met Ala
1               5                   10                  15

His Pro Ser Glu Thr Ser Pro Leu Lys Gly Ala Ser Glu Asn Ser Lys
            20                  25                  30

Arg Asp Arg Leu Asn Pro Glu Phe Pro Gly Thr Pro Tyr Pro Glu Pro
        35                  40                  45

Ser Lys Leu Pro His Thr Val Ser Leu Glu Thr Phe Pro Leu Asp Phe
    50                  55                  60

Thr Glu Pro Leu Asn Pro Asp Leu Arg Glu Thr Pro His Pro Glu Ser
65                  70                  75                  80

Pro Glu Thr Pro Lys Ala Asp Ser Leu Thr Thr Ser Ile Ser Glu Ser
                85                  90                  95

Leu Asp Met Pro Lys Thr Asn Leu Ser Lys Met Ala His Pro Glu Ser
            100                 105                 110

Ser Glu Thr Pro Thr Pro Gly Pro Thr Glu Met Pro His Pro Gly Ser
        115                 120                 125

Pro Glu Thr Pro Lys Pro Asn Phe Ser Lys Thr Ser Arg Pro Glu Phe
    130                 135                 140

Pro Glu Thr Pro Asn Thr Asp Leu Met Gln Thr Thr Pro Gln Glu Ser
145                 150                 155                 160

Pro Glu Ile Leu Gln Leu Asn Ala Thr Glu Val Ser Gln Ala Glu Leu
                165                 170                 175

Pro Glu Thr Ser Asn Thr Asn Pro Thr Lys Thr Pro Asp Pro Lys Ser
            180                 185                 190

Pro Glu Lys His Asp Leu Asn Ser Thr Glu Thr Pro Asn Ser Glu Phe
        195                 200                 205

Leu Gln Ala Leu His Pro Asp Pro Ser Lys Thr Pro His Pro Glu Ser
    210                 215                 220

His Val Thr His Asn Pro Ser Pro Thr Glu Ile Ser Gln Thr Glu Phe
225                 230                 235                 240

Pro Thr Thr Tyr Tyr Gln Asn Ala Thr Asp Val Pro Arg Thr Ser Asp
                245                 250                 255

Pro Gln Ile Ser Thr Ser Leu Tyr Pro Glu Thr Pro Val Pro Phe Lys
            260                 265                 270

Asp Asp Ala Thr Ala Leu Asn Glu Leu Ser Leu Asn Pro Lys Pro Gly
        275                 280                 285

Thr Pro Ala Ala Ile Gln Pro Asp Ser Pro Lys Leu Pro Thr Ser Asp
    290                 295                 300

Ser Pro Gly Met Val Glu Leu Lys Ala Pro Gln Asn Ser Gly Pro Lys
305                 310                 315                 320

Glu Ser Asn Val Pro Pro Ser Ala Arg Ile Ala Gly Pro Pro Ala
                325                 330                 335

Leu Pro Gly Arg Pro Ser Gln Leu Ala Pro Ala Thr Leu Arg Ala Pro
            340                 345                 350
```

Gln Arg His Ser Arg Gly Glu Gly Val Asn Thr Ile Ile Val Val Glu
          355                 360                 365

Arg Val Lys Glu Thr Gly
    370

<210> SEQ ID NO 11
<211> LENGTH: 1491
<212> TYPE: DNA
<213> ORGANISM: Homo sapiens

<400> SEQUENCE: 11

```
gctccctcag cccctctgcc tttgggctgt ggctttccgg acatggccca cccctctgag      60
acttcccctc tgaagggtgc ttctgaaaat tccaaacgag atcgccttaa cccagaattt     120
cctgggactc cttaccctga gccttccaag ctacctcata cggtttccct ggaaaccttc     180
ccacttgact tcactgagcc cctcaaccct gacctccgag aaaccccgca cccagagtct     240
cctgagaccc ccaaagctga ctcactcaca acctcaatat cagaatccct ggacatgccc     300
aaaactaacc tctccaaaat ggcacaccca gagtcttctg accccccac acctggccca     360
actgaaatgc cacacccagg atccctgag accccaaac ctaacttctc caaaacttca     420
cgcccagaat tcctgagac cccaaacact gaccttatgc aaactacacc ccaagaatcc     480
ccagagattc tgcagcttaa tgccactgaa gtctcacagg cagaactccc cgagacctca     540
aacactaacc ctaccaagac ccctgacccc aaatcccag aaaagcatga cctcaactcc     600
actgagaccc caaactctga atttctccaa gctctccatc ctgacccttc taaaaccccc     660
cacccagaat cccatgtgac ccacaatccc agccccaccg aaatttccca acagaattc     720
cccacaacct actaccaaaa tgcaacagat gtacccagga cctccgaccc tcaaatctcc     780
actagtctct acccagaaac acctgtgccc ttcaaggatg acgccactgc tctaaatgag     840
ctgtccctga tcccaaacc aggaacacct gcagccatcc agcccgactc ccaaaaattg     900
cccacttcag attctccagg aatggttgag ctgaaggccc ccagaactc tggccctaag     960
gagtccaacg tccctcctcc ctcagcccgg attgcaggtc ccctgctct tccagggcgc    1020
cccagtcagt tggcccctgc cactctgcgg gcaccccaga ggcacagccg aggtgaggga    1080
gtcaacacca tcatcgtggt ggagcgagtg aaggagaccg gcgtgactct ggtggggcga    1140
ccacgtggcg cagcaggcgg ggccctctgc ctgttcttcg cggggaccgc gctgctgatc    1200
ggcatctttg tgctgctgtg tgtctttac cgccgggcag ctagacagcg gcccttcgca    1260
catcaccggc ttccggacga cggagatgaa ccggttctgc atttggacgc cccgaaagac    1320
ccctacgacc tctactttta tgctccggat acctgggtcc cttccacat cgccaccaag    1380
cagcccccgc ccacacctcc tctgccacca aagctgcccc cgccgcccg cggggtcgc    1440
ccgcagcgtc tggaggccct gtccccgcc acgctcccca caacttcgt g              1491
```

<210> SEQ ID NO 12
<211> LENGTH: 497
<212> TYPE: PRT
<213> ORGANISM: Homo sapiens

<400> SEQUENCE: 12

Ala Pro Ser Ala Pro Leu Pro Leu Gly Cys Gly Phe Pro Asp Met Ala
1               5                   10                  15

His Pro Ser Glu Thr Ser Pro Leu Lys Gly Ala Ser Glu Asn Ser Lys
            20                  25                  30

Arg Asp Arg Leu Asn Pro Glu Phe Pro Gly Thr Pro Tyr Pro Glu Pro

-continued

```
                35                  40                  45
Ser Lys Leu Pro His Thr Val Ser Leu Glu Thr Phe Pro Leu Asp Phe
 50                  55                  60
Thr Glu Pro Leu Asn Pro Asp Leu Arg Glu Thr Pro His Pro Glu Ser
 65                  70                  75                  80
Pro Glu Thr Pro Lys Ala Asp Ser Leu Thr Thr Ser Ile Ser Glu Ser
                 85                  90                  95
Leu Asp Met Pro Lys Thr Asn Leu Ser Lys Met Ala His Pro Glu Ser
                100                 105                 110
Ser Glu Thr Pro Thr Pro Gly Pro Thr Glu Met Pro His Pro Gly Ser
                115                 120                 125
Pro Glu Thr Pro Lys Pro Asn Phe Ser Lys Ser Arg Pro Glu Phe
                130                 135                 140
Pro Glu Thr Pro Asn Thr Asp Leu Met Gln Thr Pro Gln Glu Ser
145                 150                 155                 160
Pro Glu Ile Leu Gln Leu Asn Ala Thr Glu Val Ser Gln Ala Glu Leu
                165                 170                 175
Pro Glu Thr Ser Asn Thr Asn Pro Thr Lys Thr Pro Asp Pro Lys Ser
                180                 185                 190
Pro Glu Lys His Asp Leu Asn Ser Thr Glu Thr Pro Asn Ser Glu Phe
                195                 200                 205
Leu Gln Ala Leu His Pro Asp Pro Ser Lys Thr Pro His Pro Glu Ser
                210                 215                 220
His Val Thr His Asn Pro Ser Pro Thr Glu Ile Ser Gln Thr Glu Phe
225                 230                 235                 240
Pro Thr Thr Tyr Tyr Gln Asn Ala Thr Asp Val Pro Arg Thr Ser Asp
                245                 250                 255
Pro Gln Ile Ser Thr Ser Leu Tyr Pro Glu Thr Pro Val Pro Phe Lys
                260                 265                 270
Asp Asp Ala Thr Ala Leu Asn Glu Leu Ser Leu Asn Pro Lys Pro Gly
                275                 280                 285
Thr Pro Ala Ala Ile Gln Pro Asp Ser Pro Lys Leu Pro Thr Ser Asp
                290                 295                 300
Ser Pro Gly Met Val Glu Leu Lys Ala Pro Gln Asn Ser Gly Pro Lys
305                 310                 315                 320
Glu Ser Asn Val Pro Pro Ser Ala Arg Ile Ala Gly Pro Pro Ala
                325                 330                 335
Leu Pro Gly Arg Pro Ser Gln Leu Ala Pro Ala Thr Leu Arg Ala Pro
                340                 345                 350
Gln Arg His Ser Arg Gly Glu Gly Val Asn Thr Ile Ile Val Val Glu
                355                 360                 365
Arg Val Lys Glu Thr Gly Val Thr Leu Val Gly Arg Pro Arg Gly Ala
                370                 375                 380
Ala Gly Gly Ala Leu Cys Leu Phe Phe Ala Gly Thr Ala Leu Leu Ile
385                 390                 395                 400
Gly Ile Phe Val Leu Leu Trp Cys Leu Tyr Arg Arg Ala Ala Arg Gln
                405                 410                 415
Arg Pro Phe Ala His His Arg Leu Pro Asp Asp Gly Asp Glu Pro Val
                420                 425                 430
Leu His Leu Asp Ala Pro Lys Asp Pro Tyr Asp Leu Tyr Phe Tyr Ala
                435                 440                 445
Pro Asp Thr Trp Val Pro Ser His Ile Ala Thr Lys Gln Pro Pro Pro
                450                 455                 460
```

```
Thr Pro Pro Leu Pro Pro Lys Leu Pro Pro Pro Arg Gly Gly Arg
465                 470                 475                 480

Pro Gln Arg Leu Glu Ala Leu Ser Pro Ala Thr Leu Pro Asn Asn Phe
            485                 490                 495

Val
```

<210> SEQ ID NO 13
<211> LENGTH: 1215
<212> TYPE: DNA
<213> ORGANISM: Homo sapiens

<400> SEQUENCE: 13

```
atgaaatcat tcagccggat cctcttcctc gtcttcctcc tcgccggcct gaggtccaag      60
gccgctccct cagccctct  gcctttgggc tgtggctttc ggacatggc  ccacccctct    120
gagacttccc ctctgaaggg tgcttctgaa aattccaaac gagatcgcct taacccagaa    180
tttcctggga ctccttaccc tgagccttcc aagctacctc atacggtttc ctggaaaacc    240
ttcccacttg acttcactga gcccctcaac cctgacctcc gagaaacccc gcacccagag    300
tctcctgaga cccccaaagc tgactcactc acaacctcaa tatcagaatc cctggacatg    360
cccaaaacta acctctccaa aatggcacac ccagagtctt ctgagacccc cacacctggc    420
ccaactgaaa tgccacaccc aggatcccct gagaccccca acctaacttc tccaaaaact    480
tcacgcccag aatttcctga ccccaaac   actgaccttta tgcaaactac accccaagaa    540
tccccagaga ttctgcagct taatgccact gaagtctcac aggcagaact ccccgagacc    600
tcaaacacta accctaccaa gaccccctgac cccaaatccc cagaaaagca tgacctcaac    660
tccactgaga ccccaaactc tgaatttctc caagctctcc atcctgaccc ttctaaaacc    720
ccccacccag aatcccatgt gacccacaat cccagcccca ccgaaatttc ccaaacagaa    780
ttccccacaa cctactacca aaatgcaaca gatgtaccca ggacctccga ccctcaaatc    840
tccactagtc tctacccaga aacacctgtg cccttcaagg atgacgccac tgctctaaat    900
gagctgtccc tgaatcccaa accaggaaca cctgcagcca tccagcccga ctccccaaaa    960
ttgcccactt cagattctcc aggaatggtt gagctgaagg ccccccagaa ctctggccct   1020
aaggagtcca acgtccctcc tccctcagcc cggattgcag gtccccctgc tcttccaggg   1080
cgccccagtc agttggcccc tgccactctg cgggcacccc agaggcacag ccgaggtgag   1140
ggagtcaaca ccatcatcgt ggtggagcga gtgaaggaga ccggcgtgac tctggtgggg   1200
cgaccacgtg gcgca                                                     1215
```

<210> SEQ ID NO 14
<211> LENGTH: 405
<212> TYPE: PRT
<213> ORGANISM: Homo sapiens

<400> SEQUENCE: 14

```
Met Lys Ser Phe Ser Arg Ile Leu Phe Leu Val Phe Leu Leu Ala Gly
1               5                   10                  15

Leu Arg Ser Lys Ala Ala Pro Ser Ala Pro Leu Pro Leu Gly Cys Gly
            20                  25                  30

Phe Pro Asp Met Ala His Pro Ser Glu Thr Ser Pro Leu Lys Gly Ala
            35                  40                  45

Ser Glu Asn Ser Lys Arg Asp Arg Leu Asn Pro Glu Phe Pro Gly Thr
    50                  55                  60

Pro Tyr Pro Glu Pro Ser Lys Leu Pro His Thr Val Ser Leu Glu Thr
65                  70                  75                  80
```

Phe Pro Leu Asp Phe Thr Glu Pro Leu Asn Pro Asp Leu Arg Glu Thr
                85                  90                  95

Pro His Pro Glu Ser Pro Glu Thr Pro Lys Ala Asp Ser Leu Thr Thr
            100                 105                 110

Ser Ile Ser Glu Ser Leu Asp Met Pro Lys Thr Asn Leu Ser Lys Met
        115                 120                 125

Ala His Pro Glu Ser Ser Glu Thr Pro Thr Pro Gly Pro Thr Glu Met
130                 135                 140

Pro His Pro Gly Ser Pro Glu Thr Pro Lys Pro Asn Phe Ser Lys Thr
145                 150                 155                 160

Ser Arg Pro Glu Phe Pro Glu Thr Pro Asn Thr Asp Leu Met Gln Thr
                165                 170                 175

Thr Pro Gln Glu Ser Pro Glu Ile Leu Gln Leu Asn Ala Thr Glu Val
            180                 185                 190

Ser Gln Ala Glu Leu Pro Glu Thr Ser Asn Thr Asn Pro Thr Lys Thr
        195                 200                 205

Pro Asp Pro Lys Ser Pro Glu Lys His Asp Leu Asn Ser Thr Glu Thr
210                 215                 220

Pro Asn Ser Glu Phe Leu Gln Ala Leu His Pro Asp Pro Ser Lys Thr
225                 230                 235                 240

Pro His Pro Glu Ser His Val Thr His Asn Pro Ser Pro Thr Glu Ile
                245                 250                 255

Ser Gln Thr Glu Phe Pro Thr Thr Tyr Tyr Gln Asn Ala Thr Asp Val
            260                 265                 270

Pro Arg Thr Ser Asp Pro Gln Ile Ser Thr Ser Leu Tyr Pro Glu Thr
        275                 280                 285

Pro Val Pro Phe Lys Asp Asp Ala Thr Ala Leu Asn Glu Leu Ser Leu
290                 295                 300

Asn Pro Lys Pro Gly Thr Pro Ala Ala Ile Gln Pro Asp Ser Pro Lys
305                 310                 315                 320

Leu Pro Thr Ser Asp Ser Pro Gly Met Val Glu Leu Lys Ala Pro Gln
                325                 330                 335

Asn Ser Gly Pro Lys Glu Ser Asn Val Pro Pro Ser Ala Arg Ile
            340                 345                 350

Ala Gly Pro Pro Ala Leu Pro Gly Arg Pro Ser Gln Leu Ala Pro Ala
        355                 360                 365

Thr Leu Arg Ala Pro Gln Arg His Ser Arg Gly Glu Gly Val Asn Thr
370                 375                 380

Ile Ile Val Val Glu Arg Val Lys Glu Thr Gly Val Thr Leu Val Gly
385                 390                 395                 400

Arg Pro Arg Gly Ala
            405

<210> SEQ ID NO 15
<211> LENGTH: 270
<212> TYPE: DNA
<213> ORGANISM: Homo sapiens

<400> SEQUENCE: 15
tgtctttacc gccgggcagc tagacagcgg cccttcgcac atcaccggct tccggacgac   60
ggagatgaac cggttctgca tttggacgcc ccgaaagacc cctacgacct ctactttat  120 gctccggata cctgggtccc ttcccacatc gccaccaagc agcccccgcc cacacctcct  180
ctgccaccaa agctgccccc gccgcccgc ggggtcgcc cgcagcgtct ggaggccctg   240
tcccccgcca cgctccccaa caacttcgtg                                            270

<210> SEQ ID NO 16
<211> LENGTH: 90
<212> TYPE: PRT
<213> ORGANISM: Homo sapiens

<400> SEQUENCE: 16

Cys Leu Tyr Arg Arg Ala Ala Arg Gln Arg Pro Phe Ala His His Arg
 1               5                  10                  15

Leu Pro Asp Asp Gly Asp Glu Pro Val Leu His Leu Asp Ala Pro Lys
            20                  25                  30

Asp Pro Tyr Asp Leu Tyr Phe Tyr Ala Pro Asp Thr Trp Val Pro Ser
        35                  40                  45

His Ile Ala Thr Lys Gln Pro Pro Thr Pro Leu Pro Pro Lys
50                  55                  60

Leu Pro Pro Pro Arg Gly Gly Arg Pro Gln Arg Leu Glu Ala Leu
65                  70                  75                  80

Ser Pro Ala Thr Leu Pro Asn Asn Phe Val
            85                  90

<210> SEQ ID NO 17
<211> LENGTH: 1152
<212> TYPE: DNA
<213> ORGANISM: Homo sapiens

<400> SEQUENCE: 17
gctccctcag cccctctgcc tttgggctgt ggctttccgg acatggccca ccctctgag       60
acttcccctc tgaagggtgc ttctgaaaat tccaaacgag atcgccttaa cccagaattt      120
cctgggactc cttaccctga gccttccaag ctacctcata cggtttccct ggaaaccttc      180
ccacttgact tcactgagcc cctcaaccct gacctcgag aaaccccgca cccagagtct       240
cctgagaccc ccaaagctga ctcactcaca acctcaatat cagaatccct ggacatgccc      300
aaaactaacc tctccaaaat ggcacaccca gagtcttctg agaccccccac acctggccca    360
actgaaatgc cacacccagg atccctgag acccccaaac ctaacttctc caaaacttca      420
cgcccagaat tcctgagac cccaaacact gaccttatgc aaactacacc ccaagaatcc      480
ccagagattc tgcagcttaa tgccactgaa gtctcacagg cagaactccc cgagacctca    540
aacactaacc ctaccaagac ccctgacccc aaatcccag aaaagcatga cctcaactcc     600
actgagaccc caaactctga atttctccaa gctctccatc ctgacccttc taaaacccc     660
cacccagaat cccatgtgac ccacaatccc agccccaccg aaatttccca aacagaattc     720
cccacaacct actaccaaaa tgcaacagat gtacccagga cctccgaccc tcaaatctcc     780
actagtctct acccagaaac acctgtgccc ttcaaggatg acgccactgc tctaaatgag      840
ctgtccctga tcccaaaacc aggaacacct gcagccatcc agcccgactc cccaaaattg     900
cccacttcag attctccagg aatggttgag ctgaaggccc ccagaactc tggccctaag     960
gagtccaacg tcctcctcc ctcagccggg attgcaggtc ccctgctctt ccagggcgc     1020
cccagtcagt tggcccctgc cactctgcgg gcaccccaga ggcacagccg aggtgaggga   1080
gtcaacacca tcatcgtggt ggagcgagtg aaggagaccg gcgtgactct ggtggggcga   1140
ccacgtggcg ca                                                         1152

<210> SEQ ID NO 18
<211> LENGTH: 384
<212> TYPE: PRT

<213> ORGANISM: Homo sapiens

<400> SEQUENCE: 18

```
Ala Pro Ser Ala Pro Leu Pro Leu Gly Cys Gly Phe Pro Asp Met Ala
1               5                   10                  15

His Pro Ser Glu Thr Ser Pro Leu Lys Gly Ala Ser Glu Asn Ser Lys
            20                  25                  30

Arg Asp Arg Leu Asn Pro Glu Phe Pro Gly Thr Pro Tyr Pro Glu Pro
        35                  40                  45

Ser Lys Leu Pro His Thr Val Ser Leu Glu Thr Phe Pro Leu Asp Phe
    50                  55                  60

Thr Glu Pro Leu Asn Pro Asp Leu Arg Glu Thr His Pro Glu Ser
65              70                  75                  80

Pro Glu Thr Pro Lys Ala Asp Ser Leu Thr Thr Ser Ile Ser Glu Ser
                85                  90                  95

Leu Asp Met Pro Lys Thr Asn Leu Ser Lys Met Ala His Pro Glu Ser
            100                 105                 110

Ser Glu Thr Pro Thr Pro Gly Pro Thr Glu Met Pro His Pro Gly Ser
        115                 120                 125

Pro Glu Thr Pro Lys Pro Asn Phe Ser Lys Thr Ser Arg Pro Glu Phe
130                 135                 140

Pro Glu Thr Pro Asn Thr Asp Leu Met Gln Thr Thr Pro Gln Glu Ser
145                 150                 155                 160

Pro Glu Ile Leu Gln Leu Asn Ala Thr Glu Val Ser Gln Ala Glu Leu
                165                 170                 175

Pro Glu Thr Ser Asn Thr Asn Pro Thr Lys Thr Pro Asp Pro Lys Ser
            180                 185                 190

Pro Glu Lys His Asp Leu Asn Ser Thr Glu Thr Pro Asn Ser Glu Phe
        195                 200                 205

Leu Gln Ala Leu His Pro Asp Pro Ser Lys Thr Pro His Pro Glu Ser
    210                 215                 220

His Val Thr His Asn Pro Ser Pro Glu Ile Ser Gln Thr Glu Phe
225                 230                 235                 240

Pro Thr Thr Tyr Tyr Gln Asn Ala Thr Asp Val Pro Arg Thr Ser Asp
                245                 250                 255

Pro Gln Ile Ser Thr Ser Leu Tyr Pro Glu Thr Pro Val Pro Phe Lys
            260                 265                 270

Asp Asp Ala Thr Ala Leu Asn Glu Leu Ser Leu Asn Pro Lys Pro Gly
        275                 280                 285

Thr Pro Ala Ala Ile Gln Pro Asp Ser Pro Lys Leu Pro Thr Ser Asp
    290                 295                 300

Ser Pro Gly Met Val Glu Leu Lys Ala Pro Gln Asn Ser Gly Pro Lys
305                 310                 315                 320

Glu Ser Asn Val Pro Pro Pro Ser Ala Arg Ile Ala Gly Pro Ala
                325                 330                 335

Leu Pro Gly Arg Pro Ser Gln Leu Ala Pro Ala Thr Leu Arg Ala Pro
            340                 345                 350

Gln Arg His Ser Arg Gly Glu Gly Val Asn Thr Ile Ile Val Val Glu
        355                 360                 365

Arg Val Lys Glu Thr Gly Val Thr Leu Val Gly Arg Pro Arg Gly Ala
    370                 375                 380
```

<210> SEQ ID NO 19
<211> LENGTH: 1183
<212> TYPE: DNA

<213> ORGANISM: Homo sapiens

<400> SEQUENCE: 19

```
atgaaatcat tcagccggat cctcttcctc gtcttcctcc tcgccggcct gaggtccaag    60
gccgctccct cagcccctct gcctttgggc tgtggctttc cggacatggc ccacccctct   120
gagacttccc ctctgaaggg tgcttctgaa aattccaaac gagatcgcct taacccagaa   180
tttcctggga ctccttaccc tgagccttcc aagctacctc atacggtttc cctggaaacc   240
ttcccacttg acttcactga ccccctcaac cctgacctcc gagaaacccc gcacccagag   300
tctcctgaga cccccaaagc tgactcactc acaacctcaa tatcagaatc cctggacatg   360
cccaaaacta acctctccaa aatggcacac ccagagtctt ctgagacccc cacacctggc   420
ccaactgaaa tgccacaccc aggatcccct gagaccccca aacctaactt ctccaaaact   480
tcacgcccag aatttcctga cccccaaaac actgacctta tgcaaactac accccaagaa   540
tccccagaga ttctgcagct taatgccact gaagtctcac aggcagaact ccccgagacc   600
tcaaacacta accctaccaa gacccctgac cccaaatccc agaaaagca tgacctcaac   660
tccactgaga ccccaaactc tgaatttctc caagctctcc atcctgaccc ttctaaaacc   720
ccccacccag aatcccatgt gacccacaat cccagcccca ccgaaatttc ccaaacagaa   780
ttccccacaa cctactacca aaatgcaaca gatgtaccca ggacctccga ccctcaaatc   840
tccactagtc tctacccaga aacacctgtg cccttcaagg atgacgccac tgctctaaat   900
gagctgtccc tgaatcccaa accaggaaca cctgcagcca tccagcccga ctccccaaaa   960
ttgcccactt cagattctcc aggaatggtt gagctgaagg cccccccagaa ctctggccct  1020
aaggagtcca cgcccctcc tccctcagcc cggattgcag gtccccctgc tcttccaggg  1080
cgccccagtc agttggcccc tgccactctg cgggcacccc agaggcacag ccgaggtgag  1140
ggagtcaaca ccatcatcgt ggtggagcga gtgaaggaga ccg                     1183
```

<210> SEQ ID NO 20
<211> LENGTH: 395
<212> TYPE: PRT
<213> ORGANISM: Homo sapiens

<400> SEQUENCE: 20

```
Met Lys Ser Phe Ser Arg Ile Leu Phe Leu Val Phe Leu Leu Ala Gly
1               5                   10                  15

Leu Arg Ser Lys Ala Ala Pro Ser Ala Pro Leu Pro Leu Gly Cys Gly
            20                  25                  30

Phe Pro Asp Met Ala His Pro Ser Glu Thr Ser Pro Leu Lys Gly Ala
        35                  40                  45

Ser Glu Asn Ser Lys Arg Asp Arg Leu Asn Pro Glu Phe Pro Gly Thr
    50                  55                  60

Pro Tyr Pro Glu Pro Ser Lys Leu Pro His Thr Val Ser Leu Glu Thr
65                  70                  75                  80

Phe Pro Leu Asp Phe Thr Glu Pro Leu Asn Pro Asp Leu Arg Glu Thr
                85                  90                  95

Pro His Pro Glu Ser Pro Glu Thr Pro Lys Ala Asp Ser Leu Thr Thr
            100                 105                 110

Ser Ile Ser Glu Ser Leu Asp Met Pro Lys Thr Asn Leu Ser Lys Met
        115                 120                 125

Ala His Pro Glu Ser Ser Glu Thr Pro Thr Pro Gly Pro Thr Glu Met
    130                 135                 140

Pro His Pro Gly Ser Pro Glu Thr Pro Lys Pro Asn Phe Ser Lys Thr
```

```
            145                 150                 155                 160
Ser Arg Pro Glu Phe Pro Glu Thr Pro Asn Thr Asp Leu Met Gln Thr
                    165                 170                 175

Thr Pro Gln Glu Ser Pro Glu Ile Leu Gln Leu Asn Ala Thr Glu Val
                180                 185                 190

Ser Gln Ala Glu Leu Pro Glu Thr Ser Asn Thr Asn Pro Thr Lys Thr
            195                 200                 205

Pro Asp Pro Lys Ser Pro Glu Lys His Asp Leu Asn Ser Thr Glu Thr
        210                 215                 220

Pro Asn Ser Glu Phe Leu Gln Ala Leu His Pro Asp Pro Ser Lys Thr
225                 230                 235                 240

Pro His Pro Glu Ser His Val Thr His Asn Pro Ser Pro Thr Glu Ile
                245                 250                 255

Ser Gln Thr Glu Phe Pro Thr Thr Tyr Tyr Gln Asn Ala Thr Asp Val
                260                 265                 270

Pro Arg Thr Ser Asp Pro Gln Ile Ser Thr Ser Leu Tyr Pro Glu Thr
                275                 280                 285

Pro Val Pro Phe Lys Asp Asp Ala Thr Ala Leu Asn Glu Leu Ser Leu
            290                 295                 300

Asn Pro Lys Pro Gly Thr Pro Ala Ala Ile Gln Pro Asp Ser Pro Lys
305                 310                 315                 320

Leu Pro Thr Ser Asp Ser Pro Gly Met Val Glu Leu Lys Ala Pro Gln
                325                 330                 335

Asn Ser Gly Pro Lys Glu Ser Asn Ala Pro Pro Ser Ala Arg Ile
                340                 345                 350

Ala Gly Pro Pro Ala Leu Pro Gly Arg Pro Ser Gln Leu Ala Pro Ala
            355                 360                 365

Thr Leu Arg Ala Pro Gln Arg His Ser Arg Gly Glu Gly Val Asn Thr
        370                 375                 380

Ile Ile Val Val Glu Arg Val Lys Glu Thr Gly
385                 390                 395

<210> SEQ ID NO 21
<211> LENGTH: 1215
<212> TYPE: DNA
<213> ORGANISM: Homo sapiens

<400> SEQUENCE: 21
atgaaatcat tcagccggat cctcttcctc gtcttcctcc tcgccggcct gaggtccaag      60
gccgctccct cagcccctct gcctttgggc tgtggctttc cggacatggc ccacccctct     120
gagacttccc ctctgaaggg tgcttctgaa aattccaaac gagatcgcct taacccagaa     180
tttcctggga ctccttaccc tgagccttcc aagctacctc atacggtttc cctggaaacc     240
ttcccacttg acttcactga ccccctcaac cctgacctcc gagaaacccc gcacccagag     300
tctcctgaga cccccaaagc tgactcactc acaacctcaa tatcagaatc cctggacatg     360
cccaaaacta acctctccaa aatggcacac cagagtcttc tgagacccca cacctggc      420 ccaactgaaa tgccacaccc aggatcccct gagaccccca acctaacttc tccaaaact     480 tcacgcccag aatttcctga ccccaaaac actgacctta tgcaaactac accccaagaa     540
tccccagaga ttctgcagct taatgccact gaagtctcac aggcagaact ccccgagacc     600
tcaaacacta accctaccaa gaccctgac ccaaatccc cagaaagca tgacctcaac     660 tccactgaga cccaaactc tgaatttctc caagctctcc atcctgaccc ttctaaaacc     720
cccaccccag aatccatgt gacccacaat cccagcccca ccgaaattta ccaaacagaa     780
```

```
ttccccacaa cctactacca aaatgcaaca gatgtaccca ggacctccga ccctcaaatc    840
tccactagtc tctacccaga aacacctgtg cccttcaagg atgacgccac tgctctaaat    900
gagctgtccc tgaatcccaa accaggaaca cctgcagcca tccagcccga ctccccaaaa    960
ttgcccactt cagattctcc aggaatggtt gagctgaagg ccccccagaa ctctggccct   1020
aaggagtcca acgccctcc tccctcagcc cggattgcag gtcccctgc tcttccaggg     1080 cgccccagtc agttggcccc tgccactctg cgggcacccc agaggcacag ccgaggtgag   1140
ggagtcaaca ccatcatcgt ggtggagcga gtgaaggaga ccggcgtgac tctggtgggg   1200
cgaccacgtg gcgca                                                    1215
```

<210> SEQ ID NO 22
<211> LENGTH: 405
<212> TYPE: PRT
<213> ORGANISM: Homo sapiens

<400> SEQUENCE: 22

```
Met Lys Ser Phe Ser Arg Ile Leu Phe Leu Val Phe Leu Leu Ala Gly
1               5                   10                  15

Leu Arg Ser Lys Ala Ala Pro Ser Ala Pro Leu Pro Leu Gly Cys Gly
                20                  25                  30

Phe Pro Asp Met Ala His Pro Ser Glu Thr Ser Pro Leu Lys Gly Ala
            35                  40                  45

Ser Glu Asn Ser Lys Arg Asp Arg Leu Asn Pro Glu Phe Pro Gly Thr
        50                  55                  60

Pro Tyr Pro Glu Pro Ser Lys Leu Pro His Thr Val Ser Leu Glu Thr
65                  70                  75                  80

Phe Pro Leu Asp Phe Thr Glu Pro Leu Asn Pro Asp Leu Arg Glu Thr
                85                  90                  95

Pro His Pro Glu Ser Pro Glu Thr Pro Lys Ala Asp Ser Leu Thr Thr
            100                 105                 110

Ser Ile Ser Glu Ser Leu Asp Met Pro Lys Thr Asn Leu Ser Lys Met
        115                 120                 125

Ala His Pro Glu Ser Ser Glu Thr Pro Thr Pro Gly Pro Thr Glu Met
    130                 135                 140

Pro His Pro Gly Ser Pro Glu Thr Pro Lys Pro Asn Phe Ser Lys Thr
145                 150                 155                 160

Ser Arg Pro Glu Phe Pro Glu Thr Pro Asn Thr Asp Leu Met Gln Thr
                165                 170                 175

Thr Pro Gln Glu Ser Pro Glu Ile Leu Gln Leu Asn Ala Thr Glu Val
            180                 185                 190

Ser Gln Ala Glu Leu Pro Glu Thr Ser Asn Thr Asn Pro Thr Lys Thr
        195                 200                 205

Pro Asp Pro Lys Ser Pro Glu Lys His Asp Leu Asn Ser Thr Glu Thr
    210                 215                 220

Pro Asn Ser Glu Phe Leu Gln Ala Leu His Pro Asp Pro Ser Lys Thr
225                 230                 235                 240

Pro His Pro Glu Ser His Val Thr His Asn Pro Ser Pro Thr Glu Ile
                245                 250                 255

Ser Gln Thr Glu Phe Pro Thr Thr Tyr Tyr Gln Asn Ala Thr Asp Val
            260                 265                 270

Pro Arg Thr Ser Asp Pro Gln Ile Ser Thr Ser Leu Tyr Pro Glu Thr
        275                 280                 285

Pro Val Pro Phe Lys Asp Asp Ala Thr Ala Leu Asn Glu Leu Ser Leu
```

```
                290                 295                 300
Asn Pro Lys Pro Gly Thr Pro Ala Ala Ile Gln Pro Asp Ser Pro Lys
305                 310                 315                 320

Leu Pro Thr Ser Asp Ser Pro Gly Met Val Glu Leu Lys Ala Pro Gln
                325                 330                 335

Asn Ser Gly Pro Lys Glu Ser Asn Ala Pro Pro Ser Ala Arg Ile
                340                 345                 350

Ala Gly Pro Pro Ala Leu Pro Gly Arg Pro Ser Gln Leu Ala Pro Ala
                355                 360                 365

Thr Leu Arg Ala Pro Gln Arg His Ser Arg Gly Glu Gly Val Asn Thr
        370                 375                 380

Ile Ile Val Val Glu Arg Val Lys Glu Thr Gly Val Thr Leu Val Gly
385                 390                 395                 400

Arg Pro Arg Gly Ala
                405

<210> SEQ ID NO 23
<211> LENGTH: 1554
<212> TYPE: DNA
<213> ORGANISM: Homo sapiens

<400> SEQUENCE: 23
atgaaatcat tcagccggat cctcttcctc gtcttcctcc tcgccggcct gaggtccaag      60
gccgctccct cagcccctct gcctttgggc tgtggctttc cggacatggc ccaccccctct    120 gagacttccc ctctgaaggg tgcttctgaa aattccaaac gagatcgcct taacccagaa     180
tttcctggga ctccttaccc tgagccttcc aagctacctc atacggtttc cctggaaacc     240
ttcccacttg acttcactga gcccctcaac cctgacctcc gagaaacccc gcacccagag     300
tctcctgaga cccccaaagc tgactcactc acaacctcaa tatcagaatc cctggacatg     360
cccaaaacta acctctccaa aatggcacac cagagtcttc tgagacccca cacctggc      420 ccaactgaaa tgccacaccc aggatcccct gagaccccca acctaacttt ctccaaaact     480
tcacgcccag aatttcctga ccccaaac actgaccta gcaaactac acccaagaa         540 tccccagaga ttctgcagct taatgccact gaagtctcac aggcagaact ccccgagacc     600
tcaaacacta accctaccaa gaccctgac cccaaatccc cagaaaagca tgacctcaac      660
tccactgaga ccccaaactc tgaatttctc caagctctcc atcctgaccc ttctaaaacc     720
ccccacccag aatcccatgt gacccacaat cccagccca cgaaatttc ccaaacagaa       780 ttccccacaa cctactacca aaatgcaaca gatgtaccca ggacctccga ccctcaaatc     840
tccactagtc tctacccaga aacacctgtg cccttcaagg atgacgccac tgctctaaat     900
gagctgtccc tgaatcccaa accaggaaca cctgcagcca tccagcccga ctccccaaaa     960
ttgcccactt cagattctcc aggaatggtt gagctgaagg cccccagaa ctctggccct    1020 aaggagtcca acgcccctcc tccctcagcc cggattgcag gtccccctgc tcttccaggg   1080
cgccccagtc agttggcccc tgccactctg cgggcacccc agaggcacag ccgaggtgag   1140
ggagtcaaca ccatcatcgt ggtggagcga gtgaaggaga ccggcgtgac tctggtgggg   1200
cgaccacgtg gcgcagcagg cggggccctc tgcctgttct tcgcggggac cgcgctgctg   1260
atcggcatct ttgtgctgct gtggtgtctt taccgccggg cagctagaca gcggcccttc   1320
gcacatcacc ggcttccgga cgacggagat gaaccggttc tgcatttgga cgccccgaaa   1380
gacccctacg acctctactt ttatgctccg gataccctggg tccttcccca catcgccacc   1440
aagcagcccc cgcccacacc tcctctgcca ccaaagctgc ccccgccgcc ccgcggggt    1500
```
cgcccgcagc gtctggaggc cctgtccccc gccacgctcc ccaacaactt cgtg    1554

<210> SEQ ID NO 24
<211> LENGTH: 518
<212> TYPE: PRT
<213> ORGANISM: Homo sapiens

<400> SEQUENCE: 24

Met Lys Ser Phe Ser Arg Ile Leu Phe Leu Val Phe Leu Leu Ala Gly
1               5                   10                  15

Leu Arg Ser Lys Ala Ala Pro Ser Ala Pro Leu Pro Leu Gly Cys Gly
            20                  25                  30

Phe Pro Asp Met Ala His Pro Ser Glu Thr Ser Pro Leu Lys Gly Ala
        35                  40                  45

Ser Glu Asn Ser Lys Arg Asp Arg Leu Asn Pro Glu Phe Pro Gly Thr
    50                  55                  60

Pro Tyr Pro Glu Pro Ser Lys Leu Pro His Thr Val Ser Leu Glu Thr
65                  70                  75                  80

Phe Pro Leu Asp Phe Thr Glu Pro Leu Asn Pro Asp Leu Arg Glu Thr
                85                  90                  95

Pro His Pro Glu Ser Pro Glu Thr Pro Lys Ala Asp Ser Leu Thr Thr
            100                 105                 110

Ser Ile Ser Glu Ser Leu Asp Met Pro Lys Thr Asn Leu Ser Lys Met
        115                 120                 125

Ala His Pro Glu Ser Ser Glu Thr Pro Thr Pro Gly Pro Thr Glu Met
    130                 135                 140

Pro His Pro Gly Ser Pro Glu Thr Pro Lys Pro Asn Phe Ser Lys Thr
145                 150                 155                 160

Ser Arg Pro Glu Phe Pro Glu Thr Pro Asn Thr Asp Leu Met Gln Thr
                165                 170                 175

Thr Pro Gln Glu Ser Pro Glu Ile Leu Gln Leu Asn Ala Thr Glu Val
            180                 185                 190

Ser Gln Ala Glu Leu Pro Glu Thr Ser Asn Thr Asn Pro Thr Lys Thr
        195                 200                 205

Pro Asp Pro Lys Ser Pro Glu Lys His Asp Leu Asn Ser Thr Glu Thr
    210                 215                 220

Pro Asn Ser Glu Phe Leu Gln Ala Leu His Pro Asp Pro Ser Lys Thr
225                 230                 235                 240

Pro His Pro Glu Ser His Val Thr His Asn Pro Ser Pro Thr Glu Ile
                245                 250                 255

Ser Gln Thr Glu Phe Pro Thr Thr Tyr Tyr Gln Asn Ala Thr Asp Val
            260                 265                 270

Pro Arg Thr Ser Asp Pro Gln Ile Ser Thr Ser Leu Tyr Pro Glu Thr
        275                 280                 285

Pro Val Pro Phe Lys Asp Asp Ala Thr Ala Leu Asn Glu Leu Ser Leu
    290                 295                 300

Asn Pro Lys Pro Gly Thr Pro Ala Ala Ile Gln Pro Asp Ser Pro Lys
305                 310                 315                 320

Leu Pro Thr Ser Asp Ser Pro Gly Met Val Glu Leu Lys Ala Pro Gln
                325                 330                 335

Asn Ser Gly Pro Lys Glu Ser Asn Ala Pro Pro Ser Ala Arg Ile
            340                 345                 350

Ala Gly Pro Pro Ala Leu Pro Gly Arg Pro Ser Gln Leu Ala Pro Ala
        355                 360                 365

Thr Leu Arg Ala Pro Gln Arg His Ser Arg Gly Glu Gly Val Asn Thr
    370                 375                 380

Ile Ile Val Val Glu Arg Val Lys Glu Thr Gly Val Thr Leu Val Gly
385                 390                 395                 400

Arg Pro Arg Gly Ala Gly Gly Ala Leu Cys Leu Phe Phe Ala Gly
                405                 410                 415

Thr Ala Leu Leu Ile Gly Ile Phe Val Leu Leu Trp Cys Leu Tyr Arg
            420                 425                 430

Arg Ala Ala Arg Gln Arg Pro Phe Ala His His Arg Leu Pro Asp Asp
            435                 440                 445

Gly Asp Glu Pro Val Leu His Leu Asp Ala Pro Lys Asp Pro Tyr Asp
    450                 455                 460

Leu Tyr Phe Tyr Ala Pro Asp Thr Trp Val Pro Ser His Ile Ala Thr
465                 470                 475                 480

Lys Gln Pro Pro Pro Thr Pro Leu Pro Pro Lys Leu Pro Pro Pro
                485                 490                 495

Pro Arg Gly Gly Arg Pro Gln Arg Leu Glu Ala Leu Ser Pro Ala Thr
            500                 505                 510

Leu Pro Asn Asn Phe Val
            515

<210> SEQ ID NO 25
<211> LENGTH: 1120
<212> TYPE: DNA
<213> ORGANISM: Homo sapiens

<400> SEQUENCE: 25

```
gctccctcag cccctctgcc tttgggctgt ggctttccgg acatggccca cccctctgag    60
acttcccctc tgaagggtgc ttctgaaaat tccaaacgag atcgccttaa cccagaattt   120
cctgggactc cttaccctga gcttccaag ctacctcata cggtttccct ggaaaccttc   180
ccacttgact tcactgagcc cctcaaccct gacctccgag aaaccccgca cccagagtct   240
cctgagaccc ccaaagctga ctcactcaca acctcaatat cagaatccct ggacatgccc   300
aaaactaacc tctccaaaat ggcacaccca gagtcttctg agaccccac acctggccca   360
actgaaatgc cacacccagg atccctgag accccaaaac ctaacttctc caaaacttca   420
cgcccagaat ttcctgagac cccaaacact gaccttatgc aaactacacc caagaatcc   480
ccagagattc tgcagcttaa tgccactgaa gtctcacagg cagaactccc cgagacctca   540
aacactaacc ctaccaagac ccctgacccc aaatccccag aaaagcatga cctcaactcc   600
actgagaccc caaactctga atttctccaa gctctccatc ctgacccttc taaaaccccc   660
cacccagaat cccatgtgac ccacaatccc agccccaccg aaatttccca aacagaattc   720
cccacaaacct actaccaaaa tgcaacagat gtacccagga cctccgaccc tcaaatctcc   780
actagtctct acccagaaac acctgtgccc ttcaaggatg acgccactgc tctaaatgag   840
ctgtccctga tcccaaaacc aggaacacct gcagccatcc agcccgactc ccaaaattg   900
cccacttcag attctccagg aatggttgag ctgaaggccc cccagaactc tggccctaag   960
gagtccaacg cccctcctcc ctcagccgg attgcaggtc ccctgctct tccagggcgc  1020
cccagtcagt tggcccctgc cactctgcgg gcacccagaa ggcacagccg aggtgaggga  1080
gtcaacacca tcatcgtggt ggagcgagtg aaggagaccg                         1120
```

<210> SEQ ID NO 26
<211> LENGTH: 374
<212> TYPE: PRT

<213> ORGANISM: Homo sapiens

<400> SEQUENCE: 26

```
Ala Pro Ser Ala Pro Leu Pro Leu Gly Cys Gly Phe Pro Asp Met Ala
 1               5                  10                  15
His Pro Ser Glu Thr Ser Pro Leu Lys Gly Ala Ser Glu Asn Ser Lys
             20                  25                  30
Arg Asp Arg Leu Asn Pro Glu Phe Pro Gly Thr Pro Tyr Pro Glu Pro
         35                  40                  45
Ser Lys Leu Pro His Thr Val Ser Leu Glu Thr Phe Pro Leu Asp Phe
     50                  55                  60
Thr Glu Pro Leu Asn Pro Asp Leu Arg Glu Thr His Pro Glu Ser
 65                  70                  75                  80
Pro Glu Thr Pro Lys Ala Asp Ser Leu Thr Thr Ser Ile Ser Glu Ser
                 85                  90                  95
Leu Asp Met Pro Lys Thr Asn Leu Ser Lys Met Ala His Pro Glu Ser
             100                 105                 110
Ser Glu Thr Pro Thr Pro Gly Pro Thr Glu Met Pro His Pro Gly Ser
         115                 120                 125
Pro Glu Thr Pro Lys Pro Asn Phe Ser Lys Thr Ser Arg Pro Glu Phe
    130                 135                 140
Pro Glu Thr Pro Asn Thr Asp Leu Met Gln Thr Thr Pro Gln Glu Ser
145                 150                 155                 160
Pro Glu Ile Leu Gln Leu Asn Ala Thr Glu Val Ser Gln Ala Glu Leu
                165                 170                 175
Pro Glu Thr Ser Asn Thr Asn Pro Thr Lys Thr Pro Asp Pro Lys Ser
            180                 185                 190
Pro Glu Lys His Asp Leu Asn Ser Thr Glu Thr Pro Asn Ser Glu Phe
        195                 200                 205
Leu Gln Ala Leu His Pro Asp Pro Ser Lys Thr Pro His Pro Glu Ser
    210                 215                 220
His Val Thr His Asn Pro Ser Pro Glu Ile Ser Gln Thr Glu Phe
225                 230                 235                 240
Pro Thr Thr Tyr Tyr Gln Asn Ala Thr Asp Val Pro Arg Thr Ser Asp
                245                 250                 255
Pro Gln Ile Ser Thr Ser Leu Tyr Pro Glu Thr Pro Val Pro Phe Lys
            260                 265                 270
Asp Asp Ala Thr Ala Leu Asn Glu Leu Ser Leu Asn Pro Lys Pro Gly
        275                 280                 285
Thr Pro Ala Ala Ile Gln Pro Asp Ser Pro Lys Leu Pro Thr Ser Asp
    290                 295                 300
Ser Pro Gly Met Val Glu Leu Lys Ala Pro Gln Asn Ser Gly Pro Lys
305                 310                 315                 320
Glu Ser Asn Ala Pro Pro Ser Ala Arg Ile Ala Gly Pro Ala
                325                 330                 335
Leu Pro Gly Arg Pro Ser Gln Leu Ala Pro Ala Thr Leu Arg Ala Pro
            340                 345                 350
Gln Arg His Ser Arg Gly Glu Gly Val Asn Thr Ile Ile Val Val Glu
        355                 360                 365
Arg Val Lys Glu Thr Gly
        370
```

<210> SEQ ID NO 27
<211> LENGTH: 1152
<212> TYPE: DNA

<213> ORGANISM: Homo sapiens

<400> SEQUENCE: 27

```
gctccctcag cccctctgcc tttgggctgt ggctttccgg acatggccca cccctctgag      60
acttcccctc tgaagggtgc ttctgaaaat tccaaacgag atcgccttaa cccagaattt     120
cctgggactc cttaccctga gccttccaag ctacctcata cggtttccct ggaaaccttc     180
ccacttgact tcactgagcc cctcaaccct gacctccgag aaaccccgca cccagagtct     240
cctgagaccc ccaaagctga ctcactcaca acctcaatat cagaatccct ggacatgccc     300
aaaactaacc tctccaaaat ggcacaccca gagtcttctg agaccccac acctggccca      360
actgaaatgc cacacccagg atcccctgag accccaaac ctaacttctc caaaacttca      420
cgcccagaat tcctgagac cccaaacact gaccttatgc aaactacacc ccaagaatcc      480
ccagagattc tgcagcttaa tgccactgaa gtctcacagg cagaactccc cgagacctca     540
aacactaacc ctaccaagac ccctgacccc aaatccccag aaaagcatga cctcaactcc     600
actgagaccc caaactctga atttctccaa gctctccatc ctgacccttc taaaaccccc     660
cacccagaat cccatgtgac ccacaatccc agccccaccg aaatttccca aacagaattc     720
cccacaacct actaccaaaa tgcaacagat gtacccagga cctccgaccc tcaaatctcc     780
actagtctct acccagaaac acctgtgccc ttcaaggatg acgccactgc tctaaatgag     840
ctgtccctga atcccaaacc aggaacacct gcagccatcc agcccgactc cccaaaattg     900
cccacttcag attctccagg aatggttgag ctgaaggccc cccagaactc tggccctaag     960
gagtccaacg cccctcctcc ctcagcccgg attgcaggtc ccctgctct tccagggcgc     1020
cccagtcagt tggcccctgc cactctgcgg gcaccccaga ggcacagccg aggtgaggga    1080
gtcaacacca tcatcgtggt ggagcgagtg aaggagaccg gcgtgactct ggtggggcga    1140
ccacgtggcg ca                                                          1152
```

<210> SEQ ID NO 28
<211> LENGTH: 384
<212> TYPE: PRT
<213> ORGANISM: Homo sapiens

<400> SEQUENCE: 28

```
Ala Pro Ser Ala Pro Leu Pro Leu Gly Cys Gly Phe Pro Asp Met Ala
1               5                   10                  15

His Pro Ser Glu Thr Ser Pro Leu Lys Gly Ala Ser Glu Asn Ser Lys
            20                  25                  30

Arg Asp Arg Leu Asn Pro Glu Phe Pro Gly Thr Pro Tyr Pro Glu Pro
        35                  40                  45

Ser Lys Leu Pro His Thr Val Ser Leu Glu Thr Phe Pro Leu Asp Phe
    50                  55                  60

Thr Glu Pro Leu Asn Pro Asp Leu Arg Glu Thr Pro His Pro Glu Ser
65                  70                  75                  80

Pro Glu Thr Pro Lys Ala Asp Ser Leu Thr Thr Ser Ile Ser Glu Ser
                85                  90                  95

Leu Asp Met Pro Lys Thr Asn Leu Ser Lys Met Ala His Pro Glu Ser
            100                 105                 110

Ser Glu Thr Pro Thr Pro Gly Pro Thr Glu Met Pro His Pro Gly Ser
        115                 120                 125

Pro Glu Thr Pro Lys Pro Asn Phe Ser Lys Ser Arg Pro Glu Phe
    130                 135                 140

Pro Glu Thr Pro Asn Thr Asp Leu Met Gln Thr Thr Pro Gln Glu Ser
```

```
                145                 150                 155                 160
Pro Glu Ile Leu Gln Leu Asn Ala Thr Glu Val Ser Gln Ala Glu Leu
                    165                 170                 175
Pro Glu Thr Ser Asn Thr Asn Pro Thr Lys Thr Pro Asp Pro Lys Ser
                180                 185                 190
Pro Glu Lys His Asp Leu Asn Ser Thr Glu Thr Pro Asn Ser Glu Phe
            195                 200                 205
Leu Gln Ala Leu His Pro Asp Pro Ser Lys Thr Pro His Pro Glu Ser
        210                 215                 220
His Val Thr His Asn Pro Ser Pro Thr Glu Ile Ser Gln Thr Glu Phe
225                 230                 235                 240
Pro Thr Thr Tyr Tyr Gln Asn Ala Thr Asp Val Pro Arg Thr Ser Asp
                245                 250                 255
Pro Gln Ile Ser Thr Ser Leu Tyr Pro Glu Thr Pro Val Pro Phe Lys
            260                 265                 270
Asp Asp Ala Thr Ala Leu Asn Glu Leu Ser Leu Asn Pro Lys Pro Gly
        275                 280                 285
Thr Pro Ala Ala Ile Gln Pro Asp Ser Pro Lys Leu Pro Thr Ser Asp
    290                 295                 300
Ser Pro Gly Met Val Glu Leu Lys Ala Pro Gln Asn Ser Gly Pro Lys
305                 310                 315                 320
Glu Ser Asn Ala Pro Pro Ser Ala Arg Ile Ala Gly Pro Pro Ala
                325                 330                 335
Leu Pro Gly Arg Pro Ser Gln Leu Ala Pro Ala Thr Leu Arg Ala Pro
                340                 345                 350
Gln Arg His Ser Arg Gly Glu Gly Val Asn Thr Ile Ile Val Val Glu
                355                 360                 365
Arg Val Lys Glu Thr Gly Val Thr Leu Val Gly Arg Pro Arg Gly Ala
            370                 375                 380

<210> SEQ ID NO 29
<211> LENGTH: 1491
<212> TYPE: DNA
<213> ORGANISM: Homo sapiens

<400> SEQUENCE: 29
gctccctcag cccctctgcc tttgggctgt ggctttccgg acatggccca cccctctgag      60
acttcccctc tgaagggtgc ttctgaaaat tccaaacgag atcgccttaa cccagaattt     120
cctgggactc ttaccctga gcttccaag ctacctcata cggtttccct ggaaaccttc      180
ccacttgact tcactgagcc cctcaaccct gacctccgag aaaccccgca cccagagtct     240
cctgagaccc caaagctga ctcactcaca acctcaatat cagaatccct ggacatgccc     300
aaaactaacc tctccaaaat ggcacaccca gagtcttctg agaccccccac acctggccca    360
actgaaatgc cacacccagg atcccctgag accccaaac ctaacttctc caaaacttca     420
cgcccagaat tcctgagac cccaaacact gaccttatgc aaactacacc caagaatcc      480
ccagagattc tgcagcttaa tgccactgaa gtctcacagg cagaactccc cgagacctca    540
aacactaacc taccaagac ccctgacccc aaatcccag aaaagcatga cctcaactcc      600
actgagaccc caaactctga atttctccaa gctctccatc ctgacccttc taaaccccc     660
cacccagaat cccatgtgac ccacaatccc agccccaccg aaatttccca aacagaattc    720
cccacaacct actaccaaaa tgcaacagat gtacccagga cctccgaccc tcaaatctcc    780
actagtctct acccagaaac acctgtgccc ttcaaggatg acgccactgc tctaaatgag    840
```

```
ctgtccctga atcccaaacc aggaacacct gcagccatcc agcccgactc cccaaaattg    900
cccacttcag attctccagg aatggttgag ctgaaggccc cccagaactc tggccctaag    960
gagtccaacg cccctcctcc ctcagcccgg attgcaggtc ccctgctctt ccagggcgc   1020 cccagtcagt tggcccctgc cactctgcgg gcaccccaga ggcacagccg aggtgaggga   1080
gtcaacacca tcatcgtggt ggagcgagtg aaggagaccg gcgtgactct ggtggggcga   1140
ccacgtggcg cagcaggcgg ggccctctgc ctgttcttcg cggggaccgc gctgctgatc   1200
ggcatctttg tgctgctgtg gtgtctttac cgccgggcag ctagacagcg gcccttcgca   1260
catcaccggc ttccggacga cggagatgaa ccggttctgc atttggacgc cccgaaagac   1320
ccctacgacc tctactttta tgctccggat acctgggtcc cttcccacat cgccaccaag   1380 cagccccgc ccacacctcc tctgccacca aagctgcccc cgccgcccg cgggggtcgc    1440 ccgcagcgtc tggaggccct gtcccccgcc acgctcccca caacttcgt g             1491
```

<210> SEQ ID NO 30
<211> LENGTH: 497
<212> TYPE: PRT
<213> ORGANISM: Homo sapiens

<400> SEQUENCE: 30

```
Ala Pro Ser Ala Pro Leu Pro Leu Gly Cys Gly Phe Pro Asp Met Ala
1               5                  10                  15

His Pro Ser Glu Thr Ser Pro Leu Lys Gly Ala Ser Glu Asn Ser Lys
            20                  25                  30

Arg Asp Arg Leu Asn Pro Glu Phe Pro Gly Thr Pro Tyr Pro Glu Pro
        35                  40                  45

Ser Lys Leu Pro His Thr Val Ser Leu Glu Thr Phe Pro Leu Asp Phe
    50                  55                  60

Thr Glu Pro Leu Asn Pro Asp Leu Arg Glu Thr Pro His Pro Glu Ser
65                  70                  75                  80

Pro Glu Thr Pro Lys Ala Asp Ser Leu Thr Thr Ser Ile Ser Glu Ser
                85                  90                  95

Leu Asp Met Pro Lys Thr Asn Leu Ser Lys Met Ala His Pro Glu Ser
            100                 105                 110

Ser Glu Thr Pro Thr Pro Gly Pro Thr Glu Met Pro His Pro Gly Ser
        115                 120                 125

Pro Glu Thr Pro Lys Pro Asn Phe Ser Lys Thr Ser Arg Pro Glu Phe
    130                 135                 140

Pro Glu Thr Pro Asn Thr Asp Leu Met Gln Thr Pro Gln Glu Ser
145                 150                 155                 160

Pro Glu Ile Leu Gln Leu Asn Ala Thr Glu Val Ser Gln Ala Glu Leu
                165                 170                 175

Pro Glu Thr Ser Asn Thr Asn Pro Thr Lys Thr Pro Asp Pro Lys Ser
            180                 185                 190

Pro Glu Lys His Asp Leu Asn Ser Thr Glu Thr Pro Asn Ser Glu Phe
        195                 200                 205

Leu Gln Ala Leu His Pro Asp Pro Ser Lys Thr Pro His Pro Glu Ser
    210                 215                 220

His Val Thr His Asn Pro Ser Pro Thr Glu Ile Ser Gln Thr Glu Phe
225                 230                 235                 240

Pro Thr Thr Tyr Tyr Gln Asn Ala Thr Asp Val Pro Arg Thr Ser Asp
                245                 250                 255

Pro Gln Ile Ser Thr Ser Leu Tyr Pro Glu Thr Pro Val Pro Phe Lys
            260                 265                 270
```

```
Asp Asp Ala Thr Ala Leu Asn Glu Leu Ser Leu Asn Pro Lys Pro Gly
        275                 280                 285

Thr Pro Ala Ala Ile Gln Pro Asp Ser Pro Lys Leu Pro Thr Ser Asp
        290                 295                 300

Ser Pro Gly Met Val Glu Leu Lys Ala Pro Gln Asn Ser Gly Pro Lys
305                 310                 315                 320

Glu Ser Asn Ala Pro Pro Ser Ala Arg Ile Ala Gly Pro Pro Ala
            325                 330                 335

Leu Pro Gly Arg Pro Ser Gln Leu Ala Pro Ala Thr Leu Arg Ala Pro
            340                 345                 350

Gln Arg His Ser Arg Gly Glu Gly Val Asn Thr Ile Ile Val Val Glu
        355                 360                 365

Arg Val Lys Glu Thr Gly Val Thr Leu Val Gly Arg Pro Arg Gly Ala
        370                 375                 380

Ala Gly Gly Ala Leu Cys Leu Phe Phe Ala Gly Thr Ala Leu Leu Ile
385                 390                 395                 400

Gly Ile Phe Val Leu Leu Trp Cys Leu Tyr Arg Arg Ala Ala Arg Gln
                405                 410                 415

Arg Pro Phe Ala His His Arg Leu Pro Asp Asp Gly Asp Glu Pro Val
            420                 425                 430

Leu His Leu Asp Ala Pro Lys Asp Pro Tyr Asp Leu Tyr Phe Tyr Ala
        435                 440                 445

Pro Asp Thr Trp Val Pro Ser His Ile Ala Thr Lys Gln Pro Pro Pro
450                 455                 460

Thr Pro Pro Leu Pro Pro Lys Leu Pro Pro Pro Arg Gly Gly Arg
465                 470                 475                 480

Pro Gln Arg Leu Glu Ala Leu Ser Pro Ala Thr Leu Pro Asn Asn Phe
            485                 490                 495

Val

<210> SEQ ID NO 31
<211> LENGTH: 13
<212> TYPE: PRT
<213> ORGANISM: Artificial Sequence
<220> FEATURE:
<223> OTHER INFORMATION: amino acid linker sequence

<400> SEQUENCE: 31

Glu Phe Gly Ala Gly Leu Val Leu Gly Gly Gln Phe Met
1               5                   10

<210> SEQ ID NO 32
<211> LENGTH: 39
<212> TYPE: DNA
<213> ORGANISM: Artificial Sequence
<220> FEATURE:
<223> OTHER INFORMATION: Primer INSP201-CP1

<400> SEQUENCE: 32
atgaaatcat tcagccggat cctcttcctc gtcttcctc                              39

<210> SEQ ID NO 33
<211> LENGTH: 51
<212> TYPE: DNA
<213> ORGANISM: Artificial Sequence
<220> FEATURE:
<223> OTHER INFORMATION: Primer INSP201-CP2

<400> SEQUENCE: 33
```

-continued tgcgccacgt ggtcgcccca ccagagtcac gccggtctcc ttcactcgct c        51

<210> SEQ ID NO 34
<211> LENGTH: 35
<212> TYPE: DNA
<213> ORGANISM: Artificial Sequence
<220> FEATURE:
<223> OTHER INFORMATION: Primer INSP201EC-EX1

<400> SEQUENCE: 34
gcaggcttcg ccaccatgaa atcattcagc cggat        35

<210> SEQ ID NO 35
<211> LENGTH: 35
<212> TYPE: DNA
<213> ORGANISM: Artificial Sequence
<220> FEATURE:
<223> OTHER INFORMATION: Primer INSP201EC-EX2

<400> SEQUENCE: 35
tgatggtgat ggtgtgcgcc acgtggtcgc cccac        35

<210> SEQ ID NO 36
<211> LENGTH: 22
<212> TYPE: DNA
<213> ORGANISM: Artificial Sequence
<220> FEATURE:
<223> OTHER INFORMATION: INSP201-319F-SP1

<400> SEQUENCE: 36
gctgactcac tcacaacctc aa        22

<210> SEQ ID NO 37
<211> LENGTH: 20
<212> TYPE: DNA
<213> ORGANISM: Artificial Sequence
<220> FEATURE:
<223> OTHER INFORMATION: Primer INSP201-570F-SP2

<400> SEQUENCE: 37
tgaagtctca caggcagaac        20

<210> SEQ ID NO 38
<211> LENGTH: 37
<212> TYPE: DNA
<213> ORGANISM: Artificial Sequence
<220> FEATURE:
<223> OTHER INFORMATION: Primer GCP Forward

<400> SEQUENCE: 38
ggggacaagt ttgtacaaaa aagcaggctt cgccacc        37

<210> SEQ ID NO 39
<211> LENGTH: 51
<212> TYPE: DNA
<213> ORGANISM: Artificial Sequence
<220> FEATURE:
<223> OTHER INFORMATION: Primer GCP Reverse

<400> SEQUENCE: 39
ggggaccact ttgtacaaga aagctgggtt tcaatggtga tggtgatggt g        51

<210> SEQ ID NO 40
<211> LENGTH: 20
<212> TYPE: DNA
<213> ORGANISM: Artificial Sequence
<220> FEATURE:

<223> OTHER INFORMATION: Primer pEAK 12F

<400> SEQUENCE: 40
gccagcttgg cacttgatgt                                              20

<210> SEQ ID NO 41
<211> LENGTH: 20
<212> TYPE: DNA
<213> ORGANISM: Artificial Sequence
<220> FEATURE:
<223> OTHER INFORMATION: Primer pEAK 12R

<400> SEQUENCE: 41
gatggaggtg gacgtgtcag                                              20

<210> SEQ ID NO 42
<211> LENGTH: 18
<212> TYPE: DNA
<213> ORGANISM: Artificial Sequence
<220> FEATURE:
<223> OTHER INFORMATION: Primer 21M13

<400> SEQUENCE: 42
tgtaaaacga cggccagt                                                18

<210> SEQ ID NO 43
<211> LENGTH: 18
<212> TYPE: DNA
<213> ORGANISM: Artificial Sequence
<220> FEATURE:
<223> OTHER INFORMATION: Primer M13REV

<400> SEQUENCE: 43
caggaaacag ctatgacc                                                18

<210> SEQ ID NO 44
<211> LENGTH: 19
<212> TYPE: DNA
<213> ORGANISM: Artificial Sequence
<220> FEATURE:
<223> OTHER INFORMATION: Primer T7

<400> SEQUENCE: 44
taatacgact cactatagg                                               19

<210> SEQ ID NO 45
<211> LENGTH: 18
<212> TYPE: DNA
<213> ORGANISM: Artificial Sequence
<220> FEATURE:
<223> OTHER INFORMATION: Primer T3

<400> SEQUENCE: 45
attaaccctc actaaagg                                                18

<210> SEQ ID NO 46
<211> LENGTH: 18
<212> TYPE: DNA
<213> ORGANISM: Artificial Sequence
<220> FEATURE:
<223> OTHER INFORMATION: Reverse Primer Express

<400> SEQUENCE: 46
tcgccccacc agagtcac                                                18

<210> SEQ ID NO 47

<211> LENGTH: 20
<212> TYPE: DNA
<213> ORGANISM: Artificial Sequence
<220> FEATURE:
<223> OTHER INFORMATION: Forward Primer Express

<400> SEQUENCE: 47
ccgaggtgag ggagtcaaca                                              20

<210> SEQ ID NO 48
<211> LENGTH: 22
<212> TYPE: DNA
<213> ORGANISM: Artificial Sequence
<220> FEATURE:
<223> OTHER INFORMATION: GAPDH reverse

<400> SEQUENCE: 48
gatgggattt ccattgatga ca                                           22

<210> SEQ ID NO 49
<211> LENGTH: 18
<212> TYPE: DNA
<213> ORGANISM: Artificial Sequence
<220> FEATURE:
<223> OTHER INFORMATION: GAPDH Forward

<400> SEQUENCE: 49
ccacccatgg caaattcc                                                18

<210> SEQ ID NO 50
<211> LENGTH: 21
<212> TYPE: DNA
<213> ORGANISM: Artificial Sequence
<220> FEATURE:
<223> OTHER INFORMATION: intron-GAPDH reverse

<400> SEQUENCE: 50
cctagtccca gggctttgat t                                            21

<210> SEQ ID NO 51
<211> LENGTH: 22
<212> TYPE: DNA
<213> ORGANISM: Artificial Sequence
<220> FEATURE:
<223> OTHER INFORMATION: intron-GAPDH forward

<400> SEQUENCE: 51
ctgtgctccc actcctgatt tc                                           22

<210> SEQ ID NO 52
<211> LENGTH: 1752
<212> TYPE: DNA
<213> ORGANISM: Homo sapiens
<220> FEATURE:
<221> NAME/KEY: exon
<222> LOCATION: (101)..(1654)

<400> SEQUENCE: 52
gtgggcgtgg cctccgggag tgggcggggc tcctgggagc cttcggcctt aacccttcc    60 ttcccgctct ccccgcagc tataggtatc tgccagagct atg aaa tca ttc agc     115
                                            Met Lys Ser Phe Ser
                                            1               5 cgg atc ctc ttc ctc gtc ttc ctc ctc gcc ggc ctg agg tcc aag gcc    163
Arg Ile Leu Phe Leu Val Phe Leu Leu Ala Gly Leu Arg Ser Lys Ala
        10                  15                  20 gct ccc tca gcc cct ctg cct ttg ggc tgt ggc ttt ccg gac atg gcc    211

```
            Ala Pro Ser Ala Pro Leu Pro Leu Gly Cys Gly Phe Pro Asp Met Ala
                    25                  30                  35 cac ccc tct gag act tcc cct ctg aag ggt gct tct gaa aat tcc aaa         259
His Pro Ser Glu Thr Ser Pro Leu Lys Gly Ala Ser Glu Asn Ser Lys
            40                  45                  50 cga gat cgc ctt aac cca gaa ttt cct ggg act cct tac cct gag cct         307
Arg Asp Arg Leu Asn Pro Glu Phe Pro Gly Thr Pro Tyr Pro Glu Pro
 55                  60                  65 tcc aag cta cct cat acg gtt tcc ctg gaa acc ttc cca ctt gac ttc         355
Ser Lys Leu Pro His Thr Val Ser Leu Glu Thr Phe Pro Leu Asp Phe
 70                  75                  80                  85 act gag ccc ctc aac cct gac ctc cga gaa acc ccg cac cca gag tct         403
Thr Glu Pro Leu Asn Pro Asp Leu Arg Glu Thr Pro His Pro Glu Ser
                90                  95                  100 cct gag acc ccc aaa gct gac tca ctc aca acc tca ata tca gaa tcc         451
Pro Glu Thr Pro Lys Ala Asp Ser Leu Thr Thr Ser Ile Ser Glu Ser
            105                 110                 115 ctg gac atg ccc aaa act aac ctc tcc aaa atg gca cac cca gag tct         499
Leu Asp Met Pro Lys Thr Asn Leu Ser Lys Met Ala His Pro Glu Ser
            120                 125                 130 tct gag acc ccc aca cct ggc cca act gaa atg cca cac cca gga tcc         547
Ser Glu Thr Pro Thr Pro Gly Pro Thr Glu Met Pro His Pro Gly Ser
    135                 140                 145 cct gag acc ccc aaa cct aac ttc tcc aaa act tca cgc cca gaa ttt         595
Pro Glu Thr Pro Lys Pro Asn Phe Ser Lys Thr Ser Arg Pro Glu Phe
150                 155                 160                 165 cct gag acc cca aac act gac ctt atg caa act aca ccc caa gaa tcc         643
Pro Glu Thr Pro Asn Thr Asp Leu Met Gln Thr Thr Pro Gln Glu Ser
                170                 175                 180 cca gag att ctg cag ctt aat gcc act gaa gtc tca cag gca gaa ctc         691
Pro Glu Ile Leu Gln Leu Asn Ala Thr Glu Val Ser Gln Ala Glu Leu
            185                 190                 195 ccc gag acc tca aac act aac cct acc aag acc cct gac ccc aaa tcc         739
Pro Glu Thr Ser Asn Thr Asn Pro Thr Lys Thr Pro Asp Pro Lys Ser
            200                 205                 210 cca gaa aag cat gac ctc aac tcc act gag acc cca aac tct gaa ttt         787
Pro Glu Lys His Asp Leu Asn Ser Thr Glu Thr Pro Asn Ser Glu Phe
    215                 220                 225 ctc caa gct ctc cat cct gac cct tct aaa acc ccc cac cca gaa tcc         835
Leu Gln Ala Leu His Pro Asp Pro Ser Lys Thr Pro His Pro Glu Ser
230                 235                 240                 245 cat gtg acc cac aat ccc agc ccc acc gaa att tcc caa aca gaa ttc         883
His Val Thr His Asn Pro Ser Pro Thr Glu Ile Ser Gln Thr Glu Phe
                250                 255                 260 ccc aca acc tac tac caa aat gca aca gat gta ccc agg acc tcc gac         931
Pro Thr Thr Tyr Tyr Gln Asn Ala Thr Asp Val Pro Arg Thr Ser Asp
            265                 270                 275 cct caa atc tcc act agt ctc tac cca gaa aca cct gtg ccc ttc aag         979
Pro Gln Ile Ser Thr Ser Leu Tyr Pro Glu Thr Pro Val Pro Phe Lys
            280                 285                 290 gat gac gcc act gct cta aat gag ctg tcc ctg aat ccc aaa cca gga        1027
Asp Asp Ala Thr Ala Leu Asn Glu Leu Ser Leu Asn Pro Lys Pro Gly
    295                 300                 305 aca cct gca gcc atc cag ccc gac tcc cca aaa ttg ccc act tca gat        1075
Thr Pro Ala Ala Ile Gln Pro Asp Ser Pro Lys Leu Pro Thr Ser Asp
310                 315                 320                 325 tct cca gga atg gtt gag ctg aag gcc ccc cag aac tct ggc cct aag        1123
Ser Pro Gly Met Val Glu Leu Lys Ala Pro Gln Asn Ser Gly Pro Lys
                330                 335                 340 gag tcc aac gtc cct cct ccc tca gcc cgg att gca ggt ccc cct gct        1171
```

```
Glu Ser Asn Val Pro Pro Ser Ala Arg Ile Ala Gly Pro Pro Ala
            345                 350                 355 ctt cca ggg cgc ccc agt cag ttg gcc cct gcc act ctg cgg gca ccc       1219
Leu Pro Gly Arg Pro Ser Gln Leu Ala Pro Ala Thr Leu Arg Ala Pro
        360                 365                 370 cag agg cac agc cga ggt gag gga gtc aac acc atc atc gtg gtg gag       1267
Gln Arg His Ser Arg Gly Glu Gly Val Asn Thr Ile Ile Val Val Glu
    375                 380                 385 cga gtg aag gag acc ggc gtg act ctg gtg ggg cga cca cgt ggc gca       1315
Arg Val Lys Glu Thr Gly Val Thr Leu Val Gly Arg Pro Arg Gly Ala
390                 395                 400                 405 gca ggc ggg gcc ctc tgc ctg ttc ttc gcg ggg acc gcg ctg ctg atc       1363
Ala Gly Gly Ala Leu Cys Leu Phe Phe Ala Gly Thr Ala Leu Leu Ile
                410                 415                 420 ggc atc ttt gtg ctg ctg tgg tgt ctt tac cgc cgg gca gct aga cag       1411
Gly Ile Phe Val Leu Leu Trp Cys Leu Tyr Arg Arg Ala Ala Arg Gln
            425                 430                 435 cgg ccc ttc gca cat cac cgg ctt ccg gac gac gga gat gaa ccg gtt       1459
Arg Pro Phe Ala His His Arg Leu Pro Asp Asp Gly Asp Glu Pro Val
        440                 445                 450 ctg cat ttg gac gcc ccg aaa gac ccc tac gac ctc tac ttt tat gct       1507
Leu His Leu Asp Ala Pro Lys Asp Pro Tyr Asp Leu Tyr Phe Tyr Ala
455                 460                 465 ccg gat acc tgg gtc cct tcc cac atc gcc acc aag cag ccc ccg ccc       1555
Pro Asp Thr Trp Val Pro Ser His Ile Ala Thr Lys Gln Pro Pro Pro
470                 475                 480                 485 aca cct cct ctg cca cca aag ctg ccc ccg ccc cgc ggg ggt cgc           1603
Thr Pro Pro Leu Pro Pro Lys Leu Pro Pro Pro Arg Gly Gly Arg
                490                 495                 500 ccg cag cgt ctg gag gcc ctg tcc ccc gcc acg ctc ccc aac aac ttc       1651
Pro Gln Arg Leu Glu Ala Leu Ser Pro Ala Thr Leu Pro Asn Asn Phe
        505                 510                 515 gtg tgagcccac cgagttctgc cggacctgca catccccaca gtgaaggaaa             1704
Val accctgcgct tctggtatgc ttagctagag tagtgccccg gataaagg                  1752

<210> SEQ ID NO 53
<211> LENGTH: 1215
<212> TYPE: DNA
<213> ORGANISM: Homo sapiens
<220> FEATURE:
<221> NAME/KEY: exon
<222> LOCATION: (1)..(1215)

<400> SEQUENCE: 53 atg aaa tca ttc agc cgg atc ctc ttc ctc gtc ttc ctc ctc gcc ggc        48
Met Lys Ser Phe Ser Arg Ile Leu Phe Leu Val Phe Leu Leu Ala Gly
1               5                   10                  15 ctg agg tcc aag gcc gct ccc tca gcc cct ctg cct ttg ggc tgt ggc        96
Leu Arg Ser Lys Ala Ala Pro Ser Ala Pro Leu Pro Leu Gly Cys Gly
            20                  25                  30 ttt ccg gac atg gcc cac ccc tct gag act tcc cct ctg aag ggt gct       144
Phe Pro Asp Met Ala His Pro Ser Glu Thr Ser Pro Leu Lys Gly Ala
        35                  40                  45 tct gaa aat tcc aaa cga gat cgc ctt aac cca gaa ttt cct ggg act       192
Ser Glu Asn Ser Lys Arg Asp Arg Leu Asn Pro Glu Phe Pro Gly Thr
    50                  55                  60 cct tac cct gag cct tcc aag cta cct cat acg gtt tcc ctg gaa acc       240
Pro Tyr Pro Glu Pro Ser Lys Leu Pro His Thr Val Ser Leu Glu Thr
65                  70                  75                  80 ttc cca ctt gac ttc act gag ccc ctc aac cct gac ctc gaa acc           288
```

```
        Phe Pro Leu Asp Phe Thr Glu Pro Leu Asn Pro Asp Leu Arg Glu Thr
                        85                  90                  95 ccg cac cca gag tct cct gag acc ccc aaa gct gac tca ctc aca acc        336
Pro His Pro Glu Ser Pro Glu Thr Pro Lys Ala Asp Ser Leu Thr Thr
                100                 105                 110 tca ata tca gaa tcc ctg gac atg ccc aaa act aac ctc tcc aaa atg        384
Ser Ile Ser Glu Ser Leu Asp Met Pro Lys Thr Asn Leu Ser Lys Met
            115                 120                 125 gca cac cca gag tct tct gag acc ccc aca cct ggc cca act gaa atg        432
Ala His Pro Glu Ser Ser Glu Thr Pro Thr Pro Gly Pro Thr Glu Met
        130                 135                 140 cca cac cca gga tcc cct gag acc ccc aaa cct aac ttc tcc aaa act        480
Pro His Pro Gly Ser Pro Glu Thr Pro Lys Pro Asn Phe Ser Lys Thr
145                 150                 155                 160 tca cgc cca gaa ttt cct gag acc cca aac act gac ctt atg caa act        528
Ser Arg Pro Glu Phe Pro Glu Thr Pro Asn Thr Asp Leu Met Gln Thr
                165                 170                 175 aca ccc caa gaa tcc cca gag att ctg cag ctt aat gcc act gaa gtc        576
Thr Pro Gln Glu Ser Pro Glu Ile Leu Gln Leu Asn Ala Thr Glu Val
                180                 185                 190 tca cag gca gaa ctc ccc gag acc tca aac act aac cct acc aag acc        624
Ser Gln Ala Glu Leu Pro Glu Thr Ser Asn Thr Asn Pro Thr Lys Thr
            195                 200                 205 cct gac ccc aaa tcc cca gaa aag cat gac ctc aac tcc act gag acc        672
Pro Asp Pro Lys Ser Pro Glu Lys His Asp Leu Asn Ser Thr Glu Thr
        210                 215                 220 cca aac tct gaa ttt ctc caa gct ctc cat cct gac cct tct aaa acc        720
Pro Asn Ser Glu Phe Leu Gln Ala Leu His Pro Asp Pro Ser Lys Thr
225                 230                 235                 240 ccc cac cca gaa tcc cat gtg acc cac aat ccc agc ccc acc gaa att        768
Pro His Pro Glu Ser His Val Thr His Asn Pro Ser Pro Thr Glu Ile
                245                 250                 255 tcc caa aca gaa ttc ccc aca acc tac tac caa aat gca aca gat gta        816
Ser Gln Thr Glu Phe Pro Thr Thr Tyr Tyr Gln Asn Ala Thr Asp Val
                260                 265                 270 ccc agg acc tcc gac cct caa atc tcc act agt ctc tac cca gaa aca        864
Pro Arg Thr Ser Asp Pro Gln Ile Ser Thr Ser Leu Tyr Pro Glu Thr
            275                 280                 285 cct gtg ccc ttc aag gat gac gcc act gct cta aat gag ctg tcc ctg        912
Pro Val Pro Phe Lys Asp Asp Ala Thr Ala Leu Asn Glu Leu Ser Leu
        290                 295                 300 aat ccc aaa cca gga aca cct gca gcc atc cag ccc gac tcc cca aaa        960
Asn Pro Lys Pro Gly Thr Pro Ala Ala Ile Gln Pro Asp Ser Pro Lys
305                 310                 315                 320 ttg ccc act tca gat tct cca gga atg gtt gag ctg aag gcc ccc cag       1008
Leu Pro Thr Ser Asp Ser Pro Gly Met Val Glu Leu Lys Ala Pro Gln
                325                 330                 335 aac tct ggc cct aag gag tcc aac gcc cct cct ccc tca gcc cgg att       1056
Asn Ser Gly Pro Lys Glu Ser Asn Ala Pro Pro Pro Ser Ala Arg Ile
                340                 345                 350 gca ggt ccc cct gct ctt cca ggg cgc ccc agt cag ttg gcc cct gcc       1104
Ala Gly Pro Pro Ala Leu Pro Gly Arg Pro Ser Gln Leu Ala Pro Ala
            355                 360                 365 act ctg cgg gca ccc cag agg cac agc cga ggt gag gga gtc aac acc       1152
Thr Leu Arg Ala Pro Gln Arg His Ser Arg Gly Glu Gly Val Asn Thr
        370                 375                 380 atc atc gtg gtg gag cga gtg aag gag acc ggc gtg act ctg gtg ggg       1200
Ile Ile Val Val Glu Arg Val Lys Glu Thr Gly Val Thr Leu Val Gly
385                 390                 395                 400 cga cca cgt ggc gca                                                   1215
```

```
Arg Pro Arg Gly Ala
            405
```

US 8,124,748 B2

CELL SURFACE GLYCOPROTEIN

CROSS-REFERENCE TO RELATED APPLICATION

This application is the U.S. national stage application of International Patent Application No. PCT/GB2005/003165, filed Aug. 11, 2005, the disclosure of which is hereby incorporated by reference in its entirety, including all figures, tables and amino acid or nucleic acid sequences.

This invention relates to a novel protein, termed INSP201, herein identified as a cell surface glycoprotein, and to the use of this protein and nucleic acid sequences from the encoding gene in the diagnosis, prevention and treatment of disease.

All publications, patents and patent applications cited herein are incorporated in full by reference.

BACKGROUND

The process of drug discovery is presently undergoing a fundamental revolution as the era of functional genomics comes of age. The term "functional genomics" applies to an approach utilising bioinformatics tools to ascribe function to protein sequences of interest. Such tools are becoming increasingly necessary as the speed of generation of sequence data is rapidly outpacing the ability of research laboratories to assign functions to these protein sequences.

As bioinformatics tools increase in potency and in accuracy, these tools are rapidly replacing the conventional techniques of biochemical characterisation. Indeed, the advanced bioinformatics tools used in identifying the present invention are now capable of outputting results in which a high degree of confidence can be placed.

Various institutions and commercial organisations are examining sequence data as they become available and significant discoveries are being made on an on-going basis. However, there remains a continuing need to identify and characterise further genes and the polypeptides that they encode, as targets for research and for drug discovery.

INTRODUCTION

Secreted Proteins

The ability for cells to make and secrete extracellular proteins is central to many biological processes. Enzymes, growth factors, extracellular matrix proteins and signalling molecules are all secreted by cells. This is through fusion of a secretory vesicle with the plasma membrane. In most cases, but not all, proteins are directed to the endoplasmic reticulum and into secretory vesicles by a signal peptide. Signal peptides are cis-acting sequences that affect the transport of polypeptide chains from the cytoplasm to a membrane bound compartment such as a secretory vesicle. Polypeptides that are targeted to the secretory vesicles are either secreted into the extracellular matrix or are retained in the plasma membrane. The polypeptides that are retained in the plasma membrane will have one or more transmembrane domains. Examples of secreted proteins that play a central role in the functioning of a cell are cytokines, hormones, extracellular matrix proteins (adhesion molecules), proteases, and growth and differentiation factors.

THE INVENTION

The invention is based on the discovery that the INSP201 polypeptide is a cell surface glycoprotein.

In one embodiment of the first aspect of the invention, there is provided a polypeptide which:
(i) comprises the amino acid sequence as recited in SEQ ID NO:2, SEQ ID NO:4, SEQ ID NO:6, SEQ ID NO:8, SEQ ID NO:10, SEQ ID NO:12, SEQ ID NO:14, SEQ ID NO:16 and/or SEQ ID NO:18;
(ii) is a fragment thereof which is a member of the cell surface glycoprotein family, or has an antigenic determinant in common with the polypeptides of (i); or
(iii) is a functional equivalent of (i) or (ii).

Preferably, the polypeptide according to this first aspect of the invention comprises the amino acid sequence as recited in SEQ ID NO:12. A preferred such protein comprises the amino acid sequence as recited in SEQ ID NO:8.

According to a second embodiment of this first aspect of the invention, there is provided a polypeptide which consists of the amino acid sequence as recited in SEQ ID NO:2, SEQ ID NO:4, SEQ ID NO:6, SEQ ID NO:8, SEQ ID NO:10, SEQ ID NO:12, SEQ ID NO:14, SEQ ID NO:16 and/or SEQ ID NO:18.

Preferably, a fragment excluded from the scope of the present invention is that which consists of the first 79 amino acids of SEQ ID NO: 8. This fragment has been disclosed in NCBI GenPept entry AX884746 and in the following patent documents in the name of Genset: US20050106595, U.S. Pat. No. 6,822,072, JP2001269182, JP2002511259, EP1033401, WO9953051 and U.S. Pat. No. 6,783,961. The polypeptide having the sequence recited in SEQ ID NO:2 is referred to hereafter as "the INSP201 exon 1 polypeptide". The polypeptide having the sequence recited in SEQ ID NO:4 is referred to hereafter as "the INSP201 exon 2 polypeptide". The polypeptide having the sequence recited in SEQ ID NO:6 is referred to hereafter as "the INSP201 exon 3 polypeptide". The polypeptide having the sequence recited in SEQ ID NO:8 is referred to hereafter as "the full length INSP201 polypeptide".

Although the Applicant does not wish to be bound by this theory, it is postulated that the first 21 amino acids of the INSP201 polypeptide form a signal peptide.

The INSP201 exon 1 polypeptide without this postulated signal sequence is recited in SEQ ID NO: 10. The full length INSP201 polypeptide sequence without this postulated signal sequence is recited in SEQ ID NO: 12.

The polypeptide having the sequence recited in SEQ ID NO: 10 is referred to hereafter as "the INSP201 exon 1 mature polypeptide". The polypeptide having the sequence recited in SEQ ID NO: 12 is referred to hereafter as "the INSP201 mature polypeptide".

It is predicted herein that the INSP201 polypeptide contains a number of possible N-glycosylation sites. Accordingly, glycoproteins comprising or consisting of the INSP201 polypeptide modified by N-glycosylation in one, two, three, four, five, six or seven of the positions corresponding to Asn124, Asn156, Asn188, Asn204, Asn220, Asn250, and Asn268 of SEQ ID NO:8. are included as aspects of the invention.

It is predicted herein that the INSP201 polypeptide contains a transmembrane region between residues 406-427 inclusive of SEQ ID NO:8. Accordingly, extracellular variants of the INSP201 polypeptide are included as aspects of the invention. Preferred such variants include extracellular forms that comprise or consist of amino acid residues 1-405 of SEQ ID NO:8, or 22-405 inclusive of SEQ ID NO:8, in both their apo and N-glycosylated forms as herein described. The polypeptide having the sequence recited in SEQ ID NO:14 is referred to hereafter as "the INSP201 extracellular polypeptide". The polypeptide having the sequence recited in SEQ ID NO:18 is referred to hereafter as "the INSP201 mature extracellular polypeptide" and excludes the amino acids that are predicted to form the INSP201 polypeptide signal peptide.

Polypeptide variants of this type are of particular utility in screening assays for ligands, such as secreted ligands that bind to the INSP201 polypeptide and to other proteins of this type. Such variants may also be used for quantification of such ligands, for example, in diagnosis of diseases in which these ligands and this polypeptide play a role.

The intracellular variant of the INSP201 polypeptide is also included as an aspect of the invention. This variant is a polypeptide consisting of amino acid residues 428-518 inclusive of SEQ ID NO:8. The polypeptide having the sequence recited in SEQ ID NO:16 is referred to hereafter as "the INSP201 intracellular polypeptide".

The term "INSP201 polypeptides" as used herein includes polypeptides comprising the INSP201 exon 1 polypeptide, the INSP201 exon 2 polypeptide, the INSP201 exon 3 polypeptide, the full length INSP201 polypeptide, the INSP201 exon 1 mature polypeptide, the INSP201 mature polypeptide, the INSP201 extracellular polypeptide, the INSP201 mature extracellular polypeptide and the INSP201 intracellular polypeptide. All these polypeptides form aspects of the present invention.

Preferably, a polypeptide according to the above embodiments of the first aspect of the invention functions as a secreted protein, particularly as a member of cell surface glycoprotein family.

Cell surface glycoproteins are of significant interest to human biology, and thus physiology and health. Of course, the outer surface of the cell membrane plays a major role in the assembly and maintenance of tissue integrity. The outer surfaces of developing and differentiated cells contain receptor molecules that recognise systemic signals, ligands or hormones. The binding or dissociation of the ligands controls some of the differentiated functions of the cell, keeping it in tune with the needs of the whole system. The outer surface is also coated with glycoproteins and proteoglycans. These large complexes of protein and polysaccharides provide a tissue-specific matrix within which cells of like function can operate together as a coherent tissue. In embryogenesis the sorting out and tying together of cells with a common function is facilitated, and probably controlled, thorough the molecular specificities of the glycoprotein and proteoglycan surfaces of the cells.

The carbohydrate chains are N- and O-glycosidically-linked to glycoproteins forming complex structures. In fact, The N- and O-glycan chains are assembled in the endoplasmic reticulum and the Golgi by a controlled sequence of glycosyltransferase and glycosidase processing reactions subject to specific regulatory events (for example, at the level of gene expression or localisation of the enzyme). This complex regulation results in many hundreds of structures, the range of which varies amongst cell/tissue types or development/differentiation status.

There is a growing interest in diseases caused by defective glycosylation, and in therapeutic glycoproteins produced through recombinant DNA technology route. In particular, diseased cells may have relative proportions of these structures that are often characteristically different from normal, and may be useful for the assessment of the stage of the disease and for diagnosis. Knowledge of disease-specific glycoprotein structures and their functions may be used therapeutically, in immunotherapy, in blocking cell adhesion or interfering with other binding or biological processes (Brockhausen I et al., Acta Anat. 1998; 161(1-4):36-78; Bhatia P K and Mukhopadhyay A, Adv Biochem Eng Biotechnol. 1999; 64: 155-201).

For example, the relationship between glycosylation/expression of glycoproteins and cancer progression/malignancy (Dennis J W et al., Biochim Biophys Acta. 1999 Dec. 6; 1473(1):21-34) or hereditary diseases (Dennis J W et al., Bioessays. 1999 May; 21(5):412-21) have been studied.

Given that glycoproteins are typically expressed as mixtures of glycoforms, various technologies have been developed to obtain homogeneous glycopeptide and glycoprotein materials for experiments relevant to the biological investigation of glycoproteins (Grogan M J et al., Annu Rev Biochem. 2002; 71: 593-634).

Many cell surface glycoproteins are subjected to limited proteolysis by cellular proteases. This shedding mechanism allows secretion of extracellular domains that may affect the binding activities of other circulating proteins recognised by these extracellular regions. In fact, the shedding of extracellular domains, by altering cellular responses to exogenous stimuli, is involved in a number of pathophysiological processes, such as inflammation, cell degeneration and apoptosis, and oncogenesis, as intensively studied in cytokine/cytokine receptors systems (Mullberg J et al., Eur Cytokine Netw. 2000 Mar.; 11(1):27-38; Arribas J and Merlos-Suarez A Curr Top Dev Biol. 2003; 54:125-44; Dello Sbarba P and Rovida E; Biol. Chem. 2002 January; 383(1):69-83).

The polypeptides of the first aspect of the invention may further comprise a histidine tag. Preferably the histidine tag is found at the C-terminal of the polypeptide. Preferably the histidine tag comprises 1-10 histidine residues (e.g. 1, 2, 3, 4, 5, 6, 7, 8, 9 or 10 residues). More preferably the histidine tag comprises 6 histidine residues.

An "antigenic determinant" of the present invention may be a part of a polypeptide of the present invention, which binds to an antibody-combining site or to a T-cell receptor (TCR). Alternatively, an "antigenic determinant" may be a site on the surface of a polypeptide of the present invention to which a single antibody molecule binds. Generally an antigen has several or many different antigenic determinants and reacts with antibodies of many different specificities. Preferably, the antibody is immunospecific to a polypeptide of the invention. Preferably, the antibody is immunospecific to a polypeptide of the invention, which is not part of a fusion protein. Preferably, the antibody is immunospecific to INSP201 or a fragment thereof. Antigenic determinants usually consist of chemically active surface groupings of molecules, such as amino acids or sugar side chains, and can have specific three dimensional structural characteristics, as well as specific charge characteristics. Preferably, the "antigenic determinant" refers to a particular chemical group on a polypeptide of the present invention that is antigenic, i.e. that elicit a specific immune response.

In a second aspect, the invention provides a purified nucleic acid molecule which encodes a polypeptide of the first aspect of the invention.

The term "purified nucleic acid molecule" preferably refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "purified nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use. In a preferred embodiment, genomic DNA molecules are specifically excluded from the scope of the invention. Preferably, genomic DNA larger than 10 kbp (kilo base pairs), 50 kbp, 100 kbp, 150 kbp, 200 kbp, 250 kbp or 300 kbp are specifically excluded from the scope of the invention. Preferably, the "purified nucleic acid molecule" consists of cDNA only.

Preferably, the purified nucleic acid molecule comprises the nucleic acid sequence as recited in SEQ ID NO:1 (encoding the INSP201 exon 1 polypeptide), SEQ ID NO:3 (encoding the INSP201 exon 2 polypeptide), SEQ ID NO:5 (encoding the INSP201 exon 3 polypeptide), SEQ ID NO:7 (encoding the INSP201 polypeptide), SEQ ID NO:9 (encoding the INSP201 exon 1 mature polypeptide), SEQ ID NO:11 (encoding the INSP201 mature polypeptide), SEQ ID NO:13 (encoding the INSP201 extracellular polypeptide), SEQ ID NO:15 (encoding the INSP201 intracellular polypeptide) or SEQ ID NO:17 (encoding the INSP201 mature extracellular polypeptide) or is a redundant equivalent or fragment of any one of these sequences.

The invention further provides that the purified nucleic acid molecule consists of the nucleic acid sequence as recited in SEQ ID NO:1 (encoding the INSP201 exon 1 polypeptide), SEQ ID NO:3 (encoding the INSP201 exon 2 polypeptide), SEQ ID NO:5 (encoding the INSP201 exon 3 polypeptide), SEQ ID NO:7 (encoding the INSP201 polypeptide), SEQ ID NO:9 (encoding the INSP201 exon 1 mature polypeptide), SEQ ID NO: 11 (encoding the INSP201 mature polypeptide), SEQ ID NO:13 (encoding the INSP201 extracellular polypeptide), SEQ ID NO:15 (encoding the INSP201 intracellular polypeptide) or SEQ ID NO:17 (encoding the INSP201 mature extracellular polypeptide) or is a redundant equivalent or fragment of any one of these sequences.

In a third aspect, the invention provides a purified nucleic acid molecule which hybridizes under high stringency conditions with a nucleic acid molecule of the second aspect of the invention. High stringency hybridisation conditions are defined as overnight incubation at 42° C. in a solution comprising 50% formamide, 5×SSC (150 mM NaCl, 15 mM trisodium citrate), 50 mM sodium phosphate (pH7.6), 5×Denhardts solution, 10% dextran sulphate, and 20 microgram/ml denatured, sheared salmon sperm DNA, followed by washing the filters in 0.1×SSC at approximately 65° C.

As used herein, "functional equivalent" refers to a protein or nucleic acid molecule that possesses functional or structural characteristics that are substantially similar to a polypeptide or nucleic acid molecule of the present invention. A functional equivalent of a protein may contain modifications depending on the necessity of such modifications for the performance of a specific function. The term "functional equivalent" is intended to include the fragments, mutants, hybrids, variants, analogs, or chemical derivatives of a molecule.

Preferably, the "functional equivalent" may be a protein or nucleic acid molecule that exhibits any one or more of the functional activities of the polypeptides of the present invention.

Preferably, the "functional equivalent" may be a protein or nucleic acid molecule that displays substantially similar activity compared with INSP201 or fragments thereof in a suitable assay for the measurement of biological activity or function. Preferably, the "functional equivalent" may be a protein or nucleic acid molecule that displays identical or higher activity compared with INSP201 or fragments thereof in a suitable assay for the measurement of biological activity or function. Preferably, the "functional equivalent" may be a protein or nucleic acid molecule that displays 50%, 60%, 70%, 80%, 90%, 95%, 98%, 99%, 100% or more activity compared with INSP201 or fragments thereof in a suitable assay for the measurement of biological activity or function.

Preferably, the "functional equivalent" may be a protein or polypeptide capable of exhibiting a substantially similar in vivo or in vitro activity as the polypeptides of the invention. Preferably, the "functional equivalent" may be a protein or polypeptide capable of interacting with other cellular or extracellular molecules in a manner substantially similar to the way in which the corresponding portion of the polypeptides of the invention would. For example, a "functional equivalent" would be able, in an immunoassay, to diminish the binding of an antibody to the corresponding peptide (i.e., the peptide the amino acid sequence of which was modified to achieve the "functional equivalent") of the polypeptide of the invention, or to the polypeptide of the invention itself, where the antibody was raised against the corresponding peptide of the polypeptide of the invention.

An equimolar concentration of the functional equivalent will diminish the aforesaid binding of the corresponding peptide by at least about 5%, preferably between about 5% and 10%, more preferably between about 10% and 25%, even more preferably between about 25% and 50%, and most preferably between about 40% and 50%.

For example, functional equivalents can be fully functional or can lack function in one or more activities. Thus, in the present invention, variations can affect the function, for example, of the activities of the polypeptide that reflect its identity as a cell surface glycoprotein. In a fourth aspect, the invention provides a vector, such as an expression vector, that contains a nucleic acid molecule of the second or third aspect of the invention.

In a fifth aspect, the invention provides a host cell transformed with a vector of the fourth aspect of the invention.

In a sixth aspect, the invention provides a ligand which binds specifically to members of the cell surface glycoprotein family of the first aspect of the invention. Preferably, the ligand inhibits the function of a polypeptide of the first aspect of the invention which is a member of the cell surface glycoprotein family. Ligands to a polypeptide according to the invention may come in various forms, including natural or modified substrates, enzymes, receptors, small organic molecules such as small natural or synthetic organic molecules of up to 2000 Da, preferably 800 Da or less, peptidomimetics, inorganic molecules, peptides, polypeptides, antibodies, structural or functional mimetics of the aforementioned.

In a seventh aspect, the invention provides a compound that is effective to alter the expression of a natural gene which encodes a polypeptide of the first aspect of the invention or to regulate the activity of a polypeptide of the first aspect of the invention.

Such compounds may be identified using the assays and screening methods disclosed herein.

A compound of the seventh aspect of the invention may either increase (agonise) or decrease (antagonise) the level of expression of the gene or the activity of the polypeptide.

Importantly, the identification of the function of the INSP201 polypeptide allows for the design of screening methods capable of identifying compounds that are effective in the treatment and/or diagnosis of disease. Extracellular and intracellular forms of the INSP201 polypeptide are likely to be of particular utility in screening methods of this nature. Ligands and compounds according to the sixth and seventh aspects of the invention may be identified using such methods. These methods are included as aspects of the present invention.

Another aspect of this invention resides in the use of an INSP210 gene or polypeptide as a target for the screening of candidate drug modulators, particularly candidate drugs active against cell surface glycoprotein related disorders.

A further aspect of this invention resides in methods of screening of compounds for therapy of cell surface glycoprotein related disorders, comprising determining the ability of a compound to bind to an INSP210 gene or polypeptide, or a fragment thereof.

A further aspect of this invention resides in methods of screening of compounds for therapy of cell surface glycoprotein related disorders, comprising testing for modulation of the activity of an INSP210 gene or polypeptide, or a fragment thereof.

In an eighth aspect, the invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in therapy or diagnosis of diseases in which members of the cell surface glycoprotein family are implicated. Such diseases may include cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; respiratory tract disorders, including chronic obstructive pulmonary disease and cystic fibrosis; developmental disorders; metabolic disorders including diabetes mellitus, osteoporosis, and obesity, AIDS and renal disease; infections including viral infection, bacterial infection, fungal infection and parasitic infection and other pathological conditions. Preferably, the diseases are those in which cell surface glycoproteins are implicated. These molecules may also be used in the manufacture of a medicament for the treatment of such diseases. These molecules may also be used in contraception or for the treatment of reproductive disorders including infertility.

The moieties of the present invention (i.e. the polypeptides of the first aspect of the invention, a nucleic acid molecule of the second or third aspect of the invention, a vector of the fourth aspect of the invention, a host cell of the fifth aspect of the invention, a ligand of the sixth aspect of the invention, a compound of the seventh aspect of the invention) may have particular utility in the therapy or diagnosis of disorders/diseases (the two terms are used interchangeably herein) involving inflammation, cell degeneration and apoptosis, and oncogenesis.

In a ninth aspect, the invention provides a method of diagnosing a disease in a patient, comprising assessing the level of expression of a natural gene encoding a polypeptide of the first aspect of the invention or the activity of a polypeptide of the first aspect of the invention in tissue from said patient and comparing said level of expression or activity to a control level, wherein a level that is different to said control level is indicative of disease. Such a method will preferably be carried out in vitro. Similar methods may be used for monitoring the therapeutic treatment of disease in a patient, wherein altering the level of expression or activity of a polypeptide or nucleic acid molecule over the period of time towards a control level is indicative of regression of disease.

A preferred method for detecting polypeptides of the first aspect of the invention comprises the steps of: (a) contacting a ligand, such as an antibody, of the sixth aspect of the invention with a biological sample under conditions suitable for the formation of a ligand-polypeptide complex; and (b) detecting said complex.

A number of different such methods according to the ninth aspect of the invention exist, as the skilled reader will be aware, such as methods of nucleic acid hybridization with short probes, point mutation analysis, polymerase chain reaction (PCR) amplification and methods using antibodies to detect aberrant protein levels. Similar methods may be used on a short or long term basis to allow therapeutic treatment of a disease to be monitored in a patient. The invention also provides kits that are useful in these methods for diagnosing disease.

In a tenth aspect, the invention provides for the use of a polypeptide of the first aspect of the invention as a cell surface glycoprotein. Suitable uses of the polypeptides of the invention as cell surface glycoproteins include use as a regulator of cellular growth, metabolism or differentiation, use as part of a receptor/ligand pair and use as a diagnostic marker for a physiological or pathological condition.

In an eleventh aspect, the invention provides a pharmaceutical composition comprising a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, in conjunction with a pharmaceutically-acceptable carrier.

In a twelfth aspect, the present invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in the manufacture of a medicament for the diagnosis or treatment of a disease, including, but not limited to, myeloproliferative disorders such as leukemia, lymphoma, myelodysplastic syndromes and carcinoma, neoplasm, melanoma, lung, colorectal, breast, pancreas, head and neck and other solid tumours, blood disorders such as macroglobulinemia, autoimmune disease and inflammatory disorders, including allergy, inflammatory bowel disease, arthritis, psoriasis, multiple sclerosis and respiratory tract inflammation, asthma, and organ transplant rejection, B-cell disorders, cardiovascular disorders, neurological disorders, developmental disorders, fertility disorders, metabolic disorders, AIDS, renal disease, infections and other pathological conditions.

In a thirteenth aspect, the invention provides a method of treating a disease in a patient comprising administering to the patient a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention.

For diseases in which the expression of a natural gene encoding a polypeptide of the first aspect of the invention, or in which the activity of a polypeptide of the first aspect of the invention, is lower in a diseased patient when compared to the level of expression or activity in a healthy patient, the polypeptide, nucleic acid molecule, ligand or compound administered to the patient should be an agonist. Conversely, for diseases in which the expression of the natural gene or activity of the polypeptide is higher in a diseased patient when compared to the level of expression or activity in a healthy patient, the polypeptide, nucleic acid molecule, ligand or compound administered to the patient should be an antagonist. Examples of such antagonists include antisense nucleic acid molecules, ribozymes and ligands, such as antibodies.

The INSP201 polypeptides are cell surface glycoproteins and thus have roles in many disease states. Antagonists of the INSP201 polypeptides are of particular interest as they provide a way of modulating these disease states.

In a fourteenth aspect, the invention provides transgenic or knockout non-human animals that have been transformed to express higher, lower or absent levels of a polypeptide of the first aspect of the invention. Such transgenic animals are very useful models for the study of disease and may also be used in screening regimes for the identification of compounds that are effective in the treatment or diagnosis of such a disease.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of those working in the art.

Such techniques are explained fully in the literature. Examples of particularly suitable texts for consultation include the following: Sambrook Molecular Cloning; A Laboratory Manual, Second Edition (1989); DNA Cloning, Volumes I and II (D. N Glover ed. 1985); Oligonucleotide Synthesis (M. J. Gait ed. 1984); Nucleic Acid Hybridization (B. D. Hames & S. J. Higgins eds. 1984); Transcription and Translation (B. D. Hames & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D. M. Weir and C. C. Blackwell eds. 1986).

As used herein, the term "polypeptide" includes any peptide or protein comprising two or more amino acids joined to each other by peptide bonds or modified peptide bonds, i.e. peptide isosteres. This term refers both to short chains (peptides and oligopeptides) and to longer chains (proteins).

The polypeptide of the present invention may be in the form of a mature protein or may be a pre-, pro- or prepro-protein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence.

The polypeptide of the first aspect of the invention may form part of a fusion protein. For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature polypeptide may be fused with another compound, such as a compound to increase the half-life of the polypeptide (for example, polyethylene glycol).

A fusion protein of the polypeptide of the first aspect of the invention may e.g. comprise an immunoglobulin fusion, i.e. a fused protein comprising all or fragment of the extracellular INSP201 (e.g. INSP201-EC), which is fused to all or a portion of an immunoglobulin. Methods for making immunoglobulin fusion proteins are well known in the art, such as the ones described in WO 01/03737, for example. The person skilled in the art will appreciate that the resulting fusion protein of the invention substantially retains the biological activity of the polypeptide of the first aspect of the invention, such as e.g. IL-2 inhibition, which can be measured in in vitro assays described in Example 6, or in a cancer assay as described in Example 7 or in animal models of inflammatory bowel disease as described in Example 8. The fusion may be direct, or via a short linker peptide which can be as short as 1 to 3 amino acid residues in length or longer, for example, 5, 7, 9, 11 or 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO 31) introduced between the polypeptide of the first aspect of the invention sequence and the immunoglobulin sequence. The resulting fusion protein has improved properties, such as an extended residence time in body fluids (half-life), increased specific activity, increased expression level, or the purification of the fusion protein is facilitated.

In a preferred embodiment, the polypeptide of the first aspect of the invention is fused to the constant region of an Ig molecule, e.g. an Fc portion of an Immunoglobulin. Preferably, it is fused to heavy chain regions, like the CH2 and CH3 domains, optionally with the hinge region of human IgG1, for example. The Fc part may e.g. be mutated in order to prevent unwanted activities, such as complement binding, binding to Fc receptors, or the like.

The generation of specific fusion proteins comprising the polypeptide of the first aspect of the invention and a portion of an immunoglobulin are described in example 11 of WO 99/09063, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

Further fusion proteins of the polypeptide of the first aspect of the invention may be prepared by fusing domains isolated from other proteins allowing the formation or dimers, trimers, etc. Examples for protein sequences allowing the multimerization of the polypeptides of the Invention are domains isolated from proteins such as hCG (WO 97/30161), collagen X (WO 04/33486), C4BP (WO 04/20639), Erb proteins (WO 98/02540), or coiled coil peptides (WO 01/00814). Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include isolated naturally-occurring polypeptides (for example purified from cell culture), recombinantly-produced polypeptides (including fusion proteins), synthetically-produced polypeptides or polypeptides that are produced by a combination of these methods (see, for example, Bray 2003, Nat Rev Drug Discov, 2(7):587-93; Casi & Hilvert 2003, Curr Opin Struct Biol, 13(5):589-94).

The functionally-equivalent polypeptides of the first aspect of the invention may be polypeptides that are homologous to the INSP201 polypeptide. Two polypeptides are said to be "homologous", as the term is used herein, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Homologous polypeptides therefore include natural biological variants (for example, allelic variants or geographical variations within the species from which the polypeptides are derived) and mutants (such as mutants containing amino acid substitutions, insertions or deletions) of the INSP201 polypeptide. Such mutants may include polypeptides in which one or more of the amino acid residues are substituted with a conserved or non-conserved amino acid residue (preferably a conserved amino acid residue) and such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions. Such mutants also include polypeptides in which one or more of the amino acid residues includes a substituent group.

In accordance with the present invention, any substitution should be preferably a "conservative" or "safe" substitution, which is commonly defined a substitution introducing an amino acids having sufficiently similar chemical properties (e.g. a basic, positively charged amino acid should be replaced by another basic, positively charged amino acid), in order to preserve the structure and the biological function of the molecule.

The literature provide many models on which the selection of conservative amino acids substitutions can be performed on the basis of statistical and physico-chemical studies on the sequence and/or the structure of proteins (Rogov S I and Nekrasov A N, 2001). Protein design experiments have shown that the use of specific subsets of amino acids can produce foldable and active proteins, helping in the classification of amino acid "synonymous" substitutions which can be more easily accommodated in protein structure, and which can be used to detect functional and structural homologs and paralogs (Murphy L R et al., 2000). The groups of synonymous amino acids and the groups of more preferred synonymous amino acids are shown in Table 1.

Specific, non-conservative mutations can be also introduced in the polypeptides of the invention with different purposes. Mutations reducing the affinity of the cell surface glycoprotein may increase its ability to be reused and recycled, potentially increasing its therapeutic potency (Robinson C R, 2002). Immunogenic epitopes eventually present in the polypeptides of the invention can be exploited for developing vaccines (Stevanovic S, 2002), or eliminated by modifying their sequence following known methods for selecting mutations for increasing protein stability, and correcting them (van den Burg B and Eijsink V, 2002; WO 02/05146, WO 00/34317, WO 98/52976).

Preferred alternative, synonymous groups for amino acids derivatives included in peptide mimetics are those defined in Table 2. A non-exhaustive list of amino acid derivatives also include aminoisobutyric acid (Aib), hydroxyproline (Hyp), 1,2,3,4-tetrahydro-isoquinoline-3-COOH, indoline-2carboxylic acid, 4-difluoro-proline, L-thiazolidine-4-carboxylic acid, L-homoproline, 3,4-dehydro-proline, 3,4-dihydroxyphenylalanine, cyclohexyl-glycine, and phenylglycine.

By "amino acid derivative" is intended an amino acid or amino acid-like chemical entity other than one of the 20 genetically encoded naturally occurring amino acids. In particular, the amino acid derivative may contain substituted or non-substituted, linear, branched, or cyclic alkyl moieties, and may include one or more heteroatoms. The amino acid derivatives can be made de novo or obtained from commercial sources (Calbiochem-Novabiochem AG, Switzerland; Bachem, USA).

Various methodologies for incorporating unnatural amino acids derivatives into proteins, using both in vitro and in vivo translation systems, to probe and/or improve protein structure and function are disclosed in the literature (Dougherty D A, 2000). Techniques for the synthesis and the development of peptide mimetics, as well as non-peptide mimetics, are also well known in the art (Golebiowski A et al., 2001; Hruby V J and Balse P M, 2000; Sawyer T K, in "Structure Based Drug Design", edited by Veerapandian P, Marcel Dekker Inc., pg. 557-663, 1997).

Typically, greater than 30% identity between two polypeptides is considered to be an indication of functional equivalence. Preferably, functionally equivalent polypeptides of the first aspect of the invention have a degree of sequence identity with the INSP201 polypeptide, or with active fragments thereof, of greater than 80%. More preferred polypeptides have degrees of identity of greater than 85%, 90%, 95%, 98% or 99%, respectively.

The functionally-equivalent polypeptides of the first aspect of the invention may also be polypeptides which have been identified using one or more techniques of structural alignment. For example, the Inpharmatica Genome Threader technology that forms one aspect of the search tools used to generate the Biopendium™ search database may be used (see PCT application WO 01/69507) to identify polypeptides of presently-unknown function which, while having low sequence identity as compared to the INSP201 polypeptide, are predicted to be members of the cell surface glycoprotein family, by virtue of sharing significant structural homology with the INSP201 polypeptide sequence. By "significant structural homology" is meant that the Inpharmatica Genome Threader predicts two proteins to share structural homology with a certainty of 10% and above.

The polypeptide of the first aspect of the invention also include fragments of the INSP201 polypeptide and fragments of the functional equivalents of the INSP201 polypeptide, provided that those fragments are members of the cell surface glycoprotein family or have an antigenic determinant in common with the INSP201 polypeptide.

As used herein, the term "fragment" refers to a polypeptide having an amino acid sequence that is the same as part, but not all, of the amino acid sequence of the INSP201 polypeptide or one of its functional equivalents. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

Preferably, the minimum length of a fragment according to the invention is of 6, 10, 25, 50, 100, 150, 200, 250, 300, 350, 400, 450 or 500 amino acids.

Preferably, the maximum length of a fragment according to the invention is of 517, 515, 510, 500, 475, 450, 400, 350, 300, 250, 200, 150, 100 or 50 amino acids.

Preferably, the minimum length of a nucleic acid molecule encoding a fragment according to the invention is of 18, 30, 75, 150, 300, 450, 600, 750, 900, 1050, 1200, 1350, or 1500 nucleic acids.

Preferably, the maximum length of a nucleic acid molecule encoding a fragment according to the invention is of 1551, 1545, 1530, 1500, 1425, 1350, 1200, 1050, 900, 750, 600, 450, 300 or 150 nucleic acids.

Preferably, the maximum length of a polypeptide of the present invention is 518, 520, 550, 600, 650, 700, 800, 900, 1000, 1250, 1500, 2000, 2500, 3000, 3500, 4000, 4500 or 5000 amino acids.

Preferably, the maximum length of a nucleic acid encoding a polypeptide of the present invention is 1554, 1560, 1750, 1800, 1950, 2100, 2400, 2700, 3000, 5000, 7500, 10000, 20000, 30000, 50000, 75000 or 100000 nucleic acids.

Fragments of the full length INSP201 polypeptide may consist of combinations of 2, or all 3 neighbouring exon sequences in the INSP201 polypeptide sequences, respectively.

Such fragments may be "free-standing", i.e. not part of or fused to other amino acids or polypeptides, or they may be comprised within a larger polypeptide of which they form a part or region. When comprised within a larger polypeptide, the fragment of the invention most preferably forms a single continuous region. For instance, certain preferred embodiments relate to a fragment having a pre- and/or pro-polypeptide region fused to the amino terminus of the fragment and/or an additional region fused to the carboxyl terminus of the fragment. However, several fragments may be comprised within a single larger polypeptide.

The polypeptides of the present invention or their immunogenic fragments (comprising at least one antigenic determinant) can be used to generate ligands, such as polyclonal or monoclonal antibodies, that are immunospecific for the polypeptides. Such antibodies may be employed to isolate or to identify clones expressing the polypeptides of the invention or to purify the polypeptides by affinity chromatography. The antibodies may also be employed as diagnostic or therapeutic aids, amongst other applications, as will be apparent to the skilled reader.

The term "immunospecific" means that the antibodies have substantially greater affinity for the polypeptides of the invention than their affinity for other related polypeptides in the prior art. As used herein, the term "antibody" refers to intact molecules as well as to fragments thereof, such as Fab, F(ab')2 and Fv, which are capable of binding to the antigenic determinant in question. Such antibodies thus bind to the polypeptides of the first aspect of the invention.

By "substantially greater affinity" we mean that there is a measurable increase in the affinity for a polypeptide of the invention as compared with the affinity for known secreted proteins.

Preferably, the affinity is at least 1.5-fold, 2-fold, 5-fold 10-fold, 100-fold, $10^3$-fold, $10^4$-fold, $10^5$-fold, $10^6$-fold or greater for a polypeptide of the invention than for known secreted proteins such as members of the cell surface glycoprotein family.

Preferably, there is a measurable increase in the affinity for a polypeptide of the invention as compared with known cell surface glycoproteins.

If polyclonal antibodies are desired, a selected mammal, such as a mouse, rabbit, goat or horse, may be immunised with a polypeptide of the first aspect of the invention. The polypeptide used to immunise the animal can be derived by recombinant DNA technology or can be synthesized chemically. If desired, the polypeptide can be conjugated to a carrier protein. Commonly used carriers to which the polypeptides may be chemically coupled include bovine serum albumin, thyroglobulin and keyhole limpet haemocyanin. The coupled polypeptide is then used to immunise the animal. Serum from the immunised animal is collected and treated according to known procedures, for example by immunoaffinity chromatography.

Monoclonal antibodies to the polypeptides of the first aspect of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R. Liss, Inc. (1985).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321, 522 (1986); Verhoeyen et al., Science, 239, 1534 (1988); Kabat et al., J. Immunol., 147, 1709 (1991); Queen et al., Proc. Natl. Acad. Sci. USA, 86, 10029 (1989); Gorman et al., Proc. Natl. Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is, an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Polyclonal antibodies directed toward a polypeptide of the present invention generally are produced in animals (e.g., rabbits or mice) by means of multiple subcutaneous or intraperitoneal injections of the INSP201 polypeptide and an adjuvant. It may be useful to conjugate a polypeptide of the present invention to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-INSP201 antibody titer.

Monoclonal antibodies directed toward a polypeptide of the present invention are produced using any method that provides for the production of antibody molecules by continuous cell lines in culture. Examples of suitable methods for preparing monoclonal antibodies include the hybridoma methods and the human B-cell hybridoma method. Also provided by the invention are hybridoma cell lines that produce monoclonal antibodies reactive with the INSP201 polypeptide.

Monoclonal antibodies of the invention may be modified for use as therapeutics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity.

In another embodiment, a monoclonal antibody of the invention is a "humanized" antibody. Generally, a humanized antibody has one or more amino acid residues introduced into it from a source that is non-human. Humanization can be performed, for example, using methods described in the art, by substituting at least a portion of a rodent complementarity-determining region for the corresponding regions of a human antibody.

The term "antibody" or "immunoglobulin" is intended to encompass both polyclonal and monoclonal antibodies. The preferred antibody is a monoclonal antibody reactive with the antigen. The term "antibody" is also intended to encompass mixtures of more than one antibody reactive with the antigen (e.g., a cocktail of different types of monoclonal antibodies reactive with the antigen). The term "antibody" is further intended to encompass whole antibodies, biologically functional fragments thereof, single-chain antibodies, and genetically altered antibodies such as chimeric antibodies comprising portions from more than one species, bifunctional antibodies, antibody conjugates, humanized and human antibodies. Biologically functional antibody fragments, which can also be used, are those peptide fragments derived from an antibody that are sufficient for binding to the antigen. Antibody as used herein is meant to include the entire antibody as well as any antibody fragments (e.g. F(ab').sub.2, Fab', Fab, Fv) capable of binding the epitope, antigen or antigenic fragment of interest.

By "purified antibody" is meant one which is sufficiently free of other proteins, carbohydrates, and lipids with which it is naturally associated. Such an antibody "preferentially binds" to INSP201 polypeptides of the present invention (or an antigenic fragment thereof), i.e., does not substantially recognize and bind to other antigenically unrelated molecules. A purified antibody of the invention is preferably immunoreactive with and immunospecific INSP201 of specific species and more preferably immunospecific for a native human INSP201.

By "binds specifically" is meant high avidity and/or high affinity binding of an antibody to a specific polypeptide i.e., INSP201. Antibody binding to its epitope on this specific polypeptide is preferably stronger than binding of the same antibody to any other epitope. Antibodies which bind specifically to INSP201 may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls.

Preferably, the affinity is at least 1.5-fold, 2-fold, 5-fold 10-fold, 100-fold, $10^3$-fold, $10^4$-fold, $10^5$-fold or $10^6$-fold greater for a polypeptide of the invention than for other member known members of the INSP201 family.

The term "genetically altered antibodies" means antibodies wherein the amino acid sequence has been varied from that of a native antibody. Because of the relevance of recombinant DNA techniques to this invention, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

The term "humanized antibody" or "humanized immunoglobulin" refers to an immunoglobulin comprising a human framework, at least one and preferably all complimentarily determining regions (CDRs) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences. See, e.g. Queen et al., U.S. Pat. Nos. 5,5301,101; 5,585,089; 5,693,762; and 6,180,370 (each of which is incorporated by reference in its entirety).

"Fully humanized antibodies" are molecules containing both the variable and constant region of the human immunoglobulin. Fully humanized antibodies can be potentially used for therapeutic use, where repeated treatments are required for chronic and relapsing diseases such as autoimmune diseases. One method for the preparation of fully human antibodies consist of "humanization" of the mouse humoral immune system, i.e. production of mouse strains able to produce human Ig (Xenomice), by the introduction of human immunoglobulin (Ig) loci into mice in which the endogenous Ig genes have been inactivated. The Ig loci are exceedingly complex in terms of both their physical structure and the gene rearrangement and expression processes required to ultimately produce a broad immune response. Antibody diversity is primarily generated by combinatorial rearrangement between different V, D, and J genes present in the Ig loci. These loci also contain the interspersed regulatory elements, which control antibody expression, allelic exclusion, class switching and affinity maturation. Introduction of unrearranged human Ig transgenes into mice has demonstrated that the mouse recombination machinery is compatible with human genes. Furthermore, hybridomas secreting antigen specific hu-mAbs of various isotypes can be obtained by Xenomice immunisation with antigen.

Fully humanized antibodies and methods for their production are known in the art (Mendez et al., Nature Genetics 15:146-156 (1997); Buggemann et al., Eur. J. Immunol. 21:1323-1326 (1991); Tomizuka et al., Proc. Natl. Acad. Sci. USA 97:722-727 (2000) Patent WO 98/24893.

The term "chimeric antibody" refers to an antibody in which the constant region comes from an antibody of one species (typically human) and the variable region comes from an antibody of another species (typically rodent). Hence, chimeric antibodies are molecules of which different portions are derived from different animal species, such as those having the variable region derived from a murine Mab and a human immunoglobulin constant region. Chimeric antibodies are primarily used to reduce immunogenicity in application and to increase yields in production, for example, where murine Mabs have higher yields from hybridomas but higher immunogenicity in humans, such that human/murine chimeric Mabs are used. Chimeric antibodies and methods for their production are known in the art (Cabilly et al., *Proc. Natl. Acad. Sci. USA* 81:3273-3277 (1984); Morrison et al., *Proc. Natl. Acad. Sci. USA* 81:6851-6855 (1984); Boulianne et al., *Nature* 312:643-646 (1984); Cabilly et al., European Patent Application 125023 (published Nov. 14, 1984); Neuberger et al., *Nature* 314:268-270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., *J. Immunol.* 137:1066-1074 (1986); Robinson et al., International Patent Application No. WO8702671 (published May 7, 1987); Liu et al., *Proc. Natl. Acad. Sci. USA* 84:3439-3443 (1987); Sun et al., *Proc. Natl. Acad. Sci. USA* 84:214-218 (1987); Better et al., *Science* 240:1041-1043 (1988); Riechmann et al., *Nature* 332:323-327. and Harlow and Lane, ANTIBODIES: A LABORATORY MANUAL, supra. These references are entirely incorporated herein by reference.

As used herein, the phrase "antibody fragment" refers to a molecule comprising a portion of an antibody capable of specifically binding an antigen, an antigenic determinant or an epitope. It will be appreciated that Fab and F(ab')2 and other fragments of the antibodies useful in the present invention may be used for the detection and quantitation of their antigens according to the methods disclosed herein for intact antibody molecules. Such fragments are typically produced by proteolytic cleavage, using enzymes such as papain (to produce Fab fragments) or pepsin (to produce F(ab')2 fragments).

As regards the antibodies mentioned herein throughout, the term "monoclonal antibody" is meant to include monoclonal antibodies, chimeric antibodies, fully humanized antibodies, antibodies to anti-idiotypic antibodies (anti-anti-Id antibody) that can be labeled in soluble or bound form, as well as fragments thereof provided by any known technique, such as, but not limited to enzymatic cleavage, peptide synthesis or recombinant techniques. A monoclonal antibody contains a substantially homogeneous population of antibodies specific to antigens, which populations contain substantially similar epitope binding sites. Mabs may be obtained by methods known to those skilled in the art. See, for example Kohler and Milstein, Nature, 256:495-497 (1975); U.S. Pat. No. 4,376, 110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992-1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of Mabs in vivo or in situ makes this the presently preferred method of production. The term "monoclonal antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al., *J. Nucl. Med.* 24:316-325 (1983)).

A monoclonal antibody is said to be "capable of binding" a molecule if it is capable of specifically reacting with the molecule to thereby bind the molecule to the antibody.

An "antigen" is a molecule or a portion of a molecule capable of being bound by an antibody, which antigen is additionally capable of inducing an animal to produce antibody capable of binding to an epitope of that antigen. An antigen may have one or more than one epitope. The specific reaction referred to above is meant to indicate that the antigen will react, in a highly selective manner, with an epitope on its corresponding antibody and not with the multitude of other antibodies which may be evoked by other antigens.

The antibodies, including fragments of antibodies, useful in the present invention may be used to quantitatively or qualitatively detect their antigens in a sample or to detect presence of cells that express their antigens. This can be accomplished by immunofluorescence techniques employing a fluorescently labeled antibody (see below) coupled with fluorescence microscopy, flow cytometric, or fluorometric detection.

The antibodies (or fragments thereof) useful in the present invention may be employed histologically, as in immunofluorescence or immunoelectron microscopy, for in situ detection of their antigens. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the antigens but also its distribution on the examined tissue. Using the present invention, those of ordinary skill will readily perceive that any of wide variety of histological methods (such as staining procedures) can be modified in order to achieve such in situ detection.

Such assays for the antigens typically comprises incubating a biological sample, such as a biological fluid, a tissue extract, freshly harvested cells such as lymphocytes or leukocytes, or cells which have been incubated in tissue culture, in the presence of a labeled antibody capable of identifying the antigens, and detecting the antibody by any of a number of techniques well known in the art.

The biological sample may be coupled to a solid phase support or carrier such as nitrocellulose, or other solid support or carrier which is capable of immobilizing cells, cell particles or soluble proteins. The support or carrier may then be washed with suitable buffers followed by treatment with a labeled antibody in accordance with the present invention, as noted above. The solid phase support or carrier may then be washed with the buffer a second time to remove unbound antibody. The amount of bound label on said solid support or carrier may then be detected by conventional means.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

The antibodies of the invention can be used in connection with immunoaffinity chromatography technology. More specifically, the antibodies can be placed on the surface of a material within a chromatography column. Thereafter, a composition to be purified can be passed through the column. If the sample to be purified includes any INSP201 polypeptides which binds to the antibodies those INSP201 polypeptides will be removed from the sample and thereby purified.

Hence, in summary methods of diagnosis can be performed in vitro using a cellular sample (e.g., blood sample, lymph node biopsy or tissue) from a mammal or can be performed by in vivo imaging.

Compositions comprising the antibodies of the present invention can be used to detect the presence of INSP201, for example, by radioimmunoassay, ELISA, FACS, etc. One or more labeling moieties can be attached to the humanized immunoglobulin. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

An IgG antibody preparation of the present invention may be advantageously purified from an anti-serum of the present invention using protein-G affinity purification, preferably via protein-G immunoprecipitation. An anti-serum derived from an animal immunized, can be used for detecting with optimal sensitivity, via Western immunoblotting analysis, Immunoprecipitation and ELISA, the INSP201 polypeptides.

In general, for applications benefiting from optimal reproducibility, standardization, or precision, a purified antibody or antibody fragment of the present invention capable of specifically binding the target antigen will generally be optimal relative to an unpurified preparation of the present invention.

It will be appreciated by the ordinarily skilled artisan that an antibody or antibody fragment having an affinity characterized by a dissociation constant of up to $10^{-12}$ for a cognate antigen can be obtained using common art techniques.

As described hereinabove, the preparation may advantageously comprise an antibody or antibody fragment attached to any of various types of detectable molecule.

An antibody fragment has the advantage of being smaller than a parental antibody from which it is derived while retaining substantially identical target-antigen binding specificity, or both binding specificity and binding affinity, as the parental antibody. Thus, an antibody fragment, by virtue of being smaller than the parental antibody, will thereby generally have superior biodistribution, and diffusion properties (for example, systemically in-vivo, or in isolated tissues) than the latter. An antibody fragment substantially lacking an Fc region, such as a single-chain Fv, an Fab', an Fab an F(ab')$_2$ or a CDR, is advantageous for applications involving exposure of the preparation to a molecule capable of specifically binding such an Fc region, and in which such binding is undesirable. Typically this may involve an undesired binding of an Fc region exposed to a cognate Fc receptor, or an Fc-binding complement component (for example, complement component Clq, present in serum). Fc receptors are displayed on the surface of numerous immune cell types, including: professional APCs, such as dendritic cells; B lymphocytes; and granulocytes such as neutrophils, basophils, eosinophils, monocytes, macrophages, and mast cells. Thus, the absence of an Fc region from the antibody fragment may be particularly advantageous for avoiding undesired an Fc receptor-mediated immune cell activation or a complement component-mediated complement cascade, particularly when administering the preparation in-vivo to an individual.

An F(ab')$_2$ is a fragment of an antibody molecule containing a divalent antigen-binding portion of an antibody molecule.

An F(ab')$_2$ preparation of the present invention may be conveniently obtained using standard art methods by treating an antibody preparation of the present invention, such as an anti-serum of the present invention, with the enzyme pepsin. The resultant F(ab')$_2$ product is a 5S particle.

An Fab, or Fab' is a fragment of an antibody molecule containing a monovalent antigen-binding portion of an antibody.

The CDR can be generated e.g. as described in EP0585939 or as described by Strandberg et al. (Protein Eng. 2001 January; 14(1): 67-74). The CDR according to the invention can be a modified CDR, which has enhanced effect on the modulation of INSP201polypeptide. An example for methods of modification of active peptides is described by Sawa et al. 1999 (J. Med. Chem. 42, 3289-3299).

An Fab' preparation of the present invention may be conveniently obtained using standard art methods by treating an antibody preparation of the present invention, such as an anti-serum of the present invention, with the enzyme pepsin, followed by reduction of the resultant F(ab')$_2$ into. Such reduction may be effected using a thiol reducing agent, and optionally using a blocking group for the sulffiydryl groups resulting from cleavage of disulfide linkages. Such treatment generates two monovalent 3.5S Fab's an Fc fragment.

An Fab preparation may be conveniently obtained using standard art methods by treating an antibody preparation of the present invention, such as an anti-serum of the present invention, with the enzyme papain to yield the intact light chain and a portion of heavy chain composed of the variable and $C_H1$ domains.

Ample guidance for generating an antibody fragment by enzymatic treatment of an antibody is provided in the literature of the art (for example, refer to: Goldenberg, U.S. Pat. Nos. 4,036,945 and 4,331,647; Porter R R., 1959. Biochem J. 73:119-126).

A single chain Fv (also referred to in the art as "scFv") is a single chain molecule including the variable region of the light chain and the variable region of the heavy chain, linked by a suitable polypeptide linker.

An F(ab')$_2$, Fab', Fab, or single-chain Fv or CDR preparation of the present invention may be obtained using recombinant techniques.

Obtaining a recombinant antibody fragment is effected by isolating mRNA of B lymphocytes of animals immunized with the target antigen, generating cDNA from the mRNA via RT-PCR, and using the cDNA to construct an antibody fragment phage-display library. B lymphocytes can be conveniently isolated from the spleen, or, alternately from the blood, bone-marrow, or lymph nodes of the immunized animal.

It will be appreciated that the above-described methodology can be used to obtain a monoclonal antibody fragment preparation of the present invention having essentially any desired target antigen-binding affinity and/or specificity. Such a preparation can be utilized in various applications benefiting from a reagent capable of binding the target antigen with such defined target antigen-binding characteristics.

Since an Fab' is essentially similar in structure to an Fab, a preparation of the present invention comprising an Fab' may be employed essentially interchangeably with one comprising an Fab, where such Fab' and Fab comprise essentially the same heavy and light chain variable regions. For applications, as will usually be the case, benefiting from a preparation of the present invention comprising an antibody fragment capable of binding the target antigen with maximal affinity, an F(ab')$_2$ preparation of the present invention may superior to an Fab, Fab' or scFv preparation of the present invention, due to the divalent binding of an F(ab')$_2$ to the target antigen relative to the monovalent binding of such a monovalent antibody fragment.

As mentioned hereinabove, depending on the application and purpose, the antibody or antibody fragment preparation may originate from any of various mammalian species An antibody or antibody fragment preparation of the present invention originating from a desired species may be derived from serum of the animal of such species immunized with the target antigen.

A preparation of the present invention of a human or humanized antibody or antibody fragment may be preferable for applications involving administration of the preparation to an individual. For example, a human or humanized antibody or antibody fragment will generally tend to be optimally tolerated immunologically, and hence will display an optimal half-life in-vivo in a human, and will thereby display optimal effectiveness. Further guidance regarding production and exploitation of human or humanized antibodies is provided hereinbelow.

The preparation may be used per se or it can be formulated as an active ingredient in a pharmaceutical composition.

Thus, according to the present invention there is provided a pharmaceutical composition comprising a pharmaceutically acceptable carrier and, as an active ingredient, an antibody or antibody fragment of the present invention.

Methods of formulating the antibody or antibody fragment of the present invention as an active ingredient in a pharmaceutical composition, and methods of exploiting such a pharmaceutical composition are described hereinbelow.

Preferably, administering the antibody or antibody fragment is effected by administering the pharmaceutical composition of the present invention comprising the antibody or antibody fragment of the present invention as an active ingredient.

The antibody or antibody fragment is preferably administered so as to achieve a sufficient level of antibody fragment bound to the target antigen so as to achieve a desired regulation of the biochemical activity.

An ordinarily skilled artisan, such as a physician, more preferably a physician specialized in the disease, will possess the required expertise for determining a suitable therapeutic protocol, including a suitable route of administration, and a suitable dosage of the antibody or antibody fragment for effectively treating the disease according to the teachings of the present invention.

As described hereinabove, the target antigen (i.e. INSP201), which is a polypeptide, may be obtained in various ways.

Preferably, the target antigen is obtained via standard chemical synthesis methodology.

The target antigen may be chemically synthesized using, for example, standard solid phase techniques. Such techniques include exclusive solid phase synthesis, partial solid phase synthesis methods, fragment condensation, classical solution synthesis. Solid phase polypeptide synthesis procedures are well known in the art [for example, refer to Stewart et al., in "Solid Phase Peptide Synthesis", 2nd ed., Pierce Chemical Company, (1984)].

A synthetic polypeptide can be purified by preparative high performance liquid chromatography procedure, such as described by Creighton T. [Proteins, structures and molecular principles, W.H. Freeman and Co. N.Y. (1983)] and its amino acid sequence may be confirmed via standard amino acid sequencing procedures.

As described hereinabove, the preparation is preferably derived by immunizing a mammal with the target antigen.

Generating the preparation in-vivo may be advantageously effected by repeated injection of the target antigen into a mammal in the presence of adjuvant according to a schedule which boosts production of antibodies in the serum. In cases wherein the target antigen is too small to elicit an adequate immunogenic response (referred to as a "hapten" in the art), the hapten can be coupled to an antigenically neutral carrier such as keyhole limpet hemocyanin (KLH) or serum albumin [e.g., bovine serum albumin (BSA)] carriers (for example, refer to U.S. Pat. Nos. 5,189,178 and 5,239,078). Coupling a hapten to a carrier can be effected using various methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as cows, sheeps, mice, rabbits, and the like. Following in-vivo generation of an antibody, its serum titer in the host mammal can readily be measured using immunoassay procedures which are well known in the art.

As described hereinabove, the preparation may advantageously comprise a humanized antibody or antibody fragment.

Humanized antibodies or antibody fragments are genetically engineered chimeric antibodies or antibody fragments having-preferably minimal-portions derived from non human antibodies. Humanized antibodies include antibodies in which complementary determining regions of a human antibody (recipient antibody) are replaced by residues from a complementarity determining region of a non human species (donor antibody) such as mouse, rat or rabbit having the desired functionality. In some instances, Fv framework residues of the human antibody are replaced by corresponding non human residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596). Methods for humanizing non human antibodies or antibody fragments are well known in the art. Generally, a humanized antibody has one or more amino acid residues introduced into it from a source which is non human. These non human amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a non human species. In practice, humanized antibodies may be typically human antibodies in which some complementarity determining region residues and possibly some framework residues are substituted by residues from analogous sites in rodent antibodies. Human antibodies or antibody fragments can also be produced using various techniques known in the art, including phage display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147: 86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368: 812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93).

Antagonistic antibodies targeted to membrane-bound INSP201 are useful for the treatment of inflammation and/or autoimmune disorders.

Agonistic antibodies targeted to membrane-bound INSP201 are useful for the treatment of cancer, HIV and/or EBV and hepatitis B infections.

The activity of antibodies targeted to INSP201 can be demonstrated by the assays and/or animal models as described in Examples 6 to 8.

Preferred nucleic acid molecules of the second and third aspects of the invention are those which encode a polypeptide sequence as recited in SEQ ID NO:2, SEQ ID NO:4, SEQ ID NO:6, SEQ ID NO:8, SEQ ID NO:10, SEQ ID NO:12, SEQ ID NO:14, SEQ ID NO:16, and SEQ ID NO:18 and functionally equivalent polypeptides. These nucleic acid molecules may be used in the methods and applications described herein. The nucleic acid molecules of the invention preferably comprise at least n consecutive nucleotides from the sequences disclosed herein where, depending on the particular sequence, n is 10 or more (for example, 12, 14, 15, 18, 20, 25, 30, 35, 40 or more).

The nucleic acid molecules of the invention also include sequences that are complementary to nucleic acid molecules described above (for example, for antisense or probing purposes).

Nucleic acid molecules of the present invention may be in the form of RNA, such as mRNA, or in the form of DNA, including, for instance cDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphoramidite chemical synthesis, from genomic or cDNA libraries or by separation from an organism. RNA molecules may generally be generated by the in vitro or in vivo transcription of DNA sequences.

The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such as those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation (Nielsen, P. E. et al. (1993) Anticancer Drug Des. 8:53-63).

A nucleic acid molecule which encodes a polypeptide of this invention may be identical to the coding sequence of one or more of the nucleic acid molecules disclosed herein.

These molecules also may have a different sequence which, as a result of the degeneracy of the genetic code, encodes a polypeptide as recited in any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16 or SEQ ID NO:18. Such nucleic acid molecules may include, but are not limited to, the coding sequence for the mature polypeptide by itself; the coding sequence for the mature polypeptide and additional coding sequences, such as those encoding a leader or secretory sequence, such as a pro-, pre- or prepro-polypeptide sequence; the coding sequence of the mature polypeptide, with or without the aforementioned additional coding sequences, together with further additional, non-coding sequences, including non-coding 5' and 3' sequences, such as the transcribed, non-translated sequences that play a role in transcription (including termination signals), ribosome binding and mRNA stability. The nucleic acid molecules may also include additional sequences which encode additional amino acids, such as those which provide additional functionalities.

The nucleic acid molecules of the second and third aspects of the invention may also encode the fragments or the functional equivalents of the polypeptides and fragments of the first aspect of the invention. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide). DNA shuffling by random fragmentation and PCR reassembly of gene fragments and synthetic oligonucleotides are included as techniques which may be used to engineer the nucleotide sequences. Site-directed mutagenesis may be used to insert new restriction sites, alter glycosylation patterns, change codon preference, produce splice variants, introduce mutations and so forth.

Nucleic acid molecules which encode a polypeptide of the first aspect of the invention may be ligated to a heterologous sequence so that the combined nucleic acid molecule encodes a fusion protein. Such combined nucleic acid molecules are included within the second or third aspects of the invention. For example, to screen peptide libraries for inhibitors of the activity of the polypeptide, it may be useful to express, using such a combined nucleic acid molecule, a fusion protein that can be recognised by a commercially-available antibody. A fusion protein may also be engineered to contain a cleavage site located between the sequence of the polypeptide of the invention and the sequence of a heterologous protein so that the polypeptide may be cleaved and purified away from the heterologous protein.

The nucleic acid molecules of the invention also include antisense molecules that are partially complementary to nucleic acid molecules encoding polypeptides of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991).

The term "hybridization" as used here refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. [supra]).

The inhibition of hybridization of a completely complementary molecule to a target molecule may be examined using a hybridization assay, as known in the art (see, for example, Sambrook et al. [supra]). A substantially homologous molecule will then compete for and inhibit the binding of a completely homologous molecule to the target molecule under various conditions of stringency, as taught in Wahl, G. M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC (150 mM NaCl, 15 mM trisodium citrate), 50 mM sodium phosphate (pH7.6), 5×Denhardts solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. (see Sambrook et al. [supra]). Preferably, the conditions used for hybridization are those of high stringency.

Preferred embodiments of this aspect of the invention are nucleic acid molecules that are at least 70% identical over their entire length to a nucleic acid molecule encoding the INSP201 polypeptide and nucleic acid molecules that are substantially complementary to such nucleic acid molecules. Preferably, a nucleic acid molecule according to this aspect of the invention comprises-a region that is at least 80% identical over its entire length to such coding sequences, or is a nucleic acid molecule that is complementary thereto. In this regard, nucleic acid molecules at least 90%, preferably at least 95%, more preferably at least 98%, 99% or more identical over their entire length to the same are particularly preferred. Preferred embodiments in this respect are nucleic acid molecules that encode polypeptides which retain substantially the same biological function or activity as the INSP201 polypeptide.

The invention also provides a process for detecting a nucleic acid molecule of the invention, comprising the steps of: (a) contacting a nucleic probe according to the invention with a biological sample under hybridizing conditions to form duplexes; and (b) detecting any such duplexes that are formed.

As discussed additionally below in connection with assays that may be utilised according to the invention, a nucleic acid molecule as described above may be used as a hybridization probe for RNA, cDNA or genomic DNA, in order to isolate full-length cDNAs and genomic clones encoding the INSP201 polypeptide and to isolate cDNA and genomic clones of homologous or orthologous genes that have a high sequence similarity to the gene encoding this polypeptide.

In this regard, the following techniques, among others known in the art, may be utilised and are discussed below for purposes of illustration. Methods for DNA sequencing and analysis are well known and are generally available in the art and may, indeed, be used to practice many of the embodiments of the invention discussed herein. Such methods may employ such enzymes as the Klenow fragment of DNA polymerase I, Sequenase (US Biochemical Corp, Cleveland, Ohio), Taq polymerase (Perkin Elmer), thermostable T7 polymerase (Amersham, Chicago, Ill.), or combinations of polymerases and proof-reading exonucleases such as those found in the ELONGASE Amplification System marketed by Gibco/BRL (Gaithersburg, Md.). Preferably, the sequencing process may be automated using machines such as the Hamilton Micro Lab 2200 (Hamilton, Reno, Nev.), the Peltier Thermal Cycler (PTC200; ME Research, Watertown, Mass.) and the ABI Catalyst and 373 and 377 DNA Sequencers (Perkin Elmer).

One method for isolating a nucleic acid molecule encoding a polypeptide with an equivalent function to that of the INSP201 polypeptide is to probe a genomic or cDNA library with a natural or artificially-designed probe using standard procedures that are recognised in the art (see, for example, "Current Protocols in Molecular Biology", Ausubel et al. (eds). Greene Publishing Association and John Wiley Interscience, New York, 1989, 1992). Probes comprising at least 15, preferably at least 30, and more preferably at least 50, contiguous bases that correspond to, or are complementary to, nucleic acid sequences from the appropriate encoding gene (SEQ ID NO:1, SEQ ID NO:3, SEQ ID NO:5, SEQ ID NO:7, SEQ ID NO:9, SEQ ID NO:11, SEQ ID NO:13, SEQ ID NO:15 and SEQ ID NO:17), are particularly useful probes. Such probes may be labelled with an analytically-detectable reagent to facilitate their identification. Useful reagents include, but are not limited to, radioisotopes, fluorescent dyes and enzymes that are capable of catalysing the formation of a detectable product. Using these probes, the ordinarily skilled artisan will be capable of isolating complementary copies of genomic DNA, cDNA or RNA polynucleotides encoding proteins of interest from human, mammalian or other animal sources and screening such sources for related sequences, for example, for additional members of the family, type and/or subtype.

In many cases, isolated cDNA sequences will be incomplete, in that the region encoding the polypeptide will be cut short, normally at the 5' end. Several methods are available to obtain full length cDNAs, or to extend short cDNAs. Such sequences may be extended utilising a partial nucleotide sequence and employing various methods known in the art to detect upstream sequences such as promoters and regulatory elements. For example, one method which may be employed is based on the method of Rapid Amplification of cDNA Ends (RACE; see, for example, Frohman et al., PNAS USA 85, 8998-9002, 1988). Recent modifications of this technique, exemplified by the Marathon™ technology (Clontech Laboratories Inc.), for example, have significantly simplified the search for longer cDNAs. A slightly different technique, termed "restriction-site" PCR, uses universal primers to retrieve unknown nucleic acid sequence adjacent a known locus (Sarkar, G. (1993) PCR Methods Applic. 2:318-322). Inverse PCR may also be used to amplify or to extend sequences using divergent primers based on a known region (Triglia, T. et al. (1988) Nucleic Acids Res. 16:8186). Another method which may be used is capture PCR which involves PCR amplification of DNA fragments adjacent a known sequence in human and yeast artificial chromosome DNA (Lagerstrom, M. et al. (1991) PCR Methods Applic., 1, 111-119). Another method which may be used to retrieve unknown sequences is that of Parker, J. D. et al. (1991); Nucleic Acids Res. 19:3055-3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

In one embodiment of the invention, the nucleic acid molecules of the present invention may be used for chromosome localisation. In this technique, a nucleic acid molecule is specifically targeted to, and can hybridize with, a particular location on an individual human chromosome. The mapping of relevant sequences to chromosomes according to the present invention is an important step in the confirmatory correlation of those sequences with the gene-associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationships between genes and diseases that have been mapped to the same chromosomal region are then identified through linkage analysis (coinheritance of physically adjacent genes). This provides valuable information to investigators searching for disease genes using positional cloning or other gene discovery techniques. Once the disease or syndrome has been crudely localised by genetic linkage to a particular genomic region, any sequences mapping to that area may represent associated or regulatory genes for further investigation. The nucleic acid molecule may also be used to detect differences in the chromosomal location due to translocation, inversion, etc. among normal, carrier, or affected individuals.

The nucleic acid molecules of the present invention are also valuable for tissue localisation. Such techniques allow the determination of expression patterns of the polypeptide in tissues by detection of the mRNAs that encode them. These techniques include in situ hybridization techniques and nucleotide amplification techniques, such as PCR. Results from these studies provide an indication of the normal functions of the polypeptide in the organism. In addition, comparative studies of the normal expression pattern of mRNAs with that of mRNAs encoded by a mutant gene provide valuable insights into the role of mutant polypeptides in disease. Such inappropriate expression may be of a temporal, spatial or quantitative nature.

Gene silencing approaches may also be undertaken to down-regulate endogenous expression of a gene encoding a polypeptide of the invention. RNA interference (RNAi) (Elbashir, S M et al., Nature 2001, 411, 494-498) is one method of sequence specific post-transcriptional gene silencing that may be employed. Short dsRNA oligonucleotides are synthesised in vitro and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The vectors of the present invention comprise nucleic acid molecules of the invention and may be cloning or expression vectors. The host cells of the invention, which may be transformed, transfected or transduced with the vectors of the invention may be prokaryotic or eukaryotic.

The polypeptides of the invention may be prepared in recombinant form by expression of their encoding nucleic acid molecules in vectors contained within a host cell. Such expression methods are well known to those of skill in the art and many are described in detail by Sambrook et al. (supra) and Fernandez & Hoeffler (1998, eds. "Gene expression systems. Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the encoding gene can be placed under the control of a control element such as a promoter, ribosome binding site (for bacterial expression) and, optionally, an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid. The vectors pCR4-TOPO, pCR4-TOPO-INSP201, pENTR, pENTR_INSP201EC-6HIS, pEAK12d-PAC, pDEST12.2, pEAK12d-PAC_INSP201EC-6HIS and pDEST12.2_INSP201EC-6HIS are preferred examples of suitable vectors for use in accordance with the aspects of this invention relating to INSP201.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the polypeptides of the invention.

Introduction of nucleic acid molecules encoding a polypeptide of the present invention into host cells can be effected by methods described in many standard laboratory manuals, such as Davis et al., Basic Methods in Molecular Biology (1986) and Sambrook et al., (supra). Particularly suitable methods include calcium phosphate transfection, DEAE-dextran mediated transfection, transfection, microinjection, cationic lipid-mediated transfection, electroporation, transduction, scrape loading, ballistic introduction or infection (see Sambrook et al., 1989 [supra]; Ausubel et al., 1991 [supra]; Spector, Goldman & Leinwald, 1998). In eukaryotic cells, expression systems may either be transient (for example, episomal) or permanent (chromosomal integration) according to the needs of the system.

The encoding nucleic acid molecule may or may not include a sequence encoding a control sequence, such as a signal peptide or leader sequence, as desired, for example, for secretion of the translated polypeptide into the lumen of the endoplasmic reticulum, into the periplasrnic space or into the extracellular environment. These signals may be endogenous to the polypeptide or they may be heterologous signals. Leader sequences can be removed by the bacterial host in post-translational processing.

In addition to control sequences, it may be desirable to add regulatory sequences that allow for regulation of the expression of the polypeptide relative to the growth of the host cell. Examples of regulatory sequences are those which cause the expression of a gene to be increased or decreased in response to a chemical or physical stimulus, including the presence of a regulatory compound or to various temperature or metabolic conditions. Regulatory sequences are those non-translated regions of the vector, such as enhancers, promoters and 5' and 3' untranslated regions. These interact with host cellular proteins to carry out transcription and translation. Such regulatory sequences may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the Bluescript phagemid (Stratagene, LaJolla, Calif.) or pSportl™ plasmid (Gibco BRL) and the like may be used. The baculovirus polyhedrin promoter may be used in insect cells. Promoters or enhancers derived from the genomes of plant cells (for example, heat shock, RUBISCO and storage protein genes) or from plant viruses (for example, viral promoters or leader sequences) may be cloned into the vector. In mammalian cell systems, promoters from mammalian genes or from mammalian viruses are preferable. If it is necessary to generate a cell line that contains multiple copies of the sequence, vectors based on SV40 or EBV may be used with an appropriate selectable marker.

An expression vector is constructed so that the particular nucleic acid coding sequence is located in the vector with the appropriate regulatory sequences, the positioning and orientation of the coding sequence with respect to the regulatory sequences being such that the coding sequence is transcribed under the "control" of the regulatory sequences, i.e., RNA polymerase which binds to the DNA molecule at the control sequences transcribes the coding sequence. In some cases it may be necessary to modify the sequence so that it may be attached to the control sequences with the appropriate orientation; i.e., to maintain the reading frame.

The control sequences and other regulatory sequences may be ligated to the nucleic acid coding sequence prior to insertion into a vector. Alternatively, the coding sequence can be cloned directly into an expression vector that already contains the control sequences and an appropriate restriction site.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, BEK 293, Bowes melanoma and human hepatocellular carcinoma (for example Hep G2) cells and a number of other cell lines.

In the baculovirus system, the materials for baculovirus/insect cell expression systems are commercially available in kit form from, inter alia, Invitrogen, San Diego Calif. (the "MaxBac" kit). These techniques are generally known to those skilled in the art and are described fully in Summers and Smith, Texas Agricultural Experiment Station Bulletin No. 1555 (1987). Particularly suitable host cells for use in this system include insect cells such as *Drosophila* S2 and *Spodoptera* Sf9 cells. There are many plant cell culture and whole plant genetic expression systems known in the art. Examples of suitable plant cellular genetic expression systems include those described in U.S. Pat. No. 5,693,506; U.S. Pat. No. 5,659,122; and U.S. Pat. No. 5,608,143. Additional examples of genetic expression in plant cell culture has been described by Zenk, Phytochemistry 30, 3861-3863 (1991).

In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of particularly preferred bacterial host cells include streptococci, staphylococci, *E. coli, Streptomyces* and *Bacillus subtilis* cells.

Examples of particularly suitable host cells for fungal expression include yeast cells (for example, *S. cerevisiae*) and *Aspergillus* cells.

Any number of selection systems are known in the art that may be used to recover transformed cell lines. Examples include the herpes simplex virus thymidine kinase (Wigler, M. et al. (1977) Cell 11:223-32) and adenine phosphoribosyltransferase (Lowy, I. et al. (1980) Cell 22:817-23) genes that can be employed in tk$^-$ or aprt$^\pm$ cells, respectively.

Also, antimetabolite, antibiotic or herbicide resistance can be used as the basis for selection; for example, dihydrofolate reductase (DHFR) that confers resistance to methotrexate (Wigler, M. et al. (1980) Proc. Natl. Acad. Sci. 77:3567-70); npt, which confers resistance to the aminoglycosides neomycin and G418 (Colbere-Garapin, F. et al. (1981) J. Mol. Biol. 150:1-14) and als or pat, which confer resistance to chlorsulfuron and phosphinotricin acetyltransferase, respectively. Additional selectable genes have been described, examples of which will be clear to those of skill in the art.

Although the presence or absence of marker gene expression suggests that the gene of interest is also present, its presence and expression may need to be confirmed. For example, if the relevant sequence is inserted within a marker gene sequence, transformed cells containing the appropriate sequences can be identified by the absence of marker gene function. Alternatively, a marker gene can be placed in tandem with a sequence encoding a polypeptide of the invention under the control of a single promoter. Expression of the marker gene in response to induction or selection usually indicates expression of the tandem gene as well.

Alternatively, host cells that contain a nucleic acid sequence encoding a polypeptide of the invention and which express said polypeptide may be identified by a variety of procedures known to those of skill in the art. These procedures include, but are not limited to, DNA-DNA or DNA-RNA hybridizations and protein bioassays, for example, fluorescence activated cell sorting (FACS) or immunoassay techniques (such as the enzyme-linked immunosorbent assay [ELISA] and radioimmunoassay [RIA]), that include membrane, solution, or chip based technologies for the detection and/or quantification of nucleic acid or protein (see Hampton, R. et al. (1990) Serological Methods, a Laboratory Manual, APS Press, St Paul, Minn.) and Maddox, D. E. et al. (1983) J. Exp. Med, 158, 1211-1216).

A wide variety of labels and conjugation techniques are known by those skilled in the art and may be used in various nucleic acid and amino acid assays. Means for producing labelled hybridization or PCR probes for detecting sequences related to nucleic acid molecules encoding polypeptides of the present invention include oligolabelling, nick translation, end-labelling or PCR amplification using a labelled polynucleotide. Alternatively, the sequences encoding the polypeptide of the invention may be cloned into a vector for the production of an mRNA probe. Such vectors are known in the art, are commercially available, and may be used to synthesise RNA probes in vitro by addition of an appropriate RNA polymerase such as T7, T3 or SP6 and labelled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)).

Suitable reporter molecules or labels, which may be used for ease of detection, include radionuclides, enzymes and fluorescent, chemiluminescent or chromogenic agents as well as substrates, cofactors, inhibitors, magnetic particles, and the like.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the polypeptides of the present invention.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is particularly useful for purification. Well known techniques for refolding proteins may be employed to regenerate an active conformation when the polypeptide is denatured during isolation and or purification.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as histidine-tryptophan modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the polypeptide of the invention may be used to facilitate purification. One such expression vector provides for expression of a fusion protein containing the polypeptide of the invention fused to several histidine residues preceding a thioredoxin or an enterokinase cleavage site. The histidine residues facilitate purification by IMAC (immobilised metal ion affinity chromatography as described in Porath, J. et al. (1992), Prot. Exp. Purif. 3: 263-281) while the thioredoxin or enterokinase cleavage site provides a means for purifying the polypeptide from the fusion protein. A discussion of vectors which contain fusion proteins is provided in Kroll, D. J. et al. (1993; DNA Cell Biol. 12:441-453).

If the polypeptide is to be expressed for use in screening assays, generally it is preferred that it be produced at the surface of the host cell in which it is expressed. In this event, the host cells may be harvested prior to use in the screening assay, for example using techniques such as fluorescence activated cell sorting (FACS) or immunoaffinity techniques. If the polypeptide is secreted into the medium, the medium can be recovered in order to recover and purify the expressed polypeptide. If polypeptide is produced intracellularly, the cells must first be lysed before the polypeptide is recovered.

As indicated above, the present invention also provides novel targets and methods for the screening of drug candidates or leads. These screening methods include binding assays and/or functional assays, and may be performed in vitro, in cell systems or in animals.

In this regard, a particular object of this invention resides in the use of an INSP201 polypeptide as a target for screening candidate drugs for treating or preventing cell surface glycoprotein related disorders.

Another object of this invention resides in methods of selecting biologically active compounds, said methods comprising contacting a candidate compound with a INSP201 gene or polypeptide, and selecting compounds that bind said gene or polypeptide.

A further other object of this invention resides in methods of selecting biologically active compounds, said method comprising contacting a candidate compound with recombinant host cell expressing a INSP201 polypeptide with a candidate compound, and selecting compounds that bind said INSP201 polypeptide at the surface of said cells and/or that modulate the activity of the INSP201 polypeptide.

A "biologically active" compound denotes any compound having biological activity in a subject, preferably therapeutic activity, more preferably a compound having cell surface glycoprotein activity, and further preferably a compound that can be used for treating INSP201 related disorders, or as a lead to develop drugs for treating cell surface glycoprotein related disorders. A "biologically active" compound preferably is a compound that modulates the activity of INSP201.

The above methods may be conducted in vitro, using various devices and conditions, including with immobilized reagents, and may further comprise an additional step of assaying the activity of the selected compounds in a model of cell surface glycoprotein related disorder, such as an animal model.

Preferred selected compounds are agonists of INSP201, i.e., compounds that can bind to INSP201 and mimic the activity of an endogenous ligand thereof.

A further object of this invention resides in a method of selecting biologically active compounds, said method comprising contacting in vitro a test compound with a INSP201 polypeptide according to the present invention and determining the ability of said test compound to modulate the activity of said INSP201 polypeptide.

A further object of this invention resides in a method of selecting biologically active compounds, said method comprising contacting in vitro a test compound with a INSP201 gene according to the present invention and determining the ability of said test compound to modulate the expression of said INSP201 gene, preferably to stimulate expression thereof.

In another embodiment, this invention relates to a method of screening, selecting or identifying active compounds, particularly compounds active in regulating inflammation, cell degeneration and apoptosis, and oncogenesis, the method comprising contacting a test compound with a recombinant host cell comprising a reporter construct, said reporter construct comprising a reporter gene under the control of a INSP201 gene promoter, and selecting the test compounds that modulate (e.g. stimulate or reduce, preferably stimulate) expression of the reporter gene.

The polypeptide of the invention can be used to screen libraries of compounds in any of a variety of drug screening techniques. Such compounds may activate (agonise) or inhibit (antagonise) the level of expression of the gene or the activity of the polypeptide of the invention and form a further aspect of the present invention. Preferred compounds are effective to alter the expression of a natural gene which encodes a polypeptide of the first aspect of the invention or to regulate the activity of a polypeptide of the first aspect of the invention.

Agonist or antagonist compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al., Current Protocols in Immunology 1(2):Chapter 5 (1991).

Binding to a target gene or polypeptide provides an indication as to the ability of the compound to modulate the activity of said target, and thus to affect a pathway leading to cell surface glycoprotein related disorder in a subject. The determination of binding may be performed by various techniques, such as by labelling of the candidate compound, by competition with a labelled reference ligand, etc. For in vitro binding assays, the polypeptides may be used in essentially pure form, in suspension, immobilized on a support, or expressed in a membrane (intact cell, membrane preparation, liposome, etc.).

Modulation of activity includes, without limitation, stimulation of the surface expression of the INSP201 receptor, modulation of multimerization of said receptor (e.g., the formation of multimeric complexes with other sub-units), etc. The cells used in the assays may be any recombinant cell (i.e., any cell comprising a recombinant nucleic acid encoding a INSP201 polypeptide) or any cell that expresses an endogenous INSP201 polypeptide. Examples of such cells include, without limitation, prokaryotic cells (such as bacteria) and eukaryotic cells (such as yeast cells, mammalian cells, insect cells, plant cells, etc.). Specific examples include *E. coli, Pichia pastoris, Hansenula polymorpha, Schizosaccharomyces pombe, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from fibroblasts, embryonic cells, epithelial cells, nervous cells, adipocytes, etc.).

Compounds that are most likely to be good antagonists are molecules that bind to the polypeptide of the invention without inducing the biological effects of the polypeptide upon binding to it. Potential antagonists include small organic molecules, peptides, polypeptides and antibodies that bind to the polypeptide of the invention and thereby inhibit or extinguish its activity. In this fashion, binding of the polypeptide to normal cellular binding molecules may be inhibited, such that the normal biological activity of the polypeptide is prevented.

The polypeptide of the invention that is employed in such a screening technique may be free in solution, affixed to a solid support, borne on a cell surface or located intracellularly. In general, such screening procedures may involve using appropriate cells or cell membranes that express the polypeptide that are contacted with a test compound to observe binding, or stimulation or inhibition of a functional response. The functional response of the cells contacted with the test compound is then compared with control cells that were not contacted with the test compound. Such an assay may assess whether the test compound results in a signal generated by activation of the polypeptide, using an appropriate detection system. Inhibitors of activation are generally assayed in the presence of a known agonist and the effect on activation by the agonist in the presence of the test compound is observed.

A preferred method for identifying an agonist or antagonist compound of a polypeptide of the present invention comprises:
(a) contacting a cell expressing (optionally on the surface thereof) the polypeptide according to the first aspect of the invention, the polypeptide being associated with a second component capable of providing a detectable signal in response to the binding of a compound to the polypeptide, with a compound to be screened under conditions to permit binding to the polypeptide; and
(b) determining whether the compound binds to and activates or inhibits the polypeptide by measuring the level of a signal generated from the interaction of the compound with the polypeptide.

Methods for generating detectable signals in the types of assays described herein will be known to those of skill in the art. A particular example is cotransfecting a construct expressing a polypeptide according to the invention, or a fragment such as the LBD, in fusion with the GAL4 DNA binding domain, into a cell together with a reporter plasmid, an example of which is pFR-Luc (Stratagene Europe, Amsterdam, The Netherlands). This particular plasmid contains a synthetic promoter with five tandem repeats of GAL4 binding sites that control the expression of the luciferase gene. When a potential ligand is added to the cells, it will bind the GAL4-polypeptide fusion and induce transcription of the luciferase gene. The level of the luciferase expression can be monitored by its activity using a luminescence reader (see, for example, Lehman et al. JBC 270, 12953, 1995; Pawar et al. JBC, 277, 39243, 2002).

A further preferred method for identifying an agonist or antagonist of a polypeptide of the invention comprises:
(a) contacting a labelled or unlabeled compound with the polypeptide immobilized on any solid support (for example beads, plates, matrix support, chip) and detection of the compound by measuring the label or the presence of the compound itself; or
(b) contacting a cell expressing on the surface thereof the polypeptide, by means of artificially anchoring it to the cell membrane, or by constructing a chimeric receptor being associated with a second component capable of providing a detectable signal in response to the binding of a compound to the polypeptide, with a compound to be screened under conditions to permit binding to the polypeptide; and
(c) determining whether the compound binds to and activates or inhibits the polypeptide by comparing the level of a signal generated from the interaction of the compound with the polypeptide with the level of a signal in the absence of the compound.

For example, a method such as FRET detection of ligand bound to the polypeptide in the presence of peptide co-activators (Norris et al, Science 285, 744, 1999) might be used.

A further preferred method for identifying an agonist or antagonist of a polypeptide of the invention comprises:
(a) contacting a cell expressing (optionally on the surface thereof) the polypeptide, the polypeptide being associated with a second component capable of providing a detectable signal in response to the binding of a compound to the polypeptide, with a compound to be screened under conditions to permit binding to the polypeptide; and
(b) determining whether the compound binds to and activates or inhibits the polypeptide by comparing the level of a signal generated from the interaction of the compound with the polypeptide with the level of a signal in the absence of the compound.

In further preferred embodiments, the general methods that are described above may further comprise conducting the identification of agonist or antagonist in the presence of labelled or unlabelled ligand for the polypeptide.

In another embodiment of the method for identifying agonist or antagonist of a polypeptide of the present invention comprises:
determining the inhibition of binding of a ligand to cells which express a polypeptide of the invention (and which optionally have a polypeptide of the invention on the surface thereof), or to cell membranes containing such a polypeptide, in the presence of a candidate compound under conditions to permit binding to the polypeptide, and determining the amount of ligand bound to the polypeptide. A compound capable of causing reduction of binding of a ligand is considered to be an agonist or antagonist. Preferably the ligand is labelled.

More particularly, a method of screening for a polypeptide antagonist or agonist compound comprises the steps of:
(a) incubating a labelled ligand with a whole cell expressing a polypeptide according to the invention, optionally on the cell surface, or a cell membrane containing a polypeptide of the invention,
(b) measuring the amount of labelled ligand bound to the whole cell or the cell membrane;
(c) adding a candidate compound to a mixture of labelled ligand and the whole cell or the cell membrane of step (a) and allowing the mixture to attain equilibrium;
(d) measuring the amount of labelled ligand bound to the whole cell or the cell membrane after step (c); and
(e) comparing the difference in the labelled ligand bound in step (b) and (d), such that the compound which causes the reduction in binding in step (d) is considered to be an agonist or antagonist.

Similarly, there is provided a method of screening for a polypeptide antagonist or agonist compound which comprises the steps of:
(a) incubating a labelled ligand with a polypeptide according to the invention on any solid support or the cell surface, or a cell membrane containing a polypeptide of the invention.
(b) measuring the amount of labelled ligand bound to the polypeptide on the solid support, whole cell or the cell membrane;
(c) adding a candidate compound to a mixture of labelled ligand and immobilized polypeptide on the solid support, the whole cell or the cell membrane of step (a) and allowing the mixture to attain equilibrium;
(d) measuring the amount of labelled ligand bound to the immobilized polypeptide or the whole cell or the cell membrane after step (c); and
(e) comparing the difference in the labelled ligand bound in step (b) and (d), such that the compound which causes the reduction in binding in step (d) is considered to be an agonist or antagonist.

The INSP201 polypeptide of the present invention may modulate cellular growth and differentiation. Thus, the biological activity of the INSP201 polypeptide can be examined in systems that allow the study of cellular growth and differentiation such as organ culture assays or in colony assay systems in agarose culture. Stimulation or inhibition of cellular proliferation may be measured by a variety of assays.

For example, for observing cell growth inhibition, one can use a solid or liquid medium. In a solid medium, cells undergoing growth inhibition can easily be selected from the subject cell group by comparing the sizes of colonies formed. In a liquid medium, growth inhibition can be screened by measuring culture medium turbity or incorporation of labelled thymidine in DNA. Typically, the incorporation of a nucleoside analog into newly synthesised DNA may be employed to measure proliferation (i.e., active cell growth) in a population of cells. For example, bromodeoxyuridine (BrdU) can be employed as a DNA labelling reagent and anti-BrdU mouse monoclonal antibodies can be employed as a detection reagent. This antibody binds only to cells containing DNA which has incorporated bromodeoxyuridine. A number of detection methods may be used in conjunction with this assay including immunofluorescence, immunohistochemical, ELISA, and colorimetric methods. Kits that include bromodeoxyuridine (BrdU) and anti-BrdU mouse monoclonal antibody are commercially available from Boehringer Mannheim (Indianapolis, Ind.).

The effect of the INSP201 polypeptide upon cellular differentiation can be measured by contacting stem cells or embryonic cells with various amounts of the INSP201 polypeptide and observing the effect upon differentiation of the stem cells or embryonic cells. Tissue-specific antibodies and microscopy may be used to identify the resulting cells.

The INSP201 polypeptide may also be found to modulate immune and/or nervous system cell proliferation and differentiation in a dose-dependent manner in the above-described assays. Thus, the "functional equivalents" of the INSP201 polypeptide include polypeptides that exhibit any of the same growth and differentiation regulating activities in the above-described assays in a dose-dependent manner. Although the degree of dose-dependent activity need not be identical to that of the INSP201 polypeptide, preferably the "functional equivalents" will exhibit substantially similar dose-dependence in a given activity assay compared to the INSP201 polypeptide.

In certain of the embodiments described above, simple binding assays may be used, in which the adherence of a test compound to a surface bearing the polypeptide is detected by means of a label directly or indirectly associated with the test compound or in an assay involving competition with a labelled competitor. In another embodiment, competitive drug screening assays may be used, in which neutralising antibodies that are capable of binding the polypeptide specifically compete with a test compound for binding. In this manner, the antibodies can be used to detect the presence of any test compound that possesses specific binding affinity for the polypeptide.

Assays may also be designed to detect the effect of added test compounds on the production of mRNA encoding the polypeptide in cells. For example, an ELISA may be constructed that measures secreted or cell-associated levels of polypeptide using monoclonal or polyclonal antibodies by standard methods known in the art, and this can be used to search for compounds that may inhibit or enhance the production of the polypeptide from suitably manipulated cells or tissues. The formation of binding complexes between the polypeptide and the compound being tested may then be measured.

Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

Still further techniques of this kind will be apparent to those skilled in the art. See, for example, Adessi C. & Soto C. Curr. Med. Chem. 2002, 9(9):963-78; Strand F. L. Prog. Drug Res., 2003 61:1-37; Hruby V. J. Nat. Rev. Drug Discov. 2002, 1(11):847-58.

The polypeptide of the invention may be used to identify membrane-bound or soluble receptors, through standard receptor binding techniques that are known in the art, such as ligand binding and crosslinking assays in which the polypeptide is labelled with a radioactive isotope, is chemically modified, or is fused to a peptide sequence that facilitates its detection or purification, and incubated with a source of the putative receptor (for example, a composition of cells, cell membranes, cell supernatants, tissue extracts, or bodily fluids). The efficacy of binding may be measured using biophysical techniques such as surface plasmon resonance and spectroscopy. Binding assays may be used for the purification and cloning of the receptor, but may also identify agonists and antagonists of the polypeptide, that compete with the binding of the polypeptide to its receptor. Standard methods for conducting screening assays are well understood in the art.

In another embodiment, this invention relates to the use of a INSP201 polypeptide or fragment thereof, whereby the fragment is preferably a INSP201 gene-specific fragment, for isolating or generating an agonist or stimulator of the INSP201 polypeptide for the treatment of an immune related disorder, wherein said agonist or stimulator is selected from the group consisting of:
1. a specific antibody or fragment thereof including: a) a chimeric, b) a humanized or c) a fully human antibody, as well as;
2. a bispecific or multispecific antibody,
3. a single chain (e.g. scFv) or
4. single domain antibody, or
5. a peptide- or non-peptide mimetic derived from said antibodies or
6. an antibody-mimetic such as a) an anticalin or b) a fibronectin-based binding molecule (e.g. trinectin or adnectin).

The generation of peptide- or non-peptide mimetics from antibodies is known in the art (Saragovi et al., 1991 and Saragovi et al., 1992).

Anticalins are also known in the art (Vogt et al., 2004). Fibronectin-based binding molecules are described in U.S. Pat. No. 6,818,418 and WO2004029224.

Furthermore, the test compound may be of various origin, nature and composition, such as any small molecule, nucleic acid, lipid, peptide, polypeptide including an antibody such as a chimeric, humanized or fully human antibody or an antibody fragment, peptide- or non-peptide mimetic derived therefrom as well as a bispecific or multispecific antibody, a single chain (e.g. scFv) or single domain antibody or an antibody-mimetic such as an anticalin or fibronectin-based binding molecule (e.g. trinectin or adnectin), etc., in isolated form or in mixture or combinations.

The invention also includes a screening kit useful in the methods for identifying agonists, antagonists, ligands, receptors, substrates, enzymes, that are described above.

The invention includes the agonists, antagonists, ligands, receptors, substrates and enzymes, and other compounds which modulate the activity or antigenicity of the polypeptide of the invention discovered by the methods that are described above.

As mentioned above, it is envisaged that the various moieties of the invention (i.e. the polypeptides of the first aspect of the invention, a nucleic acid molecule of the second or third aspect of the invention, a vector of the fourth aspect of the invention, a host cell of the fifth aspect of the invention, a ligand of the sixth aspect of the invention, a compound of the seventh aspect of the invention) may be useful in the therapy or diagnosis of diseases. To assess the utility of the moieties of the invention for treating or diagnosing a disease one or more of the following assays may be carried out. Note that although some of the following assays refer to the test compound as being a protein/polypeptide, a person skilled in the art will readily be able to adapt the following assays so that the other moieties of the invention may also be used as the "test compound".

The invention also provides pharmaceutical compositions comprising a polypeptide, nucleic acid, ligand or compound of the invention in combination with a suitable pharmaceutical carrier. These compositions may be suitable as therapeutic or diagnostic reagents, as vaccines, or as other immunogenic compositions, as outlined in detail below.

According to the terminology used herein, a composition containing a polypeptide, nucleic acid, ligand or compound [X] is "substantially free of" impurities [herein, Y] when at least 85% by weight of the total X+Y in the composition is X. Preferably, X comprises at least about 90% by weight of the total of X+Y in the composition, more preferably at least about 95%, 98% or even 99% by weight.

The pharmaceutical compositions should preferably comprise a therapeutically effective amount of the polypeptide, nucleic acid molecule, ligand, or compound of the invention. The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 50 mg/kg, preferably 0.05 mg/kg to 10 mg/kg. Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intraarterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

If the activity of the polypeptide of the invention is in excess in a particular disease state, several approaches are available. One approach comprises administering to a subject an inhibitor compound (antagonist) as described above, along with a pharmaceutically acceptable carrier in an amount effective to inhibit the function of the polypeptide, such as by blocking the binding of ligands, substrates, enzymes, receptors, or by inhibiting a second signal, and thereby alleviating the abnormal condition. Preferably, such antagonists are antibodies. Most preferably, such antibodies are chimeric and/or humanised to minimise their immunogenicity, as described previously.

In another approach, soluble forms of the polypeptide that retain binding affinity for the ligand, substrate, enzyme, receptor, in question, may be administered. Typically, the polypeptide may be administered in the form of fragments that retain the relevant portions.

In an alternative approach, expression of the gene encoding the polypeptide can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the gene encoding the polypeptide. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes. Such oligonucleotides may be administered or may be generated in situ from expression in vivo.

In addition, expression of the polypeptide of the invention may be prevented by using ribozymes specific to its encoding mRNA sequence. Ribozymes are catalytically active RNAs that can be natural or synthetic (see for example Usman, N, et al., Curr. Opin. Struct. Biol (1996) 6(4), 527-33). Synthetic ribozymes can be designed to specifically cleave mRNAs at selected positions thereby preventing translation of the mRNAs into functional polypeptide. Ribozymes may be synthesised with a natural ribose phosphate backbone and natural bases, as normally found in RNA molecules. Alternatively the ribozymes may be synthesised with non-natural backbones, for example, 2'-O-methyl RNA, to provide protection from ribonuclease degradation and may contain modified bases.

RNA molecules may be modified to increase intracellular stability and half-life. Possible modifications include, but are not limited to, the addition of flanking sequences at the 5' and/or 3' ends of the molecule or the use of phosphorothioate or 2'-O-methyl rather than phosphodiesterase linkages within the backbone of the molecule. This concept is inherent in the production of PNAs and can be extended in all of these molecules by the inclusion of non-traditional bases such as inosine, queosine and butosine, as well as acetyl-, methyl-, thio- and similarly modified forms of adenine, cytidine, guanine, thymine and uridine which are not as easily recognised by endogenous endonucleases.

For treating abnormal conditions related to an under-expression of the polypeptide of the invention and its activity, several approaches are also available. One approach comprises administering to a subject a therapeutically effective amount of a compound that activates the polypeptide, i.e., an agonist as described above, to alleviate the abnormal condition. Alternatively, a therapeutic amount of the polypeptide in combination with a suitable pharmaceutical carrier may be administered to restore the relevant physiological balance of polypeptide.

Gene therapy may be employed to effect the endogenous production of the polypeptide by the relevant cells in the subject. Gene therapy is used to treat permanently the inappropriate production of the polypeptide by replacing a defective gene with a corrected therapeutic gene.

Gene therapy of the present invention can occur in vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus as described by Berkner, K. L., in Curr. Top. Microbiol. Immunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. For example, a nucleic acid molecule encoding a polypeptide of the invention may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

In situations in which the polypeptides or nucleic acid molecules of the invention are disease-causing agents, the invention provides that they can be used in vaccines to raise antibodies against the disease causing agent.

Vaccines according to the invention may either be prophylactic (i.e. to prevent infection) or therapeutic (i.e. to treat disease after infection). Such vaccines comprise immunising antigen(s), immunogen(s), polypeptide(s), protein(s) or nucleic acid, usually in combination with pharmaceutically-acceptable carriers as described above, which include any carrier that does not itself induce the production of antibodies harmful to the individual receiving the composition. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, and other pathogens.

Since polypeptides may be broken down in the stomach, vaccines comprising polypeptides are preferably administered parenterally (for instance, subcutaneous, intramuscular, intravenous, or intradermal injection). Formulations suitable for parenteral administration include aqueous and non-aqueous sterile injection solutions which may contain antioxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

Genetic delivery of antibodies that bind to polypeptides according to the invention may also be effected, for example, as described in International patent application WO98/55607.

The technology referred to as jet injection (see, for example, www.powderject.com) may also be useful in the formulation of vaccine compositions.

A number of suitable methods for vaccination and vaccine delivery systems are described in International patent application WO00/29428.

This invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified enzymatically by using PCR, ligase chain reaction (LCR), strand displacement amplification (SDA), or other amplification techniques (see Saiki et al., Nature, 324, 163-166 (1986); Bej, et al., Crit. Rev. Biochem. Molec. Biol., 26, 301-334 (1991); Birkenmeyer et al., J. Virol. Meth., 35, 117-126 (1991); Van Brunt, J., Bio/Technology, 8, 291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:
a) contacting a sample of tissue from the patient with a nucleic acid probe under stringent conditions that allow the formation of a hybrid complex between a nucleic acid molecule of the invention and the probe;
b) contacting a control sample with said probe under the same conditions used in step a);
c) and detecting the presence of hybrid complexes in said samples;
wherein detection of levels of the hybrid complex in the patient sample that differ from levels of the hybrid complex in the control sample is indicative of disease.

A further aspect of the invention comprises a diagnostic method comprising the steps of:
a) obtaining a tissue sample from a patient being tested for disease;
b) isolating a nucleic acid molecule according to the invention from said tissue sample; and
c) diagnosing the patient for disease by detecting the presence of a mutation in the nucleic acid molecule which is associated with disease.

To aid the detection of nucleic acid molecules in the above-described methods, an amplification step, for example using PCR, may be included.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mismatched duplexes by RNase digestion or by assessing differences in melting temperatures. The presence or absence of the mutation in the patient may be detected by contacting DNA with a nucleic acid probe that hybridises to the DNA under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)). For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230:

1242). Sequence changes at specific locations may also be revealed by nuclease protection assays, such as RNase and S1 protection or the chemical cleavage method (see Cotton et al., Proc. Natl. Acad. Sci. USA (1985) 85: 4397-4401).

In addition to conventional gel electrophoresis and DNA sequencing, mutations such as microdeletions, aneuploidies, translocations, inversions, can also be detected by in situ analysis (see, for example, Keller et al., DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al., Science, 250, 559-562 (1990), and Trask et al., Trends, Genet., 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al); Lockhart, D. J. et al. (1996) Nat. Biotech. 14: 1675-1680); and Schena, M. et al. (1996) Proc. Natl. Acad. Sci. 93: 10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jet application apparatus, as described in PCT application WO95/25116 (Baldeschweiler et al). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis and ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA, RIA, and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation The amount of standard complex formation may be quantified by various methods, such as by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, with a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:
(a) a nucleic acid molecule of the present invention;
(b) a polypeptide of the present invention; or
(c) a ligand of the present invention.

In one aspect of the invention, a diagnostic kit may comprise a first container containing a nucleic acid probe that hybridises under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to disease in which members of cell surface glycoprotein family are implicated. Such diseases may include cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; respiratory tract disorders, including chronic obstructive pulmonary disease and cystic fibrosis; developmental disorders; metabolic disorders including diabetes mellitus, osteoporosis, and obesity, AIDS and renal disease; infections including viral infection, bacterial infection, fungal infection and parasitic infection and other pathological conditions. Preferably, the diseases are those in which lymphocyte antigens are implicated. Such kits may also be used for the detection of reproductive disorders including infertility.

Various aspects and embodiments of the present invention will now be described in more detail by way of example, with particular reference to the INSP201 polypeptide.

It will be appreciated that modification of detail may be made without departing from the scope of the invention.

According to the invention, antagonists of soluble INSP201 (e.g. INSP201-EC) or agonists of membrane-bound INSP201 (e.g. agonistic antibodies) can be administered alone or in combination with several other therapeutic regimens or anti-cancer agents (e.g. multiple drug regimen) to obtain an additive or synergistic effect for the treatment and/or prevention of cancer, HIV and/or EBV and hepatitis B infections.

The anti-cancer agent is selected from platinum compounds such as cisplatin and carboplatin, vinca alkaloids such as vinorelbine, vincristine and vinblastine, taxines such as docetaxel and paclitaxel, various topoisomerase inhibitors, IL-2 and interferon-α.

According to the invention, agonists of soluble INSP201 (e.g. INSP201-EC) or antagonists of membrane-bound INSP201 (e.g. antagonistic antibodies) can be administered alone or in combination with several other therapeutic regimens or agents (e.g. multiple drug regimen) to obtain an additive or synergistic effect for the treatment and/or prevention of inflammation and/or autoimmune diseases.

The anti-inflammatory agent is selected among interferon-beta, cyclosporine A, tacrolimus and sirolimus.

BRIEF DESCRIPTION OF THE FIGURES

FIG. 1: Glycosylation site prediction for INSP201 (SEQ ID NO: 8) using NetNGlyc 1.0. Potential N-Glycosylation sites may be found at positions 124, 156, 188, 204, 220 and 268 of SEQ ID NO: 8.

FIG. 2: INSP201 cDNA and protein sequence (SEQ ID NO: 52). The position of PCR primers used for cloning is indicated by arrows. The predicted extracellular domain is highlighted.

FIG. 3: Nucleotide sequence with translation of the INSP201EC PCR product (SEQ ID NO: 53).

FIG. 4: Taqman analysis of INSP201-EC for major tissues collection (table 2)

TABLE 1

Figure 5:
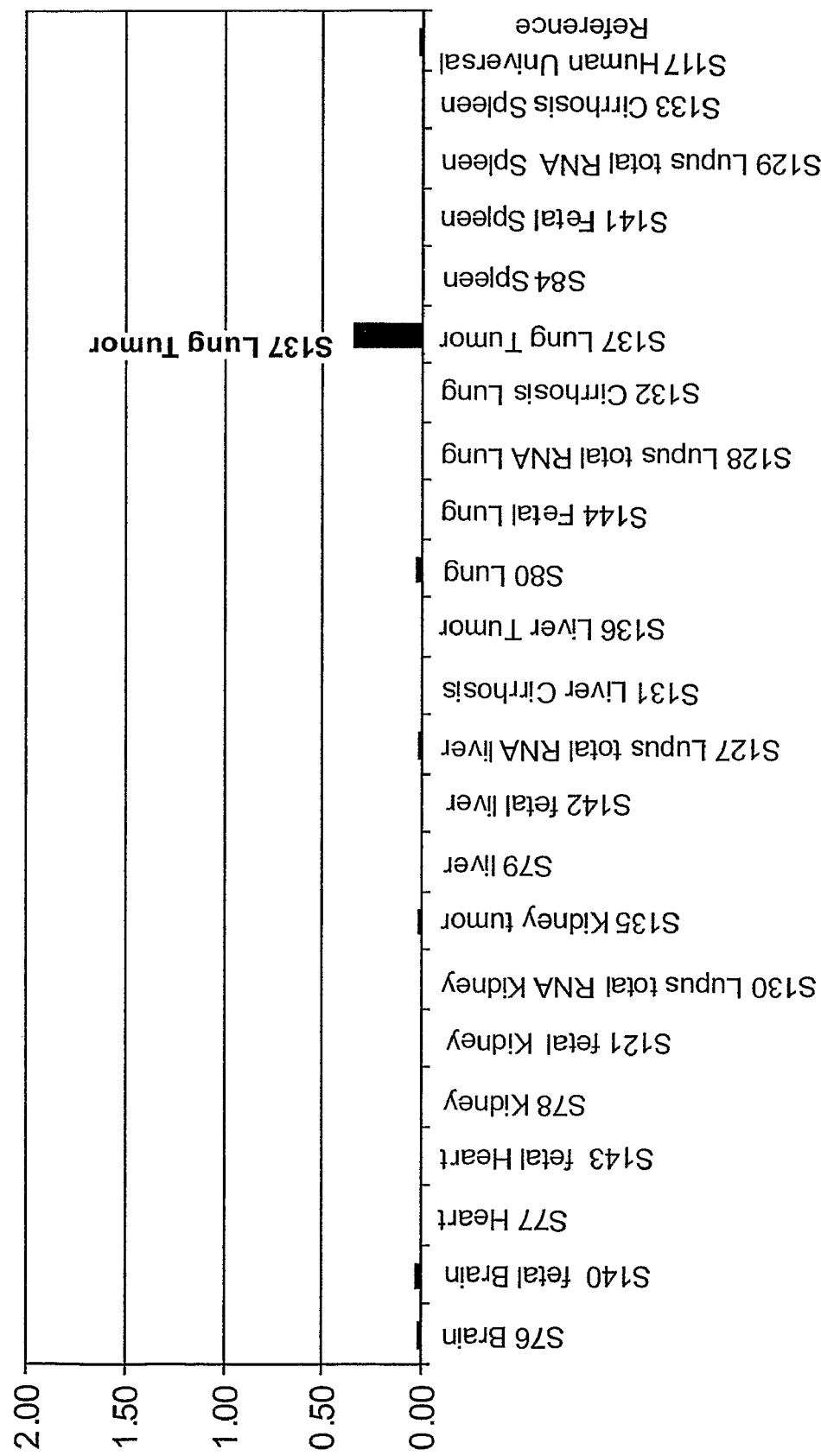
FIG. 5: Taqman analysis of INSP201-EC for comparative tissues (table 3)

| Amino Acid | Synonymous Groups | More Preferred Synonymous Groups |
| --- | --- | --- |
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE 2

| Amino Acid | Synonymous Groups |
| --- | --- |
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-.Met, D-Ile, Orn, D-Orn |
| Leu | D-Leu, Val, D-Val, AdaA, AdaG, Leu, D-Leu, Met, D-Met |
| Pro | D-Pro, L-I-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenylproline, AdaA, AdaG, cis-3,4, or 5-phenyl-proline, Bpa, D-Bpa |
| Tyr | D-Tyr, Phe, D-Phe, L-Dopa, His, D-His |
| Cys | D-Cys, S--Me--Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |
| Lys | D-Lys, Arg, D-Arg, homo-Arg, D-homo-Arg, Met, D-Met, Ile, D-Ile, Orn, D-Orn |
| Asp | D-Asp, D-Asn, Asn, Glu, D-Glu, Gln, D-Gln |
| Glu | D-Glu, D-Asp, Asp, Asn, D-Asn, Gln, D-Gln |
| Met | D-Met, S--Me--Cys, Ile, D-Ile, Leu, D-Leu, Val, D-Val |

EXAMPLE 1

Identification and In Silico Analysis of INSP201

As described above, the INSP201 polypeptide is predicted to function as a cell surface glycoprotein. The SignalP-NN output for INSP201 shows that the protein comprises a leader sequence that is thought to be cleaved between positions 21 and 22 of the sequence (Nielsen, H. et al. 1997, Protein Engineering, 10, 1-6; Nielsen, H., and Krogh, A.: Prediction of signal peptides and signal anchors by a hidden Markov model. In Proceedings of the Sixth International Conference on Intelligent Systems for Molecular Biology (ISMB 6), AAAI Press, Menlo Park, Calif., pp. 122-130 (1998)). The presence of a leader sequence is consistent with the INSP201 protein functioning as a secreted protein.

TMHMM results for INSP201 indicate that the polypeptide contains a transmembrane domain between residues 406-428 inclusive. TMHMM is a database that predicts transmembrane domains based on known secondary structures.

FIG. 1 shows the NetNGlyc (version 1.0)(http://www.cbs.dtu.dk/services/NetNGlyc/) results for INSP201. NetGlyc is a program based on a neural network algorithm trained to identify the consensus sequence for N-linked glycosylation, Asn-Xaa-Ser/Thr (where Xaa is not Pro), and the surrounding sequence context, in an attempt to discriminate between acceptor and non-acceptor sequons. Glycosylation is an important post-translational modification, and is known to influence protein folding, localisation and trafficking, protein solubility, antigenicity, biological activity and half-life, as well as cell-cell interactions.

On the basis of these experiments and the INSP201 sequence information provided herein, it is now possible to design experiments to detect the presence of the INSP201 transcript across a range of human tissue types to determine its tissue expression. In addition, it will be possible to design experiments to detect the presence of the INSP201 transcript across a range of normal and diseased tissues in order to establish more particularly the relevance of the INSP201 protein in a pathological context.

At the same time, the cloning of the INSP201 gene from human genomic DNA will allow the high level expression of the INSP201 protein in prokaryotic or eukaryotic expression systems and its subsequent purification and characterisation. For example, recombinant INSP201 may be used to generate INSP201-specific monoclonal or polyclonal antibodies which might then be used in the further biochemical characterisation of INSP201.

Alternatively, recombinant INSP201 may be used in a wide variety of screening assays, including those described above.

EXAMPLE 2

Work is now underway to clone the gene encoding the INSP201 polypeptide. This may involve the preparation of human cDNA templates, for example, from a variety of normal human tissue total RNA samples (which can be purchased from Clontech, Stratagene, Ambion, Biochain Institute and prepared in-house) using an enzyme such as Superscript II RNase H—Reverse Transcriptase (Invitrogen). Human cDNA libraries (in bacteriophage lambda (λ) vectors) can be purchased from Clontech, Invitrogen, or made in-house in λ GT10 vectors. Pairs of specific PCR primers can be designed for amplifying the complete coding sequence of the virtual cDNA using software such as the Primer Designer Software (Scientific & Educational Software, PO Box 72045, Durham, N.C. 27722-2045, USA). Pairs of specific PCR primers may also be designed for amplifying the DNA sequence of each predicted exon using the same software. These isolated DNA fragments may be assembled in the desired order using cloning vectors, PCR reactions and/or DNA restriction/ligation reactions. PCR primers were optimized to have a Tm close to 55+10 0 C. and a GC content of 40-60%. Primers should be selected which have high selectivity for the target sequence (INSP201) with little or no non-specific priming. PCR can then be used to amplify the gene sequence of interest. Procedures necessary for cloning of the sequence, such as sub-cloning of PCR products, colony PCR, plasmid DNA preparation and sequencing and finally construction of mammalian cell expression vectors are known in the art (see, for example, WO03/055913).

Further experiments may then be performed to determine the tissue distribution and expression levels of the INSP201 polypeptide in vivo, on the basis of the nucleotide and amino acid sequences disclosed herein.

For example, the presence of the transcripts for INSP201 may be investigated by PCR of cDNA from different human tissues. The INSP201 transcript may be present at very low levels in the samples tested. Therefore, extreme care is needed in the design of experiments to establish the presence of a transcript in various human tissues as a small amount of genomic contamination in the RNA preparation will provide a false positive result. Thus, all RNA should be treated with DNAse prior to use for reverse transcription. In addition, for each tissue a control reaction may be set up in which reverse transcription was not undertaken (a-ve RT control).

For example, 1 µg of total RNA from each tissue may be used to generate cDNA using Multiscript reverse transcriptase (ABI) and random hexamer primers. For each tissue, a control reaction is set up in which all the constituents are added except the reverse transcriptase (-ve RT control). PCR reactions are set up for each tissue on the reverse transcribed RNA samples and the minus RT controls. INSP201 specific primers may readily be designed on the basis of the sequence information provided herein. The presence of a product of the correct molecular weight in the reverse transcribed sample together with the absence of a product in the minus RT control may be taken as evidence for the presence of a transcript in that tissue. Any suitable cDNA libraries may be used to screen for the INSP201 transcript, not only those generated as described above.

The tissue distribution pattern of the INSP201 polypeptide will provide further useful information in relation to the function of those polypeptides.

Furthermore, overexpression or knock-down of the expression of the polypeptides in cell lines may be used to determine the effect on transcriptional activation of the host cell genome. Dimerisation partners, co-activators and co-repressors of the INSP201 polypeptide may be identified by immunoprecipitation combined with Western blotting and immunoprecipitation combined with mass spectroscopy.

EXAMPLE 3

Cloning of INSP201 Extracellular Domain

INSP201 is predicted to be a single-pass transmembrane protein with an un-annotatable extracellular domain (N terminal) and a conserved intracellular domain (possibly involved in signalling). It is a full length prediction for an 518 amino acid protein (1554 bp) encoded in 3 exons. The predicted extracellular domain is encoded by the first 405 amino acids (1215 bp). All but the 3'-most 32 bp of the extracellular domain is encoded in exon 1 of the prediction.

A pair of PCR primers (INSP201-CP1/INSP201-CP2) (FIG. 2) was designed to amplify a 1215 bp product containing the entire predicted extracellular domain of the prediction. The INSP210-CP2 reverse PCR primer was 51 bp long and contained a 19 bp overlap with the 3' end of exon 1 as well as the 32 bp of the extracellular domain encoded in exon 2. These primers were used in PCR with genomic DNA as the template. The INSP201-CP2 primer would amplify exon 1 and simultaneously add the 32 bp of exon 2 onto the PCR product. The PCR products were visualised on a gel and a band of the predicted size was purified and cloned into the pCR4-TOPO cloning vector.

Sequence analysis identified a clone which contained the INSP201 extracellular domain sequence. This clone is plasmid pCR4-TOPO-INSP201-EC.

3.1 Gene Specific Cloning Primers for PCR

A pair of PCR primers (INSP201-CP1 and INSP201-CP2, Table 3) were designed for amplifying a 1215 bp product containing the predicted coding sequence of the virtual cDNA using Primer Designer Software (Scientific & Educational Software, PO Box 72045, Durham, N.C. 27722-2045, USA). Primers were selected which had high selectivity for the target sequence (INSP201).

3.2 PCR of INSP201 Extracellular Domain from Genomic DNA

The majority of the predicted extracellular domain of INSP201 was comprised of a single exon and thus could be amplified from genomic DNA. The 32 bp of the extracellular domain encoded in exon 2 were included in the INSP201-CP2 reverse PCR primer, which also contained a 19 bp overlap with the 3' end of exon 1. PCR was performed using gene-specific cloning primers INSP201-CP1/INSP201-CP2 and genomic DNA as the template in a final volume of 50 µl containing 1× Platinum® Taq High Fidelity (HiFi) buffer, 2 mM MgSO$_4$, 200 µM dNTPs, 0.2 µM of each cloning primer, 1 unit of Platinum® Taq DNA Polymerase High Fidelity (HiFi) (Invitrogen), 100 ng of genomic DNA (Novagen Inc.), and either 0×, 1× or 2×PCR$_x$ Enhancer solution (Invitrogen). Cycling was performed using an MJ Research DNA Engine, programmed as follows: 94° C., 2 min; 35 cycles of 94° C., 30 sec, 68° C., 1 min 30 sec; followed by 1 cycle at 68° C. for 78 min and a holding cycle at 4° C.

The amplification products were visualized on 0.8% agarose gel in 1×TAE buffer (Invitrogen). PCR products of the expected molecular weight (1215 bp) were purified from the gel using the MinElute DNA Purification System (Qiagen), eluted in 10 µl of EB buffer (10 mM Tris.Cl, pH 8.5) and subcloned directly.

3.3 Subcloning of PCR Products

The PCR product was subcloned into the topoisomerase I modified cloning vector (pCR4-TOPO) using the TA cloning kit purchased from the Invitrogen Corporation using the conditions specified by the manufacturer. Briefly, 4 µl of gel purified PCR product was incubated for 15 min at room temperature with 1 µl of TOPO vector and 1 µl salt solution. The reaction mixture was then transformed into *E. coli* strain TOP10 (Invitrogen) as follows: a 50 µl aliquot of One Shot TOP10 cells was thawed on ice and 2 µl of TOPO reaction was added. The mixture was incubated for 15 min on ice and then heat shocked by incubation at 42° C. for exactly 30 s. Samples were returned to ice and 250 µl of warm (room temperature) SOC media was added. Samples were incubated with shaking (220 rpm) for 1 h at 37° C. The total volume of the transformation mixture was then plated on L-broth (LB) plates containing ampicillin (100 µg/ml) and incubated overnight at 37° C.

3.4 Colony PCR

Colonies were inoculated into 50 µl sterile water using a sterile toothpick. A 10 µl aliquot of the inoculum was then subjected to PCR in a total reaction volume of 20 µl containing 1× AmpliTaq™ buffer, 200 µM dNTPs, 20 pmoles of T7 primer, 20 pmoles of T3 primer, and 1 unit of AmpliTaq™ (Applied Biosystems) using an MJ Research DNA Engine. The cycling conditions were as follows: 94° C., 2 min; 30 cycles of 94° C., 30 sec, 48° C., 30 sec and 72° C. for 1 min 30 sec. Samples were maintained at 4° C. (holding cycle) before further analysis.

PCR products were analyzed on 1% agarose gels in 1×TAE buffer. Colonies which gave PCR products of approximately the expected molecular weight (1215 bp+105 bp due to the multiple cloning site (MCS)) were grown up overnight at 37° C. in 5 ml L-Broth (LB) containing ampicillin (100 µg/ml), with shaking at 220 rpm.

3.5 Plasmid DNA Preparation and Sequencing

Miniprep plasmid DNA was prepared from the 5 ml culture using a Biorobot 8000 robotic system (Qiagen) or Wizard Plus SV Minipreps kit (Promega cat. no. 1460) according to the manufacturer's instructions. Plasmid DNA was eluted in 80 µl of sterile water. The DNA concentration was measured using a Spectramax 190 photometer (Molecular Devices). Plasmid DNA (200-500 ng) was subjected to DNA sequencing with the T7 and T3 primers, and the gene-specific primers INSP201-SP1 and INSP201-SP2, using the BigDye Terminator system (Applied Biosystems cat. no. 4390246) according to the manufacturer's instructions. The primer sequence is shown in Table 3. Sequencing reactions were purified using Dye-Ex columns (Qiagen) or Montage SEQ 96 cleanup plates (Millipore cat. no. LSKS09624) then analyzed on an Applied Biosystems 3700 sequencer.

Sequence analysis identified a clone which contained a 100% match to the predicted INSP201 extracellular domain sequence at the amino acid level. The sequence of the cloned cDNA fragment is shown in FIG. 3. The cloned PCR product is in plasmid pCR4-TOPO-INSP201-EC.

3.6 Construction of Mammalian Cell Expression Vectors for INSP201-EC

Plasmid pCR4-TOPO-INSP201-EC was used as PCR template to generate pEAK12d and pDEST12.2 expression clones containing the INSP201-EC ORF sequence with a 3' sequence encoding a 6HIS tag using the Gateway™ cloning methodology (Invitrogen).

3.7 Generation of Gateway Compatible INSP201-EC ORF Fused to an in Frame 6HIS Tag Sequence The first stage of the Gateway cloning process involves a two step PCR reaction which generates the ORF of INSP201-EC flanked at the 5' end by an attB1 recombination site and Kozak sequence, and flanked at the 3' end by a sequence encoding an in-frame 6 histidine (6HIS) tag, a stop codon and the attB2 recombination site (Gateway compatible cDNA).

The first PCR reaction (in a final volume of 50 µl) contains respectively: 1 µl (30 ng) of plasmid pCR4—TOPO-INSP201-EC, 1.5 µl dNTPs (10 mM), 10 µl of 10× Pfx polymerase buffer, 1 µl MgSO$_4$ (50 mM), 0.5 µl each of gene specific primer (100 µM) (INSP201EC-EX1 and INSP201EC-EX2), and 0.5 µl Platinum Pfx DNA polymerase (Invitrogen). The PCR reaction was performed using an initial denaturing step of 95° C. for 2 min, followed by 12 cycles of 94° C. for 15 s; 55° C. for 30 s and 68° C. for 2 min; and a holding cycle of 4° C. The amplification product was directly purified using the Wizard PCR Preps DNA Purification System (Promega) and recovered in 50 µl sterile water according to the manufacturer's instructions.

The second PCR reaction (in a final volume of 50 µl) contained 10 µl purified PCR1 product, 1.5 µl dNTPs (10 mM), 5 µl of 10× Pfx polymerase buffer, 1 µl MgSO$_4$ (50 mM), 0.5 µl of each Gateway conversion primer (100 µM) (GCP forward and GCP reverse) and 0.5 µl of Platinum Pfx DNA polymerase. The conditions for the 2nd PCR reaction were: 95° C. for 1 min; 4 cycles of 94° C., 15 sec; 50° C., 30 sec and 68° C. for 2 min; 25 cycles of 94° C., 15 sec; 55° C., 30 sec and 68° C., 2 min; followed by a holding cycle of 4° C.

A 10 μl aliquot was visualized on 0.8% agarose gel in 1×TAE buffer (Invitrogen) in order to verify that the product was of the expected molecular weight (1215+70=1285 bp). The remaining 40 μl were loaded on 0.8% agarose gel in 1×TAE buffer gel and the band was purified using the Wizard PCR Preps DNA Purification System (Promega) and recovered in 50 μl sterile water according to the manufacturer's instructions.

3.8 Subcloning of Gateway Compatible INSP201-EC ORF into Gateway Entry Vector pDONR221 and Expression Vectors pEAK12d-PAC and pDEST12.2

The second stage of the Gateway cloning process involves subcloning of the Gateway modified PCR product into the Gateway entry vector pDONR221 (Invitrogen) as follows: 5 μl of purified product from PCR2 were incubated with 1.5 μl pDONR221 vector (0.1 μg/μl), 2 μl BP buffer and 1.5 μl of BP clonase enzyme mix (Invitrogen) in a final volume of 10 μl at RT for 1 h. The reaction was stopped by addition of proteinase K 1 μl (2 μg/μl) and incubated at 37° C. for a further 10 min. An aliquot of this reaction (1 μl) was used to transform *E. coli* DH10B cells by electroporation as follows: a 25 μl aliquot of DH10B electrocompetent cells (Invitrogen) was thawed on ice and 1 μl of the BP reaction mix was added. The mixture was transferred to a chilled 0.1 cm electroporation cuvette and the cells electroporated using a BioRad Gene-Pulser™ according to the manufacturer's recommended protocol. SOC media (0.5 ml) which had been pre-warmed to room temperature was added immediately after electroporation. The mixture was transferred to a 15 ml snap-cap tube and incubated, with shaking (220 rpm) for 1 h at 37° C. Aliquots of the transformation mixture (10 μl and 50 μl) were then plated on L-broth (LB) plates containing kanamycin (40 μg/ml) and incubated overnight at 37° C.

Plasmid miniprep DNA was prepared from 5 ml culture from 8 of the resultant colonies using a Qiaprep BioRobot 8000 system (Qiagen). Plasmid DNA (150-200 ng) was subjected to DNA sequencing with 21M13 and M13Rev primers as well with gene specific INSP201-319F-SP1 and INSP201-570F-SP1 sequencing primers as described above using the BigDyeTerminator system (Applied Biosystems cat. no. 4336919) according to the manufacturer's instructions. The primer sequences are shown in Table 3. Sequencing reactions were purified using Montage SEQ 96 cleanup plates (Millipore cat. no. LSKS09624) then analyzed on an Applied Biosystems 3700 sequencer.

Plasmid eluate (2 μl or approx. 150 ng) from the clone which contained the INSP201-EC-6HIS insert (pENTR_INSP201-EC-6HIS) was then used in a recombination reaction containing 1.5 μl of either pEAK12d-PAC vector or pDEST12.2 vector (0.1 μg/μl), 2 μl LR buffer and 1.5 μl of LR clonase (Invitrogen) in a final volume of 10 μl. The mixture was incubated at RT for 1 h, stopped by addition of proteinase K 1 μl (2 μg/μl) and incubated at 37° C. for a further 10 min. An aliquot of this reaction (1 μl) was used to transform *E. coli* DH10B cells by electroporation as follows: a 25 μl aliquot of DH10B electrocompetent cells (Invitrogen) was thawed on ice and 1 μl of the LR reaction mix was added. The mixture was transferred to a chilled 0.1 cm electroporation cuvette and the cells electroporated using a BioRad Gene-Pulser™ according to the manufacturer's recommended protocol. SOC media (0.5 ml) which had been pre-warmed to room temperature was added immediately after electroporation. The mixture was transferred to a 15 ml snap-cap tube and incubated, with shaking (220 rpm) for 1 h at 37° C. Aliquots of the transformation mixture (10 μl and 50 μl) were then plated on L-broth (LB) plates containing ampicillin (100 μg/ml) and incubated overnight at 37° C.

Plasmid mini-prep DNA was prepared from 5 ml cultures from 6 of the resultant colonies subcloned in each vector using a Qiaprep BioRobot 8000 system (Qiagen). Plasmid DNA (200-500 ng) in the pEAK12d-PAC vector was subjected to DNA sequencing with pEAK12F and pEAK12R primers as well with gene specific INSP201-319F-SP1 and INSP201-570F-SP1 sequencing primers as described above. Plasmid DNA (200-500 ng) in the pDEST12.2 vector was subjected to DNA sequencing with 21M13 and M13Rev primers as well with gene specific sequencing primers described above. Primer sequences are shown in Table 3.

CsCl gradient purified maxi-prep DNA was prepared from a 500 ml culture of the sequence verified clone (pEAK12d-PAC_INSP201-EC-6H1S) using the method described by Sambrook J. et al., 1989 (in Molecular Cloning, a Laboratory Manual, $2^{nd}$ edition, Cold Spring Harbor Laboratory Press), Plasmid DNA was resuspended at a concentration of 1 μg/μl in sterile water (or 10 mM Tris-HCl pH 8.5) and stored at −20° C.

Endotoxin-free maxi-prep DNA was prepared from a 500 ml culture of the sequence verified clone (pDEST12.2_INSP201-EC-6HIS) using the EndoFree Plasmid Mega kit (Qiagen) according to the manufacturer's instructions. Purified plasmid DNA was resuspended in endotoxin free TE buffer at a final concentration of at least 3 μg/μl and stored at −20° C.

TABLE 3

INSP201 cloning and sequencing primers

| Primer | Sequence (5'-3') |
| --- | --- |
| INSP201-CP1 | ATG AAA TCA TTC AGC CGG ATC CTC TTC CTC GTC TTC CTC (SEQ ID NO: 32) |
| INSP201-CP2 | TGC GCC ACG TGG TCG CCC CAC CAG AGT CAC GCC GGT CTC CTT CAC TCG CTC (SEQ ID NO: 33) |
| INSP201EC-EX1 | GCA GGC TTC GCC ACC ATG AAA TCA TTC AGC CGG AT (SEQ ID NO: 34) |
| INSP201EC-EX2 | *TG ATG GTG ATG GTG* TGC GCC ACG TGG TCG CCC CAC (SEQ ID NO: 35) |
| INSP201-319F-SP1 | GCT GAC TCA CTC ACA ACC TCAA (SEQ ID NO: 36) |
| INSP201-570F-SP2 | TGA AGT CTC ACA GGC AGA AC (SEQ ID NO: 37) |
| GCP Forward | G GGG ACA AGT TTG TAC AAA AAA GCA GGC TTC GCC ACC (SEQ ID NO: 38) |
| GCP Reverse | GGG GAC CAC TTT GTA CAA GAA AGC TGG GTT TCA *ATG GTG ATG GTG ATG GTG* (SEQ ID NO: 39) |
| pEAK12F | GCC AGC TTG GCA CTT GAT GT (SEQ ID NO: 40) |
| pEAK12R | GAT GGA GGT GGA CGT GTC AG (SEQ ID NO: 41) |
| 21M13 | TGT AAA ACG ACG GCC AGT (SEQ ID NO: 42) |
| M13REV | CAG GAA ACA GCT ATG ACC (SEQ ID NO: 43) |
| T7 | TAA TAC GAC TCA CTA TAG G (SEQ ID NO: 44) |

TABLE 3-continued

INSP201 cloning and sequencing primers

| Primer | Sequence (5'-3') |
|---|---|
| T3 | ATT AAC CCT CAC TAA AGG (SEQ ID NO: 45) |

Underlined sequence = Kozak sequence
Bold = Stop codon
*Italic* sequence = His tag

EXAMPLE 4

Functional Genomics Expression in Mammalian Cells and Purification of the Cloned, His-Tagged Plasmid pEAK12d-PAC_INSP201-EC-6HIS Human Embryonic Kidney 293 cells expressing the Epstein-Barr virus Nuclear Antigen (HEK293-EBNA, Invitrogen) were maintained in suspension in Ex-cell VPRO serum-free medium (seed stock, maintenance medium, JRH). Cells are inoculated at $1 \times 10^6$ cells/ml in 250 ml FEME (DMEM/Ham's F-12 1:1 19 mM HEPES, 5 g/L Glucose, 7.5 mM L-Glutamine, 4 ml/L ITS-X) (all Invitrogen-Life Technologies) medium supplemented with 1% FCS. For the transfection-mix 500 µg DNA (pEAK12d-PAC_INSP201-EC-6HIS) plus 10 µg reporter-gene DNA is diluted in 50 ml FEME 1% FCS. Then 1 ml PEI (1 mg/l Polysciences, USA) is added. This mix is incubated for 10 minutes at room temperature. After 10 minutes the transfection mix is added to the cells and the culture is incubated at 37° C. in the incubator for 90 min. Finally the volume is topped up with the remaining 200 ml FEME 1% FCS containing 2.5 ml Pen-Strep to prevent contamination due to non-sterility of DNA. Confirmation of positive transfection was done by qualitative fluorescence examination at day 6 (Axiovert 10 Zeiss). On day 6 (harvest day), supernatant (500 ml) was centrifuged (4° C., 400 g) and placed into a pot bearing a unique identifier.

4.1 Purification Process

The 500 ml culture medium sample containing the recombinant protein with a C-terminal 6His tag was diluted with one volume cold buffer A (50 mM $NaH_2PO_4$; 600 mM NaCl; 8.7% (w/v) glycerol, pH 7.5) to a final volume of 1000 ml. The sample was filtered through a 0.22 µm sterile filter (Millipore, 500 ml filter unit) and kept at 4° C. in a 1 litre sterile square media bottle (Nalgene).

The purification was performed at 4° C. on a VISION workstation (Applied Biosystems) connected to an automatic sample loader (Labomatic). The purification procedure was composed of two sequential steps, metal affinity chromatography on a Poros 20 MC (Applied Biosystems) column charged with Ni ions (10×50 mm, 3.93 ml), followed by buffer exchange on a Sephadex G-25 medium (Amersham Pharmacia) gel filtration column (1.0×15 cm).

For the first chromatography step the metal affinity column was regenerated with 30 column volumes of EDTA solution (100 mM EDTA; 1 M NaCl; pH 8.0), recharged with Ni ions through washing with 15 column volumes of a 100 mM $NiSO_4$ solution, washed with 10 column volumes of buffer A, followed by 7 column volumes of buffer B (50 mM $NaH_2PO_4$; 600 mM NaCl; 8.7% (w/v) glycerol, 400 mM; imidazole, pH 7.5), and finally equilibrated with 15 column volumes of buffer A containing 15 mM imidazole. The sample was transferred, by the Labomatic sample loader, into a 200 ml sample loop and subsequently charged onto the Ni metal affinity column at a flow rate of 20 ml/min. The charging procedure was repeated 5 times in order to transfer the entire sample (1000 ml) onto the Ni column. Subsequently the column was washed with 12 column volumes of buffer A, followed by 28 column volumes of buffer A containing 20 mM imidazole. During the 20 mM imidazole wash loosely attached contaminating proteins were eluted of the column. The recombinant His-tagged protein was finally eluted with 10 column volumes of buffer B at a flow rate of 2 ml/min, and the eluted protein was collected in a 2.7 ml fraction.

For the second chromatography step, the Sephadex G-25 gel-filtration column was regenerated with 2 ml of buffer D (1.137 M NaCl; 2.7 mM KCl; 1.5 mM $KH_2PO_4$; 8 mM $Na_2HPO_4$; pH 7.2), and subsequently equilibrated with 4 column volumes of buffer C (137 mM NaCl; 2.7 mM KCl; 1.5 mM $KH_2PO_4$; 8 mM $Na_2HPO_4$; 20% (w/v) glycerol; pH 7.4). The peak fraction eluted from the Ni-column was automatically, through the integrated sample loader on the VISION, loaded onto the Sephadex G-25 column and the protein was eluted with buffer C at a flow rate of 2 ml/min. The desalted sample was recovered in a 2.7 ml fraction. The fraction was filtered through a 0.22 µm sterile centrifugation filter (Millipore), aliquoted, frozen and stored at −80° C. An aliquot of the sample was analyzed on SDS-PAGE (4-12% NuPAGE gel; Novex) by Coomassie blue staining and Western blot with anti-His antibodies.

4.2 Coomassie Blue Staining

The NuPAGE gel was stained in a 0.1% coomassie blue R250 staining solution (30% methanol, 10% acetic acid) at room temperature for 1 h and subsequently destained in 20% methanol, 7.5% acetic acid until the background was clear and the protein bands clearly visible.

4.3 Western Blot

Following the electrophoresis the proteins were electrotransferred from the gel to a nitrocellulose membrane at 290 mA for 1 hour at 4° C. The membrane was blocked with 5% milk powder in buffer E (137 mM NaCl; 2.7 mM KCl; 1.5 mM $KH_2PO_4$; 8 mM $Na_2HPO_4$; 0.1% Tween 20, pH 7.4) for 1 h at room temperature, and subsequently incubated with a mixture of 2 rabbit polyclonal anti-His antibodies (G-18 and H-15, 0.2 ug/ml each; Santa Cruz) in 2.5% milk powder in buffer E overnight at 4° C. After further 1 hour incubation at room temperature, the membrane was washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane was developed with the ECL kit (Amersham) for 1 min. The membrane was subsequently exposed to a Hyperfilm (Amersham), the film developed and the Western blot image visually analyzed.

EXAMPLE 5

Analysis of INSP201 Gene Expression Levels by TaqMan Analysis

Real-time PCR was carried using SYBR green chemistry on the ABI PRISM 7700 Sequence Detection System. Pairs of PCR primers were designed such that the product would span an intron of the sequence being analysed. The expression levels of the products were determined in a panel of RT-PCR products made from RNA samples using random primers.

Total RNA from each sample was reverse transcribed using the Superscript III First-Strand Synthesis System for RT-PCR (Invitrogen, Cat. No. 18080-051) in a final reaction volume of 20 µl. 2 µg of total RNA was combined with 50 ng random hexamer primers, 10 mM each of dATP, dGTP, dCTP, & dTTP, and DEPC-treated water in a volume of 10 μl. The mixture was incubated at 65° C. for 5 min then chilled on ice for 1 min. The following 10 μl cDNA synthesis mix was prepared in a separate tube: 2 μl 10×RT buffer, 4 μl 25 mM MgCl$_2$, 2 μl 0.1M DTT, 1 μl RnaseOUT™ (40 units/μl), and 1 μl SuperScript™ III RT enzyme (200 units/μl). The cDNA synthesis mix was added to the RNA/primer mixture, mixed gently and incubated at 25° C. for 10 min then at 50° C. for 50 min. The RT enzyme was then inactivated by incubating at 85° C. for 5 min. The mixture was chilled on ice and then 1 μl of E. coli Rnase H (2 units/μl) was added and the mixture incubated at 37° C. for 20 min. The mixture was chilled on ice and then diluted 1/250 with sterile water. Dilutions of the reverse transcriptase reaction were then subjected to real time PCR analysis on a TaqMan instrument (PE Biosystems 7700).

SYBR Green Real Time PCR primers for human INSP201-EC and glyceraldehyde 3-phosphate dehydrogenase GAPDH (house-keeping control) were designed using the Primer Express software from PE Biosystems according to the sequences as follows: INSP201-EC (with a pair which spans the boundary between exon 1 and 2), Reverse 5'-TCGCCCCACCAGAGTCAC-3' (SEQ ID NO:46); forward 5'-CCGAGGTGAGGGAGTCAACA-3' (SEQ ID NO: 47); GAPDH, reverse 5'-GATGGGATTTCCATTGATGACA-3' (SEQ ID NO: 48); forward 5'-CCACCCATGGCAAATTCC-3' (SEQ ID NO: 49); intron-GAPDH, reverse 5'-CCTAGTCCCAGGGCTTTGATT-3' (SEQ ID NO: 50); forward 5'-CTGTGCTCCCACTCCTGATTTC-3' (SEQ ID NO: 51). The specificity and the optimal primer concentration were tested on plasmid pCR4-TOPO-INSP201-EC. Potential genomic DNA contamination was excluded by performing PCR reactions with specific GAPDH intronic primers. The absence of non-specific amplification was confirmed by analyzing the PCR products on a 3.5% agarose gel electrophoresis to ensure a single band of the expected molecular weight was produced.

SYBR Green Real-Time PCR was performed with 5 μl/well of RT-products, 25 μl/well of SYBR Green PCR master mix (PE Biosystem) with AmpErase Uracil N-Glycosylase (UNG) (0.5 Unit/well) and 20 μl of primers (300 nM). PCR was performed at 50° C. for 2 min (for AmpErase UNG incubation to remove any uracil incorporated into the cDNA), 95° C. for 10 min (for AmpliTaq Gold activation) and then run for 40 cycles at 95° C. for 15 sec, 60° C. for 1 min on the ABI PRISM 7700 Detection System. The reverse-transcribed cDNA samples were thus amplified and their Ct (cycle threshold) values were determined. All Ct values were normalized to the housekeeping gene GAPDH. A single specific DNA band for INSP201-EC and GAPDH was observed using gel electrophoresis analysis. The principle of real-time detection using the SYBR Green PCR master mix is based upon the direct detection of PCR product by measuring the increase in fluorescence caused by the binding of SYBR Green dye to double-stranded DNA. The difference in expression level between GAPDH and INSP201-EC in each cDNA sample was expressed as a difference in Ct value, i.e. Delta (δ) Ct=Ct (GAPDH)−Ct (INSP201-EC). Results for each sample were then expressed as a fold difference in the number of cycles required for detectable INSP201-EC expression relative to that for GAPDH, according to the formula Fold Difference=$2^{(-\delta Ct)}$. Finally, the expression level of INSP201-EC in each cDNA sample was shown relative to the GAPDH gene expression level, where GAPDH expression level=100%, by dividing 100 by the Fold Difference for INSP201-EC. Results are shown in table 4 to 9.

TABLE 4

| major human tissues | Relative to GAPDH (=100) |
|---|---|
| S76 Brain | 0.01 |
| S77 Heart | 0.00 |
| S78 Kidney | 0.00 |
| S79 liver | 0.00 |
| S80 Lung | 0.00 |
| S81 Placenta | 0.00 |
| S82 skeletal Muscle | 0.00 |
| S83 small intestine | 0.00 |
| S84 Spleen | 0.01 |
| S85 Thymus | 0.00 |
| S86 Uterus | 0.02 |
| S89 Spinal cord | 0.00 |
| S90 Cervix | 0.03 |
| S91 colon | 0.00 |
| S92 ovary | 0.01 |
| S93 prostate | 0.02 |
| S94 testis | 0.00 |
| S95 skin | 0.01 |
| S113 pancreas | 0.33 |
| S119 Breast | 0.01 |
| S120 Stomach | 0.00 |
| S122 Eye | 0.00 |
| S147 Bladder | 0.00 |

TABLE 5

| Comparative tissues | Relative to GAPDH (=100) |
|---|---|
| S76 Brain | 0.01 |
| S140 fetal Brain | 0.03 |
| S77 Heart | 0.00 |
| S143 fetal Heart | 0.00 |
| S78 Kidney | 0.00 |
| S121 fetal Kidney | 0.01 |
| S130 Lupus total RNA Kidney | 0.00 |
| S135 Kidney tumor | 0.01 |
| S79 liver | 0.00 |
| S142 fetal liver | 0.00 |
| S127 Lupus total RNA liver | 0.01 |
| S131 Liver Cirrhosis | 0.00 |
| S136 Liver Tumor | 0.00 |
| S80 Lung | 0.03 |
| S144 Fetal Lung | 0.00 |
| S128 Lupus total RNA Lung | 0.00 |
| S132 Cirrhosis Lung | 0.00 |
| S137 Lung Tumor | 0.34 |
| S84 Spleen | 0.00 |
| S141 Fetal Spleen | 0.00 |
| S129 Lupus total RNA Spleen | 0.00 |
| S133 Cirrhosis Spleen | 0.00 |
| S117 Human Universal Reference | 0.01 |

TABLE 6

| Secretory and immune tissues | Relative to GAPDH (=100) |
|---|---|
| S87 Bone Marrow | 0.02 |
| S88 Thyroid | 0.03 |
| S115 Salivary Gland | 0.00 |
| S116 Adrenal Gland | 0.00 |
| S123 Mammary gland | 0.01 |
| S125 Pituitary Gland | 0.00 |
| S145 Lymph Node | 0.02 |
| S146 Adipose | 0.02 |
| S148 Appendix | 0.00 |
| S149 Blood vessel Artery | 0.00 |
| S150 Throat | 0.00 |
| S75 Tonsil | 0.06 |
| S54 Stroma | 0.01 |
| S153 cells HDMEC | 0.00 |

TABLE 6-continued

| Secretory and immune tissues | Relative to GAPDH (=100) |
|---|---|
| S157 cells HDMEC stimulated | #REF! |
| S155 cell HAoEC | 0.00 |
| S158 cell HAoEC stimulated | 0.00 |
| S11 RA2 | 0.06 |
| S12 RA3 | 0.00 |

TABLE 7

| Primary cells and cell lines (non-leukocytic) | Relative to GAPDH (=100) |
|---|---|
| S1 AG1518 fibroblast | 0.00 |
| S2 Howard Ab | 0.09 |
| S3 Clark N | 0.00 |
| S4 NF1 | 0.20 |
| S5 NF2 | 0.19 |
| S6 SScN2 | 0.00 |
| S7 SSCA2 | 0.01 |
| S15 LN1 | 0.00 |
| S16 Lab1 | 0.00 |
| S17 LN14 | 0.01 |
| S18 LA13 | 0.00 |
| S9 NHDF2 | 0.00 |
| S10 NHDF3 | 0.00 |
| S55 JEHC | 0.00 |
| S56 HT 1080 | 0.00 |
| S57 MRC-5 | 0.01 |
| S152 Cells Mob | 0.00 |
| S155 Cells Mob stimuled | 0.00 |
| S156 Cells Mob stimuled | 0.00 |
| S20 K1 Keratinocytes Skin | 0.00 |
| S21 K2 Keratinocytes Skin | 0.16 |

TABLE 8

| Primary cells and cell lines 2 - immune and CNS derived | Relative to GAPDH (=100) |
|---|---|
| S30 THP-1 mono/mac | 0.00 |
| S35 KU812 basophil | 0.10 |
| S37 KU812/PMA | 0.05 |
| S43 Jurkat | 0.00 |
| S58 PBMC1 | 0.00 |
| S59 Granulocytes 1 | 0.02 |
| S61 PBMC2.2 | 0.00 |
| S97 SK-N-AS | 0.00 |
| S98 TE671 subclone 2 | 0.04 |
| S99 KELLY | 0.00 |
| S100 U-373 MG | 0.00 |
| S101 U-87 MG | 0.00 |
| S102 T98G | 0.00 |
| S103 BE(2)-C | 0.04 |
| S104 CCF-STGG1 | 0.00 |
| S105 TE671 | 0.01 |
| S106 A172 | 0.00 |
| S107 132N1 | 0.00 |
| S108 SK-PN-DW | 0.01 |
| S109 SK-N-SH | 0.26 |
| S38 MOLT-4 | 0.01 |
| S41 EOL-3 | 0.06 |
| S44 EOL-3 + IL2 | 0.02 |

TABLE 9

| IBD biopsies | Relative to GAPDH (=100) |
|---|---|
| N1 | 0.02 |
| N2 | 0.09 |
| N3 | 0.02 |
| N4 | 0.03 |
| N5 | 0.01 |
| N9 | 0.01 |
| N10 | 0.03 |
| CD1 | 0.59 |
| CD2 | 0.07 |
| CD3 | 0.30 |
| CD4 | 0.03 |
| CD5 | 0.01 |
| CD6 | 0.13 |
| CD8 | 0.15 |
| CD9 | 0.02 |
| CD10 | 0.15 |
| CD13 | 0.20 |
| CD16 | 0.31 |
| CD17 | 0.16 |
| CD18 | 0.03 |
| CD19 | 0.02 |
| CD20 | 0.02 |
| CD22 | 0.07 |
| N11 | 0.30 |
| N14 | 0.05 |
| N26 | 2.19 |
| N27 | 2.79 |
| N29 | 0.79 |
| N30 | 0.39 |
| CD4 bis | 0.25 |
| CD6 bis | 0.35 |
| CD23 | 0.24 |
| CD24 | 0.54 |
| CD25 | 0.10 |
| CD26 | 0.39 |
| CD27 | 0.11 |
| CD28 | 0.61 |
| UC11 | 0.90 |
| UC12 | 0.31 |
| UC13 | 0.01 |
| UC14 | 1.21 |
| UC16 | 0.58 |
| UC18 | 0.02 |
| UC19 | 0.01 |

Figure 6:
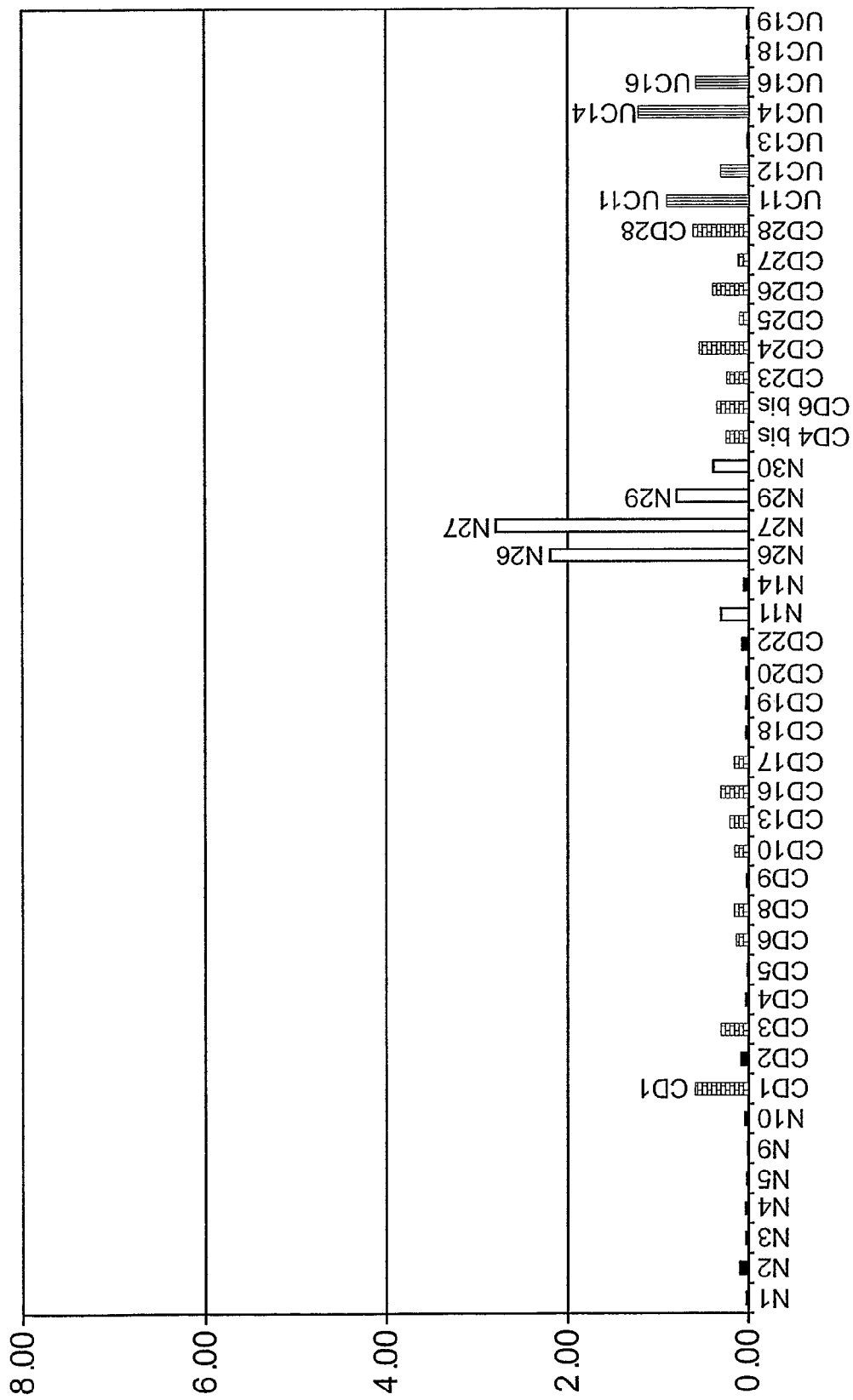
FIG. 6: Taqman analysis of INSP201-EC for various inflammatory bowel disease (IBD) biopsies (table 7)
Figure 7:
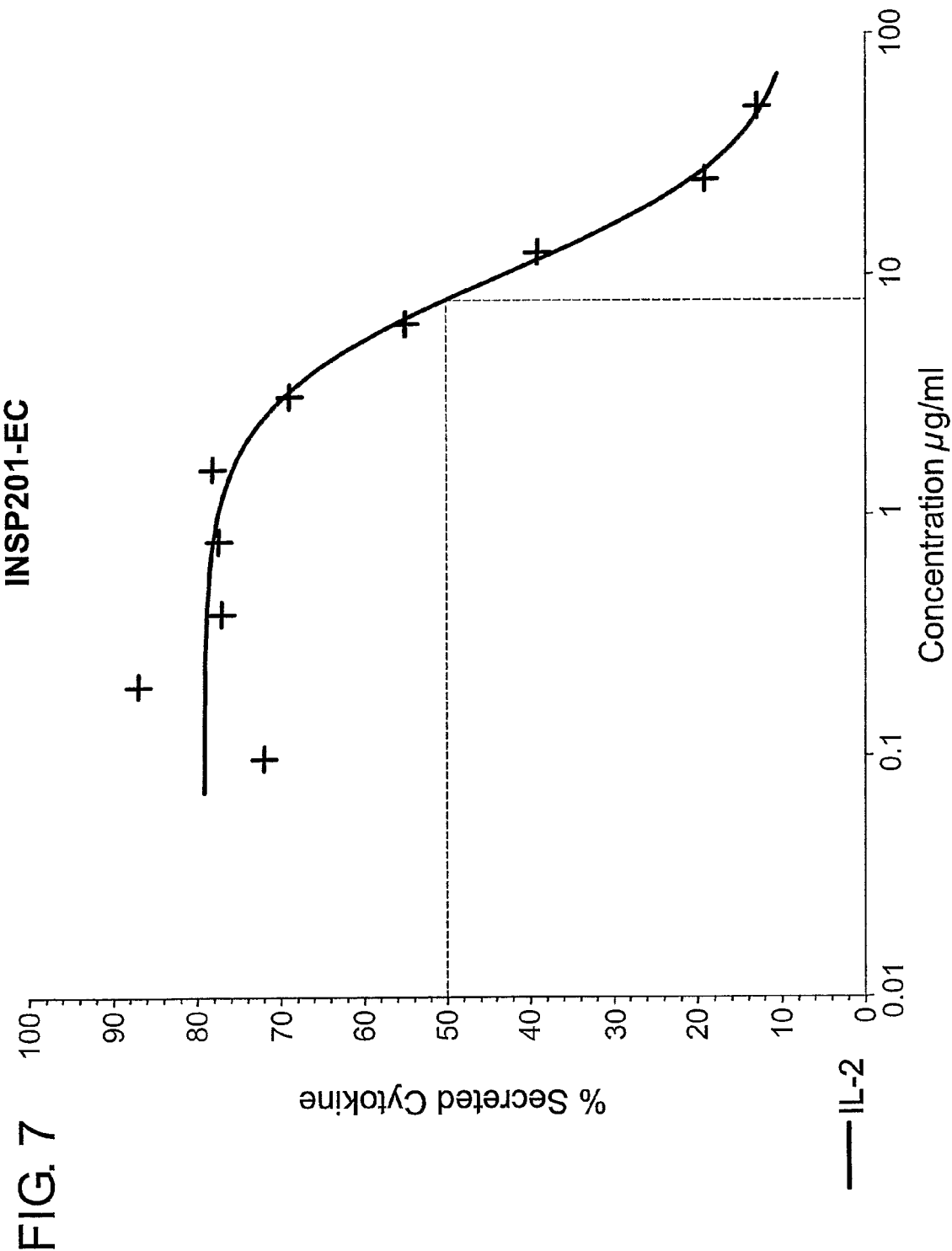
FIG. 7: INSP201-EC inhibition of IL-2 secretion from ConA-stimulated PBMC. The X-axis represents the AS902132/2 concentration in μg/ml. The Y-axis represents the percentage of cytokine secretion (IL-2).

Defining a threshold of Expression level of INSP201-EC relative to GAPDH expression of 0.3, TaqMan expression results show unexpected restricted expression of INSP163 in one pancreas tissue (table 4 and FIG. 4), one lung tumor tissue (table 5 and FIG. 5), and at high levels in various inflammatory bowel diseases tissues (table 9 and FIG. 6). No expression of INSP201-EC is seen in normal lung tissues (expression level of INSP201-EC relative to GAPDH is below 0.03). The lung tumor is a bronchogenic carcinoma, more specifically a squamous cell carcinoma.

This specific pattern of expression leads to the conclusion of the involvement of INSP201-EC in lung cancer and inflammatory bowel diseases. These surprising properties characterizing the polynucleotides or the corresponding polypeptides of the present invention make them particularly suitable for the preparation of a drug or pharmaceutical composition. The polynucleotides or the corresponding polypeptides of the present invention therefore display the unexpected finding of a restricted expression in one pancreas tissue, one lung tumor tissue and in various inflammatory bowel diseases tissues.

EXAMPLE 6

Determination of Cytokine Levels Produced by Human PBMC Stimulated with ConA Using Cytometry Beads Array (CBA)

6.1 Summary

The goal of the study is to find new modulators of cytokine secretion using Human Peripheral Mononuclear Cells (PBMC) stimulated with the mitogen concanavalin A (ConA).

The protein INSP201-EC inhibits IL-2 secretion from ConA-stimulated human PBMC with an Emax=80% and an EC50=8 µg/ml, no effect was seen on the levels of IFN-γ, TNF-α, IL-4, IL-5 or IL-10.

6.2 Equipments and Softwares
96 well microtiter plate photometer EX (Labsystem).
Graph Pad Prism Software
Excel software
Flow cytometer Becton-Dickinson
CBA Analysis software
Hood for cell culture
Incubator for cell culture
Centrifuge
Pipettes 6.3 Materials and Reagents
Buffy Coat
DMEM GIBCO Ref: 21331-020
Human serum type AB SIGMA Ref: H1513
L-Glutamine GIBCO Ref: 250 030-020
Penicillin-Streptomycin GIBCO Ref: 150 070-063
Ficoll PHARMACIA ref: 17-1440-03
96 well microtiter plate for cell culture COSTAR Ref: 3596
Concanavalin A SIGMA Ref: C0412
Dexamethasone water soluble SIGMA Ref: D2915
Human Th1/Th2 Cytokine CBA Kit Becton-Dickinson Ref: 550749
PBS GIBCO Ref: 14190-094
FALCON 50 ml sterile Becton-Dickinson Ref: 2070
Glycerol MERCK Ref: 1-04092-2500
96 well microtiter plate conical bottom NUNC Ref: 249570

6.4 Method
Purification of Human PBMC from a Buffy Coat
  Dilute the buffy coat 1 to 2 with DMEM.
  Slowly add 25 ml of diluted blood onto a 15 ml layer of Ficoll in a 50 ml Falcon tube.
  Centrifuge the tubes (2000 rpm, 20 min, at RT without brake).
  Collect the interphase (ring) and wash the cells with 25 ml of DMEM followed by a centrifuge step (1200 rpm, 5 min). Repeat 3 times. A buffy coat would give approximately 600× $10^6$ total cells.

Activity Test
  Add 80 µl of 1.25×$10^6$ cells/ml, diluted in DMEM+2.5% Human Serum+1% L-Glutamine+1% Penicillin-Streptomycin, to a 96 well microtiter plate.
  Add 10 µl per well (one condition per well): INSP201-EC in PBS+20% Glycerol (starting concentration 50 µg/ml)
  Add 10 µl per well: ConA 50 µg/ml (the final concentration of ConA is 5 µ/g/ml)
  After 48 h, cell supernatants are collected and human cytokines measured by Human Th1/Th2 Cytokine CBA Kit Becton-Dickinson.

CBA Analysis
  Human Th1/Th2 Capture Beads mixture is prepared following the supplier instructions (CBA Kit Becton-Dickinson Ref: 550749), briefly:
  Determine the number of assay tubes that are required for the experiment.
  Vigorously vortex each capture bead suspension for a few seconds before mixing.
  Add a 10 µl aliquot of each capture bead, for each assay to be analysed, into a single tube labelled "mixed capture beads".
  Vortex the Bead mixture thoroughly.

Preparation of Test Samples
  Dilute supernatants 1:5 using the Assay Diluent (20 µl of supernatants+60 µl of Assay Diluent).
  Mix sample dilution before transferring samples into a 96 wells microtiter plate conical bottom. (Nunc)

Human Th1/Th2 Cytokine CBA Assay Procedure
  Add 50 µl of the diluted supernatants into a 96 wells microtiter plate conical bottom (Nunc).
  Add 50 µl of the mixed capture beads.
  Add 50 µl of the Human Th1/Th2 PE Detection Reagent.
  Incubate the plate for 3 hours at RT and protect from direct exposure to light.
  Centrifuge at 1500 rpm for 5 minutes.
  Carefully discard the supernatant.
  Add 200 µl of wash buffer to each well and centrifuge at 1500 rpm for 5 minutes.
  Carefully discard the supernatant.
  Add 200 µl of Wash Buffer to each well and centrifuge at 1500 rpm for 5 minutes.
  Carefully discard the supernatant.
  Add 130 µl of wash buffer to each well to resuspend the bead pellet.
  Analyse samples on a flow cytometer.
  The data are analysed using the CBA Application Software, Activity Base and Microsoft Excel software.
  The results are given in percentage of cytokine secretion compare to the level of cytokine achieved by ConA stimulation (100%) versus non stimulated cells (0%).

6.5 Results—Effect of INSP201-EC Administration to ConA-Stimulated Human PBMC

Results show inhibition of IL-2 secretion in the presence of INSP201-EC in a dose response manner. The maximum inhibition (Emax) achieved is 80% with an EC50 of 8 µg/ml. No effect was seen on the levels of IFN-γ, TNF-α, IL-4, IL-5 or IL-10. The inhibition is therefore specific for IL-2.

Considering the down regulation of IL-2 from human peripheral mononuclear cells and INSP201-EC's expression in inflammatory bowel disease, cancer and pancreatic tissues, this is an indication of the involvement of INSP201-EC in inflammation, IL-2 related diseases, cancer, inflammatory bowel diseases and/or pancreatic disorder.

Agonists of IL-2 are known. For example, Abbott developed an IL-2 fusion protein for the treatment of neoplasm. Amgen developed an IL-2 agonist for the treatment of cancer. AntiCancer Inc developed an IL-2 agonist (AC-9401) for the treatment of lung tumor. AplaGen GmbH developed an IL-2 agonist (IL-2 mimetic peptides) for the treatment of cancer. Avectin developed an IL-2 agonist (avectin) for the treatment of breast tumor. Aventis Pharma developed an IL-2 agonist for the treatment of cancer. Bayer Corp developed an IL-2 agonist (BAY-50-4798) for the treatment of HIV infection, renal cell carcinoma and melanoma. Baylor College of Medicine developed an IL-2 agonist (IL-2/CD40L-expressing leukemia vaccine) for the treatment of chronic lymphocytic leukemia. Biogen developed an IL-2 modulator (teceleukin) for the treatment of sarcoma, acquired immune deficiency syndrome, cancer, colon tumor and renal tumor. Biomira USA developed an TL-2 agonist (liposome formulation, peptide) for the treatment of non-small-cell lung cancer, HIV infection, lung tumor and renal tumor. Boehringer Ingelheim developed BIWB-2 (vaccine) for the treatment of melanoma, neoplasm. Chiron Corp. developed aldeseukin for the treatment of HIV infection, renal cell carcinoma, leukemia, melanoma, non Hodgkin lymphoma, cancer, lung tumor, ovary tumor. Chiron Corp. developed as well a PEG-interleukin-2 for the treatment of HIV infection and head and neck tumor. EMD Lexigen Research developed EMD-273063 (monoclonal antibody-fusion protein) for the treatment of melanoma and nervous system tumor. EMD Lexigen Research developed NHS-IL-2(D20T) (conjugated immunoglobulin) for the treatment of cancer. Flamel Technologies developed a IL-2 agonist for the treatment of cancer. Immunex developed a recombinant peptide for the treatment of Hepatitis B virus infection, melanoma and cancer. The Institute of Cancer Research developed a vaccine for the treatment of cancer. The McMaster University developed a vaccine (adenovirus based gene therapy) for the treatment of melanoma, breast tumor and cancer. The Medical University of South Carolina developed a peptide-GN_CSF/IL-2 vaccination therapy for the treatment of cancer. The National Institute of Health developed an IL-2 gene therapy for the treatment of renal cell carcinoma, melanoma and colon tumor. Pivotal BioSciences developed an IL-2 agonist (PB-1) for the treatment of cancer. The Scripps Research Institute developed KS-IL-2 (monoclonal antibody—conjugated—fusion protein) for the treatment of non-small-cell lung cancer, prostate tumor, breast tumor, cancer, brain tumor, ovary tumor, colorectal tumor and renal tumor. Seragen developed DAB-486IL-2 (protein fusion-toxin) for the treatment of HIV infection, neoplasm, rheumatoid arthritis and insulin dependent diabetes. Seragen developed as well denileukin diftitox (protein fusion-toxin) for the treatment of non-small-cell lung cancer, alopecia, HIV infection, chronic lymphocytic leukaemia, cutaneous T-cell lymphoma, lymphoma, psoriasis, rheumatoid arthritis, non-Hodgkin lymphoma, graft versus host disease, head and neck tumor, lung tumor and dermatitis. SkyePharma developed an IL-2 agonist (peptide) for the treatment of infection. The St Jude Childrens Research Hospital developed an IL-2 agonist (vaccine) for the treatment of nervous system tumor. The State Research Center of Virology and Biotechnology VECTOR developed an IL-2 agonist (peptide) for the treatment of cancer. Takeda Pharmaceutical developed celmoleukin for the treatment of hepatitis B virus infection and cancer. Transgene SA developed TG-1024 (adenovirus based gene therapy) for the treatment of melanoma and solid tumor. Transgene SA developed TG-1031 and TG-4010 (Pox virus based gene therapy) for the treatment of non-small-cell lung cancer, pancreas tumor, prostate tumor, breast tumor and ovary tumor. Cell Therapy developed TG-2001 for the treatment of mesothelioma, renal cell carcinoma, sarcoma, melanoma and breast tumor cancer. Transkaryotic Therapies developed IL-2, TKT for the treatment of renal cell carcinoma. The University of California developed UCLA for the treatment of melanoma, prostate tumor and colon tumor. The University of Cincinnati developed a vaccinia virus therapy for the treatment of head and neck tumor and cancer. The University of Pittsburgh developed an IL-2 agonist (peptide) for the treatment of neoplasm. The University of Texas developed INGN-301 for the treatment of HIV infection. Valentis/Roche developed IL-2, cLipid gene therapy for the treatment of Head and Neck tumor. Valentis developed IL-2/superantigen-B, cLipid gene therapy for the treatment of melanoma. Valentis developed as well VLTS-587 for the treatment of lung tumor. Vical developed an IL-2 agonist (gene therapy — plasmid) for the treatment of melanoma. Vical developed leuvectin for the treatment of renal cell carcinoma, sarcoma, lymphoma, melanoma and prostate tumor. Virogenetics Corp developed ALVAC-hIL-2 (Pox virus based gene therapy) for the treatment of cancer. Yead Research developed an IL-2 agonist for the treatment of neurodegenerative disease.

Antagonists of IL-2 are known. For example, Affymax/Aventis developed an immunosuppressant IL-2 antagonist for the treatment of rheumatoid arthritis, autoimmune disease and cardiovascular disease. Hybritech Inc. developed a monoclonal antibody for the treatment of cancer. Immunotech developed a monoclonal antibody for the treatment of transplant rejection versus host disease. Sunesis Pharmaceuticals developed an IL-2 antagonist for the treatment of graft versus host disease.

Interleukin-2 function, production and clinical applications have been reviewed by Graffen and Liu (Cytokine 28 (2004), pp. 109-123).

As such an IL-2 related disease is neoplasm, lung tumor, cancer, breast tumor, HIV infection, renal cell carcinoma, melanoma, chronic lymphocytic leukemia, sarcoma, acquired immune deficiency syndrome, colon tumor, renal tumor, non-small-cell lung cancer, leukemia, non-Hodgkin lymphoma, ovary tumor, head and neck tumor, nervous system tumor, Hepatitis B virus infection, prostate tumor, brain tumor, colorectal tumor, renal tumor, alopecia, cutaneous T-cell lymphoma, lymphoma, nervous system tumor, solid tumor, pancreas tumor, mesothelioma, anemia, ulcerative colitis, gastric cancer, scleroderma, rheumatoid arthritis, inflammatory bowel disease, chronic hepatitis B infection, hypergammaglobulinemia, Epstein-Barr virus mediated lymphoproliferative disorders, acute myelocytic leukaemia, metastatic melanoma, arthritis, leukopenia, thrombocytopenia, angiogenesis disorder, Kaposi's sarcoma, pancreatic disorder or multiple sclerosis.

Preferably, "cancer" is selected among cancer from blood and lymphatic systems, skin cancers, cancer of digestive systems, cancers of urinary systems, breast cancer, ovarian cancer, gynecological cancers, choriocarcionoma, lung cancer, Brain Tumors, Bone Tumors, Carcinoid Tumor, Nasopharyngeal Cancer, Retroperitoneal sarcomas, Soft Tissue Tumors, Thyroid Cancer or Cancers of Unknown Primary Site.

Preferably, "tumors of the lungs" or "lung cancer", as used interchangeably herein, are selected from benign or malignant primary tumors or from metastases from primary cancers of many other organs and tissues.

Preferably the lung cancer is selected from primary lung tumors including bronchogenic carcinoma, bronchial carcinoid, chondromatous hamartoma (benign), solitary lymphoma, sarcoma (malignant) or multifocal lymphomas.

Preferably, the bronchogenic carcinoma is selected from squamous cell carcinoma, undifferentiated small cell carcinoma, undifferentiated large cell carcinoma, adenocarcinoma or Bronchioloalveolar carcinoma.

Preferably, the bronchogenic carcinoma is squamous cell carcinoma or non-small cell lung carcinoma.

Preferably the lung cancer is selected from metastases from primary cancers of the skin, breast, colon, prostate, kidney, thyroid, stomach, cervix, rectum, testis, and bone and from melanoma.

"Bronchial carcinoid" or "bronchial adenoma", terms that can be used interchangeably, may be benign or malignant and occurs equally in both sexes. Its course is prolonged. The endobronchial portion of the tumor may obstruct the lumen of major bronchi. Brisk bleeding from the overlying mucous membrane often occurs. Recurrent pneumonia within the same lung zone and localized overlying pleural pain are common. Metastases are uncommon but may occur to regional lymph nodes.

Preferably, the pancreatic disorder is acute pancreatitis, chronic pancreatitis, pancreatic carcinoma, including acinar cell carcinoma or mixed cell population pancreatic carcinoma.

Preferably, the inflammatory bowel disease is Crohn's disease or ulcerative colitis.

Preferably, the extracellular part of membrane-bound INSP201 (whether glycosylated or not), fragments thereof, agonists thereof or antagonists of membrane bound INSP201 are useful for the treatment of inflammation, IL2-related disorder and/or inflammatory bowel disease as well as in solid organ and bone marrow transplantation. A combination with cyclosporine A, tacrolimus or sirolimus can be used for solid organ and bone marrow transplantation.

Preferably, antagonists of membrane bound INSP201 are neutralizing antibodies.

Preferably, an INSP201 polypeptide lacking the transmembrane domain is used for the treatment of inflammation, IL2-related disorder and/or inflammatory bowel disease.

Preferably, the transmembrane domain spans from amino acids 406 to 428 of SEQ ID NO:8 or SEQ ID NO:24.

Preferably, agonists of membrane-bound INSP201 are used for the treatment of cancer (e.g. lung cancer, RCC or melanoma) and/or IL-2 related disorder such as HIV, EBV or hepatitis B infections.

Preferably, agonists of membrane bound INSP201 are agonistic antibodies.

Preferably, the extracellular part of membrane-bound INSP201 consists or comprises of SEQ ID NO:14, SEQ ID NO: 18, SEQ ID NO:22 or SEQ ID NO:28. Preferably, a fragment of the extracellular part of membrane bound INSP201 consists or comprises of SEQ ID NO:2, SEQ ID NO:10, SEQ ID NO:20 or SEQ ID NO:26.

Preferably, the membrane-bound INSP201 consists or comprises of SEQ ID NO:8, SEQ ID NO:12; SEQ ID NO:24, SEQ ID NO:30, or a combination of exons 1 and exons 2 (i.e. SEQ ID NO:2, SEQ ID NO:10, SEQ ID NO:20 or SEQ ID NO:26 in combination with SEQ ID NO:4).

EXAMPLE 7

Assay for Determining IKK2 Activity in Non-Small Cell Lung Carcinoma Cells (A549)

Tumor necrosis factor-α (TNF α) is a pleiotropic cytokine with multiple functions including cell activation, differentiation and apoptosis. TNFα exerts both apoptotic and antipoptotic effects in cell-type specific manner. The antiapoptotic effects of TNFα appears to be mediated by the upregulation of NF-κB activity. TNFα induced activation of NF-κB increases the expression of several antiapoptotic proteins that protect cells from cell death. When this pathway is inhibited, TNFα, can potentially induce cell death. Activation of NF-κB is mediated by IKK complex.

The activity of INSP201-EC, fusion thereof or an antibody targeted to INSP201 can be demonstrated by the following assay that can measure the activation of IKK2 activity in A549 cells, a human lung carcinoma cell. Since TNFα can induce both pro- and anti-apoptotic pathway, blocking the anti-apoptotic gene expression by cycloheximide can lead to cell death. Once the cells undergo apoptosis, they detach from the culture surface. Upon fixing the cells with crystal violet followed by washing, only live cells are stained and this could be read at 540 nm. Thus, this measure is used to determine cell death in A549 cells. When A549 cells are treated with TNFα in the presence of cycloheximide, it results in apoptosis. Upon pretreating cells with IL-1β or TNFα, to induce the IKK pathway, thus upregulate the anti-apoptotic genes, it can protect cells from death induced by TNFα+cycloheximide treatment. During the pretreatment step with IL-1β, blocking IKK activity with a specific inhibitor can abolish the protective effect of IL1β on TNFα+cycloheximide mediated cell death. Thus, this property of TNFα signaling is used to monitor IKK activity in A549 cells. The IKK-inhibitor can dose-dependently block IL-1β-mediated protective effect in A549 cells, while with EGF there is no protective effect. The protocol followed for monitoring IKK activity is as follows:

1) A549 Cells are seeded (50,000 cells/well) and cultured overnight,
2) The cells are pretreated with IL-1β (1 ng/ml) or TNF-α with or without the compound, i.e. INSP201-EC, fusion thereof or antibody targeted to INSP201, in serum free media for overnight. The compound is a specific inhibitor of IKK activity,
3) The cells are treated with TNF-α and cycloheximide for 8 hours, and
4) Cell death is monitored with crystal violet.

EXAMPLE 8

Animal Models

Activity of INSP201-EC, fusion thereof or antibody targeted to INSP201 can be demonstrated in models of cancer as reviewed by Kamb and Lassota (Drug Discovery Today: Disease Models; Vol. 1, No. 1, 2004, pp. 31-36), in models of lung cancer as reviewed by Láhm and Fischer (Drug Discovery Today: Disease Models; Vol. 1, No. 1, 2004, pp. 25-30), or in models of inflammatory bowel disease as reviewed by Borm et Bouma (Drug Discovery Today: Disease Models; Vol. 1, No. 4, 2004, pp. 437-443).

In addition, the activity of a polypeptide of the present invention can be confirmed in at least one of the following assays:
a. INSP201-EC, fusion thereof or antibody targeted to INSP201 can modulate the proliferation or the survival of normal and cancerous cells, or
b. INSP201-EC, fusion thereof or antibody targeted to INSP201 can modulate IL-2 secretion in ConA assay (Example 6), or
c. INSP201-EC, fusion thereof or antibody targeted to INSP201 can modulate IKK2 activity in A549 cells, a human lung carcinoma cell (Example 7).

The invention claimed is:

1. An isolated nucleic acid encoding a polypeptide having at least 98% sequence identity to a polypeptide comprising SEQ ID NO: 18, wherein said encoded polypeptide inhibits IL-2 secretion.

2. The isolated nucleic acid of claim 1, wherein said nucleic acid encodes a polypeptide comprising SEQ ID NO: 18.

3. The isolated nucleic acid of claim 1, wherein said nucleic acid encodes a polypeptide consisting of SEQ ID NO: 18.

4. An isolated vector comprising a nucleic acid encoding a polypeptide having at least 98% sequence identity to a polypeptide comprising SEQ ID NO: 18, wherein said encoded polypeptide inhibits IL-2 secretion.

5. The isolated vector of claim 4, wherein said nucleic acid encodes a polypeptide comprising SEQ ID NO: 18.

6. The isolated vector of claim 4, wherein said nucleic acid encodes a polypeptide consisting of SEQ ID NO: 18.

7. An isolated host cell comprising a vector comprising a nucleic acid encoding a polypeptide having at least 98% sequence identity to a polypeptide comprising SEQ ID NO: 18, wherein said encoded polypeptide inhibits IL-2 secretion.

8. The isolated host cell of claim 7, wherein said vector comprises a nucleic acid that encodes a polypeptide comprising SEQ ID NO: 18.

9. The isolated host cell of claim 7, wherein said vector comprises a nucleic acid that encodes a polypeptide consisting of SEQ ID NO: 18.

10. A method of making a polypeptide having at least 98% sequence identity to a polypeptide comprising SEQ ID NO: 18 comprising culturing a host cell of claim 7 under conditions that permit the expression of a polypeptide having at least 98% sequence identity to a polypeptide comprising SEQ ID NO: 18 encoded by said nucleic acid.

11. The method of claim 10, wherein said polypeptide comprises SEQ ID NO: 18.

12. The method of claim 10, wherein said polypeptide consists of SEQ ID NO: 18.

* * * * *

UNITED STATES PATENT AND TRADEMARK OFFICE
CERTIFICATE OF CORRECTION

| | |
|---|---|
| PATENT NO. | : 8,124,748 B2 |
| APPLICATION NO. | : 11/660014 |
| DATED | : February 28, 2012 |
| INVENTOR(S) | : Stephen Fitzgerald et al. |

It is certified that error appears in the above-identified patent and that said Letters Patent is hereby corrected as shown below:

Column 3,
Line 45, "thorough the" should read --through the--.
Line 50, "The N-" should read --the N- --.

Column 17,
Lines 7-8, "member known members" should read --known members--.
Line 25, "complimentarily" should read --complimentarity--.
Line 33, "5,5301,101;" should read --5,530,101;--.

Column 19,
Line 40, "any of wide" should read --any wide--.

Column 21,
Line 25, "sulffiydryl" should read --sulfhydryl--.

Column 22,
Line 9, "species" should read --species.--.

Column 27,
Line 49, "ME Research" should read --MJ Research--.

Column 30,
Line 42, "periplasrnic" should read --periplasmic--.

Column 31,
Line 45, "BEK 293" should read --HEK 293--.

Column 32,
Line 21, "G418" should read --G-418--.

Signed and Sealed this
Twenty-ninth Day of May, 2012

David J. Kappos
*Director of the United States Patent and Trademark Office*

CERTIFICATE OF CORRECTION (continued)
U.S. Pat. No. 8,124,748 B2

Column 61,
Line 52, "5µ/g/ml" should read --5µg/ml--.

Column 62,
Line 58, "an TL-2" should read --an IL-2--.

Column 63,
Line 21, "DAB-486IL-2" should read --DAB-486-IL-2--.

Column 64,
Line 29, "choriocarcionoma" should read --choriocarcinoma--.

Column 66,
Line 12, "IL1β" should read --IL-1β--.